US009638656B2

(12) United States Patent
Malecha

(10) Patent No.: US 9,638,656 B2
(45) Date of Patent: May 2, 2017

(54) ACCURATE ANALYTE MEASUREMENTS FOR ELECTROCHEMICAL TEST STRIP BASED ON MULTIPLE DISCRETE MEASUREMENTS DEFINED BY SENSED PHYSICAL CHARACTERISTIC(S) OF THE SAMPLE CONTAINING THE ANALYTE

(71) Applicant: LIFESCAN SCOTLAND LIMITED, Beechwood Park North, Inverness, Inverness-shire (GB)

(72) Inventor: Michael Malecha, Muir of Ord (GB)

(73) Assignee: LifeScan Scotland Limited, Inverness (GB)

( * ) Notice: Subject to any disclaimer, the term of this patent is extended or adjusted under 35 U.S.C. 154(b) by 284 days.

(21) Appl. No.: 14/354,377

(22) PCT Filed: Dec. 28, 2012

(86) PCT No.: PCT/GB2012/053277
§ 371 (c)(1),
(2) Date: Apr. 25, 2014

(87) PCT Pub. No.: WO2013/098564
PCT Pub. Date: Jul. 4, 2013

(65) Prior Publication Data
US 2014/0291167 A1 Oct. 2, 2014

Related U.S. Application Data

(60) Provisional application No. 61/581,087, filed on Dec. 29, 2011, provisional application No. 61/581,089, (Continued)

(51) Int. Cl.
*G01N 17/00* (2006.01)
*G01N 27/327* (2006.01)
(Continued)

(52) U.S. Cl.
CPC ......... *G01N 27/3274* (2013.01); *G01N 27/26* (2013.01); *G01N 27/3272* (2013.01); *G06F 19/24* (2013.01)

(58) Field of Classification Search
CPC ........... G01N 27/3274; G01N 27/3272; G01N 27/26; G06F 19/24
See application file for complete search history.

(56) References Cited

U.S. PATENT DOCUMENTS

| 4,919,770 A | 4/1990 | Preidel et al. |
| 5,001,048 A | 3/1991 | Taylor et al. |

(Continued)

FOREIGN PATENT DOCUMENTS

| AU | 738325 B2 | 9/2001 |
| EP | 749332 B1 | 3/1995 |

(Continued)

OTHER PUBLICATIONS

U.S. Appl. No. 61/530,795, filed Sep. 2, 2011, McColl et al.
(Continued)

*Primary Examiner* — Dennis M White

(57) ABSTRACT

Various embodiments that allow for a more accurate analyte concentration by determining at least one physical characteristic, particularly hematocrit, of the blood sample containing the analyte, particularly glucose, and deriving a specific sampling time based on a relationship between the physical characteristic and sampling time so that the analyte concentration can be determined with greater accuracy with the specific sampling time point.

41 Claims, 42 Drawing Sheets

Related U.S. Application Data filed on Dec. 29, 2011, provisional application No. 61/581,099, filed on Dec. 29, 2011, provisional application No. 61/581,100, filed on Dec. 29, 2011, provisional application No. 61/654,013, filed on May 31, 2012.

(51) Int. Cl.
  *G01N 27/26* (2006.01)
  *G06F 19/24* (2011.01)

(56) References Cited

U.S. PATENT DOCUMENTS

| | | |
|---|---|---|
| 5,243,516 A | 9/1993 | White |
| 5,429,735 A | 7/1995 | Johnson et al. |
| 5,437,999 A | 8/1995 | Diebold et al. |
| 5,508,203 A | 4/1996 | Fuller et al. |
| 5,704,354 A | 1/1998 | Preidel et al. |
| 5,708,247 A | 1/1998 | McAleer et al. |
| 5,792,668 A | 8/1998 | Fuller et al. |
| 5,951,836 A | 9/1999 | McAleer et al. |
| 6,001,239 A | 12/1999 | Douglas et al. |
| 6,179,979 B1 | 1/2001 | Hodges et al. |
| 6,193,873 B1 | 2/2001 | Ohara et al. |
| 6,241,862 B1 | 6/2001 | McAleer et al. |
| 6,284,125 B1 | 9/2001 | Hodges et al. |
| 6,287,451 B1 | 9/2001 | Winarta et al. |
| 6,391,645 B1 | 5/2002 | Huang et al. |
| 6,413,410 B1 | 7/2002 | Hodges et al. |
| 6,475,372 B1 | 11/2002 | Ohara et al. |
| 6,517,482 B1 | 2/2003 | Elden et al. |
| 6,576,117 B1 | 6/2003 | Iketaki et al. |
| 6,645,368 B1 | 11/2003 | Beaty et al. |
| 6,685,633 B2 | 2/2004 | Albert et al. |
| 6,716,577 B1 | 4/2004 | Yu et al. |
| 6,733,655 B1 | 5/2004 | Davies et al. |
| 6,749,887 B1 | 6/2004 | Dick et al. |
| 6,767,441 B1 | 7/2004 | Cai et al. |
| 6,841,389 B2 | 1/2005 | Novikov et al. |
| 6,863,801 B2 | 3/2005 | Hodges et al. |
| 6,890,421 B2 | 5/2005 | Ohara et al. |
| 7,018,843 B2 | 3/2006 | Heller |
| 7,045,046 B2 | 5/2006 | Chambers et al. |
| 7,050,847 B2 | 5/2006 | Ollmar et al. |
| 7,258,769 B2 | 8/2007 | Cui et al. |
| 7,291,256 B2 | 11/2007 | Teodorczyk et al. |
| 7,338,639 B2 | 3/2008 | Burke et al. |
| 7,390,667 B2 | 6/2008 | Burke et al. |
| 7,407,811 B2 | 8/2008 | Burke et al. |
| 7,452,457 B2 | 11/2008 | Burke et al. |
| 7,488,601 B2 | 2/2009 | Burke et al. |
| 7,494,816 B2 | 2/2009 | Burke et al. |
| 7,498,132 B2 | 3/2009 | Yu et al. |
| 7,597,793 B2 | 10/2009 | Burke et al. |
| 7,601,249 B2 | 10/2009 | Iyengar et al. |
| 7,604,721 B2 | 10/2009 | Groll et al. |
| 7,645,373 B2 | 1/2010 | Groll et al. |
| 7,645,421 B2 | 1/2010 | Groll |
| 7,678,250 B2 | 3/2010 | Bell et al. |
| 7,718,439 B2 | 5/2010 | Groll |
| 7,727,467 B2 | 6/2010 | Burke et al. |
| 7,749,437 B2 | 7/2010 | Mosoiu et al. |
| 7,751,864 B2 | 7/2010 | Buck, Jr. |
| 7,829,023 B2 | 11/2010 | Burke et al. |
| 7,879,618 B2 | 2/2011 | Mosoiu et al. |
| 7,892,849 B2 | 2/2011 | Burke et al. |
| 7,923,258 B2 | 4/2011 | Heller |
| 7,927,882 B2 | 4/2011 | Heller |
| 7,955,492 B2 | 6/2011 | Fujiwara et al. |
| 7,964,089 B2 | 6/2011 | Harding et al. |
| 7,972,851 B2 | 7/2011 | Wang et al. |
| 7,972,861 B2 | 7/2011 | Deng et al. |
| 8,080,153 B2 | 12/2011 | Feldman et al. |
| 8,083,925 B2 | 12/2011 | Feldman et al. |
| 8,088,271 B2 | 1/2012 | Fujiwara et al. |
| 8,148,164 B2 | 4/2012 | Diebold et al. |
| 8,409,424 B2 | 4/2013 | Chen et al. |
| 8,623,660 B2 | 1/2014 | Kraft et al. |
| 2004/0005716 A9 | 1/2004 | Beaty et al. |
| 2004/0079652 A1 | 4/2004 | Vreeke et al. |
| 2004/0157339 A1 | 8/2004 | Burke et al. |
| 2006/0231421 A1 | 10/2006 | Diamond et al. |
| 2007/0084734 A1 | 4/2007 | Roberts et al. |
| 2007/0087397 A1 | 4/2007 | Kraft et al. |
| 2007/0235346 A1 | 10/2007 | Popovich et al. |
| 2008/0083618 A1 | 4/2008 | Neel et al. |
| 2008/0274447 A1 | 11/2008 | Mecklenburg |
| 2009/0177406 A1 | 7/2009 | Wu |
| 2009/0223834 A1 | 9/2009 | Cai et al. |
| 2009/0236237 A1 | 9/2009 | Shinno et al. |
| 2010/0005865 A1 | 1/2010 | Miura |
| 2010/0089775 A1 | 4/2010 | Chen et al. |
| 2010/0170807 A1 | 7/2010 | Diebold et al. |
| 2010/0206749 A1 | 8/2010 | Choi |
| 2010/0276303 A1 | 11/2010 | Fujiwara et al. |
| 2010/0283488 A1 | 11/2010 | Nakamura et al. |
| 2010/0320097 A1 | 12/2010 | Miyazaki et al. |
| 2011/0030093 A1 | 2/2011 | Dhugga |
| 2011/0036729 A1 | 2/2011 | Matsuda et al. |
| 2011/0168575 A1 | 7/2011 | Lica et al. |
| 2011/0294554 A1 | 12/2011 | Barratt et al. |
| 2011/0297554 A1 | 12/2011 | Wu et al. |
| 2011/0297557 A1 | 12/2011 | Wu et al. |
| 2011/0301857 A1 | 12/2011 | Huang et al. |
| 2012/0031777 A1 | 2/2012 | Burke et al. |
| 2012/0043227 A1 | 2/2012 | Miyazaki et al. |
| 2012/0129423 A1 | 5/2012 | Finizza |
| 2013/0105334 A1 | 5/2013 | Nakamura et al. |

FOREIGN PATENT DOCUMENTS

| | | |
|---|---|---|
| EP | 691539 B1 | 6/1995 |
| EP | 1394545 A1 | 3/2004 |
| EP | 1828759 B1 | 10/2005 |
| EP | 1804048 B1 | 12/2005 |
| EP | 1042667 B1 | 6/2009 |
| JP | 2007114197 A | 5/2007 |
| JP | 2007524825 A | 8/2007 |
| JP | 2009533685 A | 9/2009 |
| WO | WO 9932881 A1 | 7/1999 |
| WO | WO 2006040200 A1 | 4/2006 |
| WO | WO 2006/070200 A1 | 7/2006 |
| WO | WO 2008/036516 A1 | 3/2008 |
| WO | WO 2008/040998 A2 | 4/2008 |
| WO | WO 2008/049075 A2 | 4/2008 |
| WO | 2009119118 A1 | 10/2009 |
| WO | WO 2010/049669 A1 | 5/2010 |
| WO | WO 2011/121292 A1 | 10/2011 |

OTHER PUBLICATIONS

U.S. Appl. No. 61/530,808, filed Sep. 2, 2011, McColl et al.
U.S. Appl. No. 61/581,087, filed Dec. 29, 2011, Malecha et al.
U.S. Appl. No. 61/581,089, filed Dec. 29, 2011, Malecha et al.
U.S. Appl. No. 61/581,099, filed Dec. 29, 2011, Malecha et al.
U.S. Appl. No. 61/581,100, filed Dec. 29, 2011, Smith et al.
U.S. Appl. No. 61/654,013, filed May 31, 2012, Malecha et al.
International Application No. PCT/GB2012/053276, PCT International Search Report and Written Opinion, 13 pages, dated May 3, 2013.
International Application No. PCT/GB2012/053277, PCT International Search Report and Written Opinion, 13 pages, dated May 3, 2013.
International Application No. PCT/GB2012/053279, PCT International Search Report and Written Opinion, 13 pages, dated May 3, 2013.
Patent Examination Report issued in related Australian Patent Application No. 2012327229, May 28, 2014, 5 pages.
Wegener, Joachim et al., "Electric Cell-Substrate Impedance Sensing (ECIS) as a Noninvasive Means to Monitor the Kinetics of Cell Spreading to Artificial Surfaces," Experimental Cell Research 259, 158-166 (2000) doi:10.1006/excr.2000.4919, available online at http://www.idealibrary.coml.

(56) References Cited

OTHER PUBLICATIONS

Kohma, Takuya et al., "Utilization of AC Impedance Measurements for Electrochemical Glucose Sensing Using Glucose Oxidase to Improve Detection Selectivity," Bull. Chem. Soc. Jpn. vol. 80, No. 1, 158-165 (2007).
Baskurt, Oguz K. et al., "Blood Rheology and Hemodynamics," Seminars in Thrombosis and Hemostasis, vol. 29, No. 5, 2003.
Nordbotten, Bernt, J. et al., "Methods for calculating phase angle from measured whole body bioimpedance modulus."
Wang, J. et al., "Electrochemical Impedance Biosensor for Glucose Detection Utilizing a Periplasmic *E. coli* Receptor Protein," Electrochemical and Solid-State Letters, 8 (8) H61-H64 (2005).
Caduff, A. et al., "First human experiments with a novel non-invasive, non-optical continuous glucose monitoring system," Biosensors and Bioelectronics 19 (2003) 209-217.
Guevara, Edgar et al., "Prediction of Glucose Concentration by Impedance Phase Measurements," CP1032, Medical Physics—Tenth Symposium of Medical Physics, 2008 American Institute of Physics 978-0-7354-0556, 259-261.
Park, J.-H. et al., "The correlation of the complex dielectric constant and blood glucose at low frequency," Biosensors and Bioelectronics 19 (2003) 321-324.
De Vries, P.M.J.M. et al., "Implications of the dielectrical behavior of human blood for continuous online measurement of haematocrit," Med. & Biol. Eng. & Comput. 1993, 31, 445-448.
"Annex A—Bioimpedance monitoring for physicians: an overview," pp. 131-178.
Koschinsky, T. et al., "Sensors for glucose monitoring: technical and clinical aspects," Diabetes Metab Res Rev 2001; 17: 113-123.
Marks, Vincent, "Blood glucose: its measurement and clinical importance," Clinica Chimica Acta 251 (1996) 3-17.
Shervedani, Reza Karimi et al., "A novel method for glucose determination based on electrochemical impedance spectroscopy using glucose oxidase self-assembled biosensor," Bioelectrochemistry 69 (2006) 201-208.
Tura, Andrea et al., "Non-invasive glucose monitoring: Assessment of technologies and devices according to quantitative criteria," Diabetes Research and Clinical Practice 77 (2007) 16-40.
Tierney, M.J. et al., "Clinical evaluation of the GlucoWatch® biographer: a continual, non-invasive glucose monitor for patients with diabetes," Biosensors & Bioelectronics 16 (2001) 621-629.
Tura, A. et al., "Impedance spectroscopy of solutions at physiological glucose concentrations," Biophysical Chemistry 129 (2007) 235-241.
International Preliminary Report on Patentability issued in related International Patent Application No. PCT/GB2012/053279, issued Jul. 1, 2004, 10 pages.
Patent Examination Report issued in related Australian Patent Application No. 2012340500, issued Aug. 4, 2014, 3 pages.
International Preliminary Report on Patentability issued in related International Patent Application No. PCT/GB2012/053277, issued Jul. 1, 2004, 11 pages.
International Preliminary Report on Patentability issued in related International Patent Application No. PCT/GB2012/053276, issued Jul. 1, 2004, 11 pages.
Patent Examination Report No. 1 issued in related Australian Patent Application No. 2015271939, dated Aug. 21, 2016, 3 pages.
English Translation of Search Report issued in related Chinese Patent Application No. 201280070976.5, dated Sep. 7, 2015, 2 pages.
First Office Action issued in related Chinese Patent Application No. 201280070976.5, dated Sep. 21, 2015, 24 pages.
Second Office Action issued in related Chinese Patent Application No. 201280070976.5, dated May 24, 2016, 7 pages.
Third Office Action issued in related Chinese Patent Application No. 201280070976.5, dated Nov. 2, 2016, 7 pages.
Examination Report issued in related European Patent Application No. 12810419.7, dated Jan. 27, 2015, 8 pages.
Notification of Reasons for Rejection issued in related Japanese Patent Application No. 2014-549535, dated Sep. 20, 2016, 8 pages.
English Translation of Search Report issued in related Taiwan Patent Application No. 101151340, dated Sep. 26, 2016, 1 page.

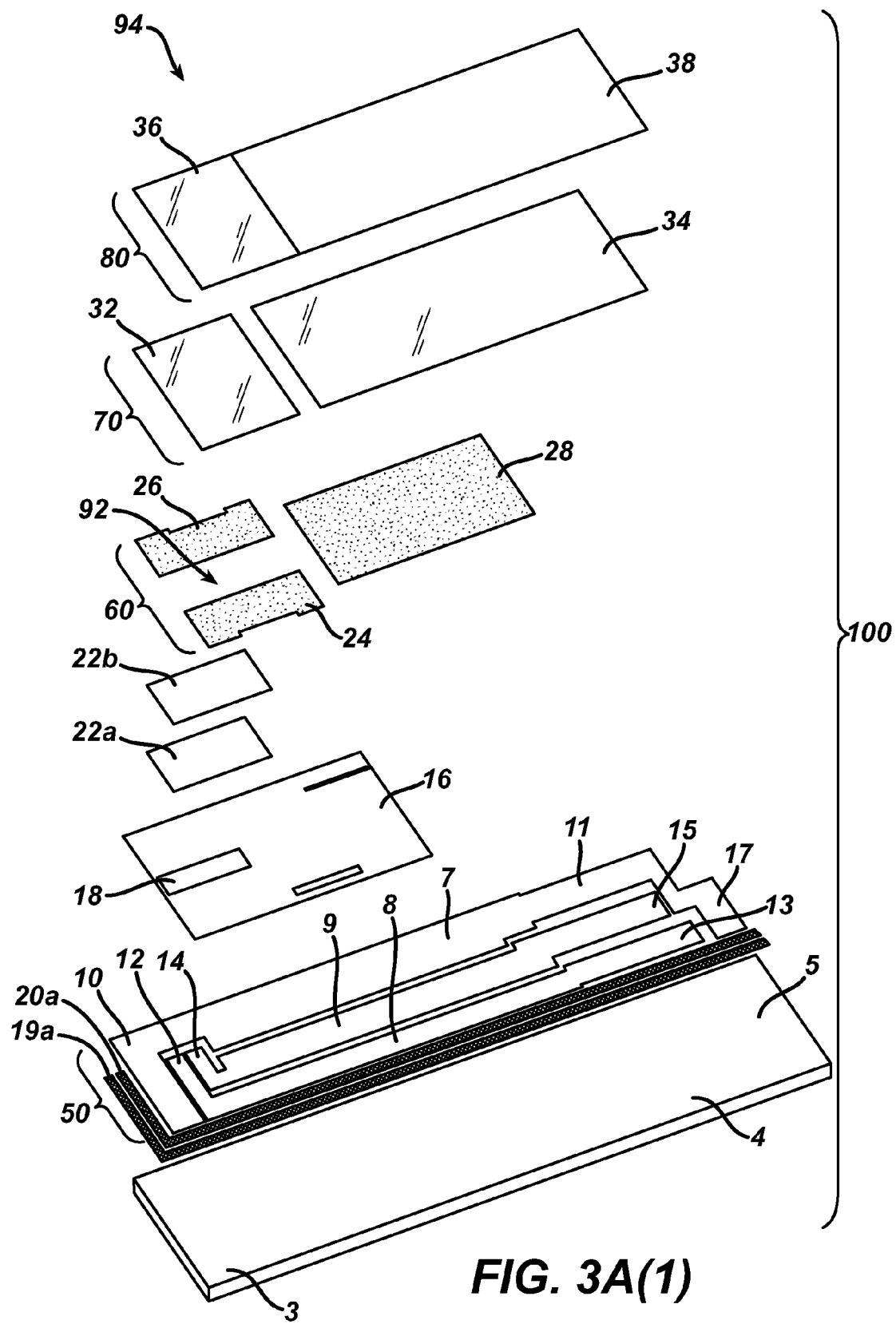
FIG. 3A(1)

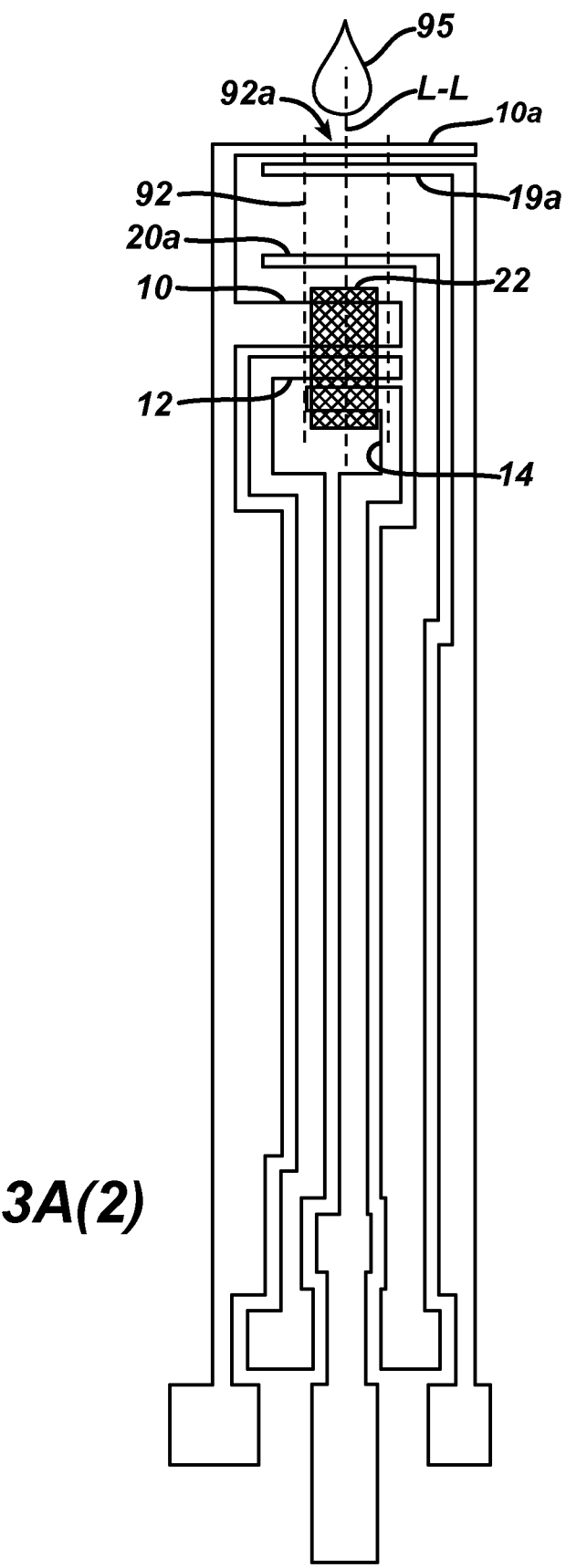
FIG. 3A(2)

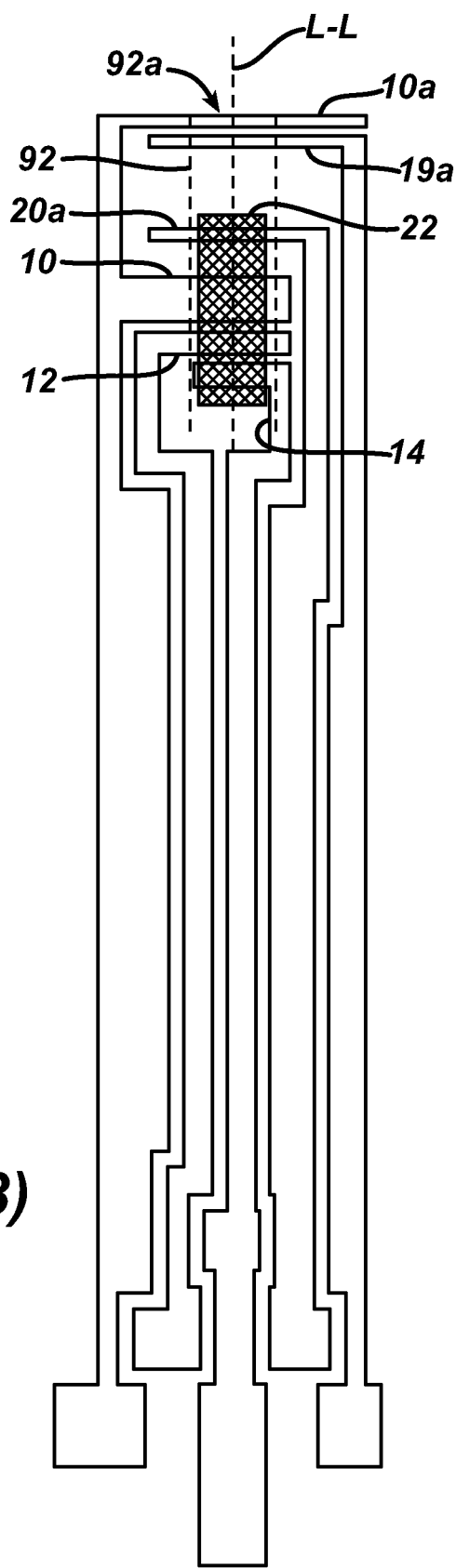
FIG. 3A(3)

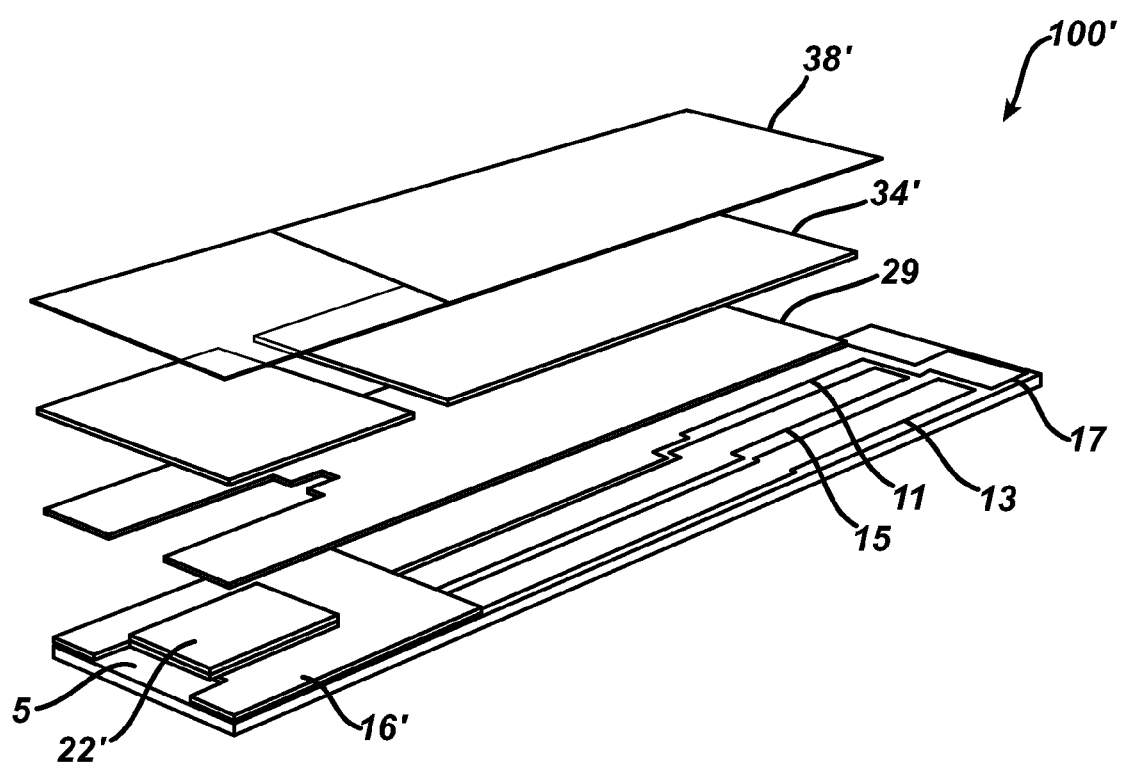
FIG. 3A(4)

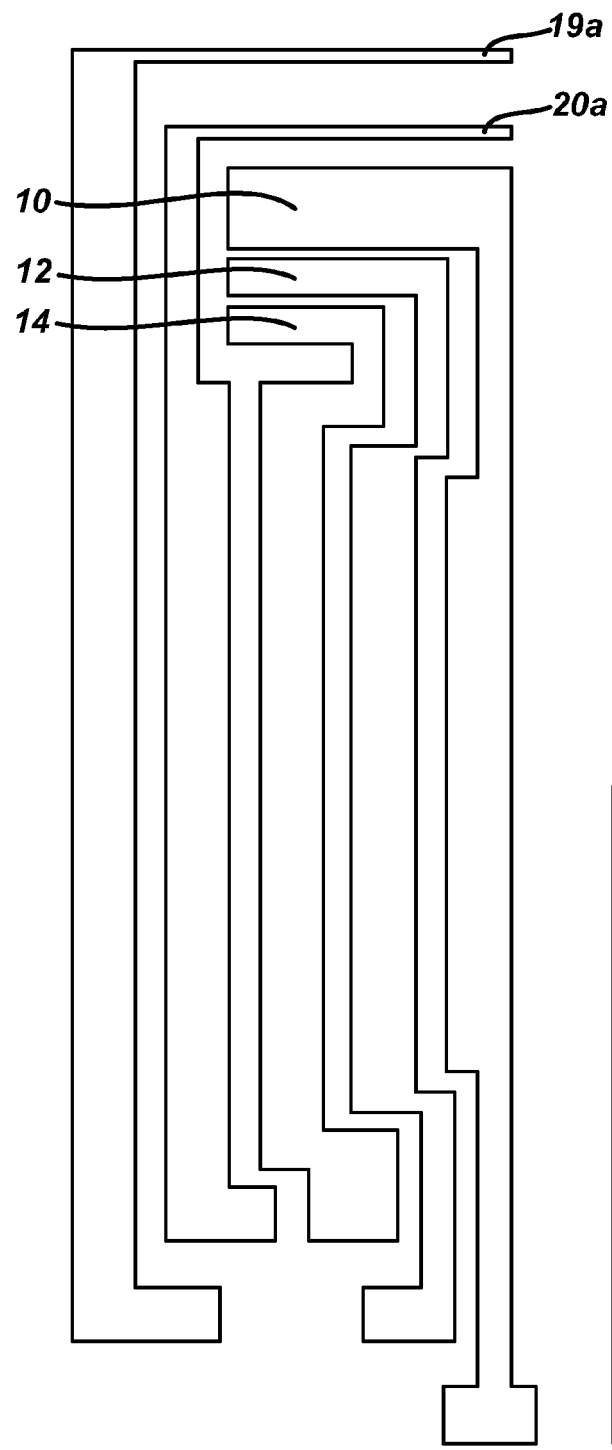
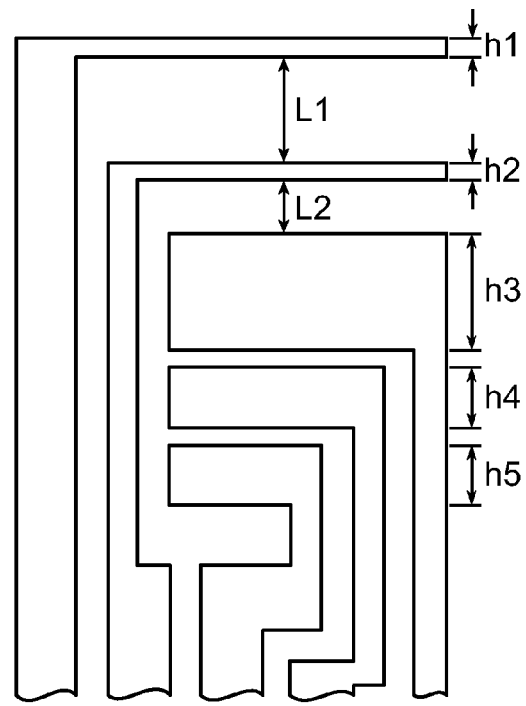
FIG. 3A(5)     FIG. 3A(6)

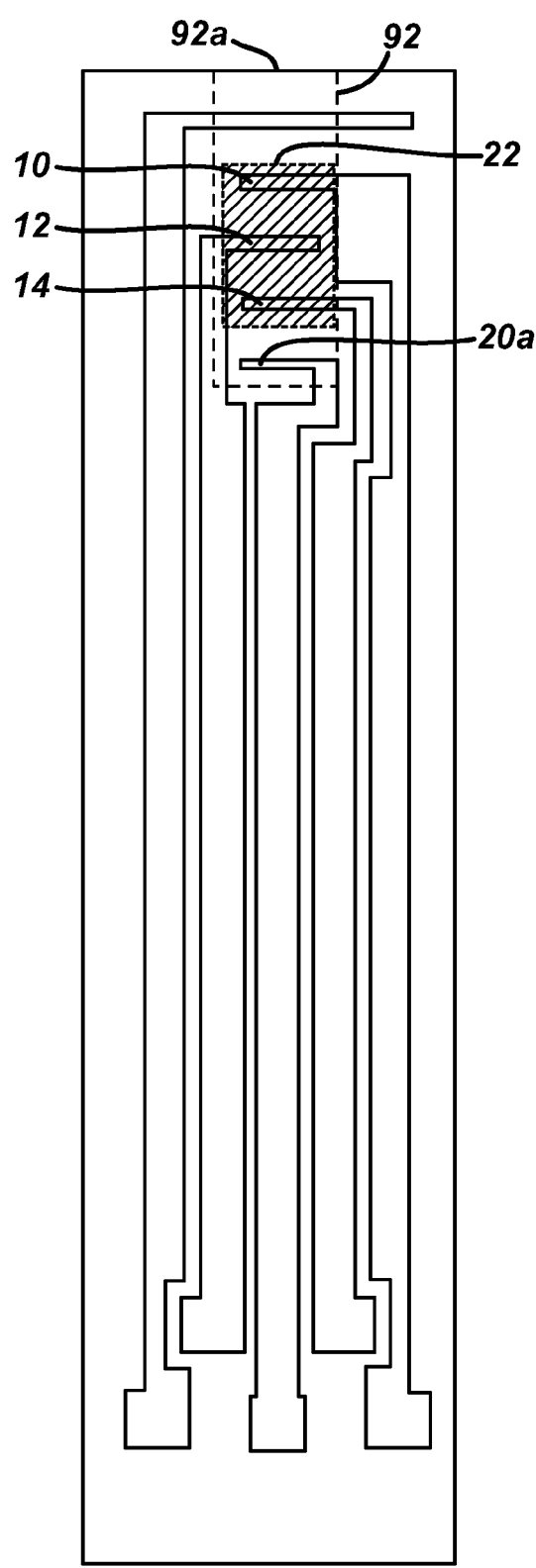
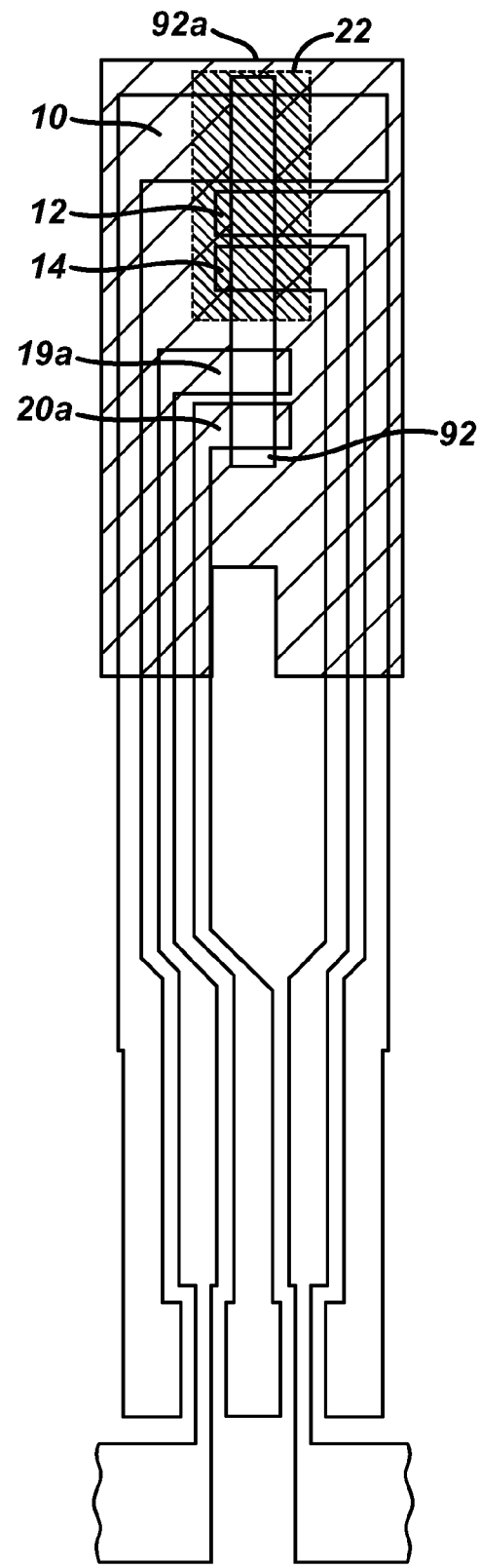
FIG. 3B
FIG. 3C

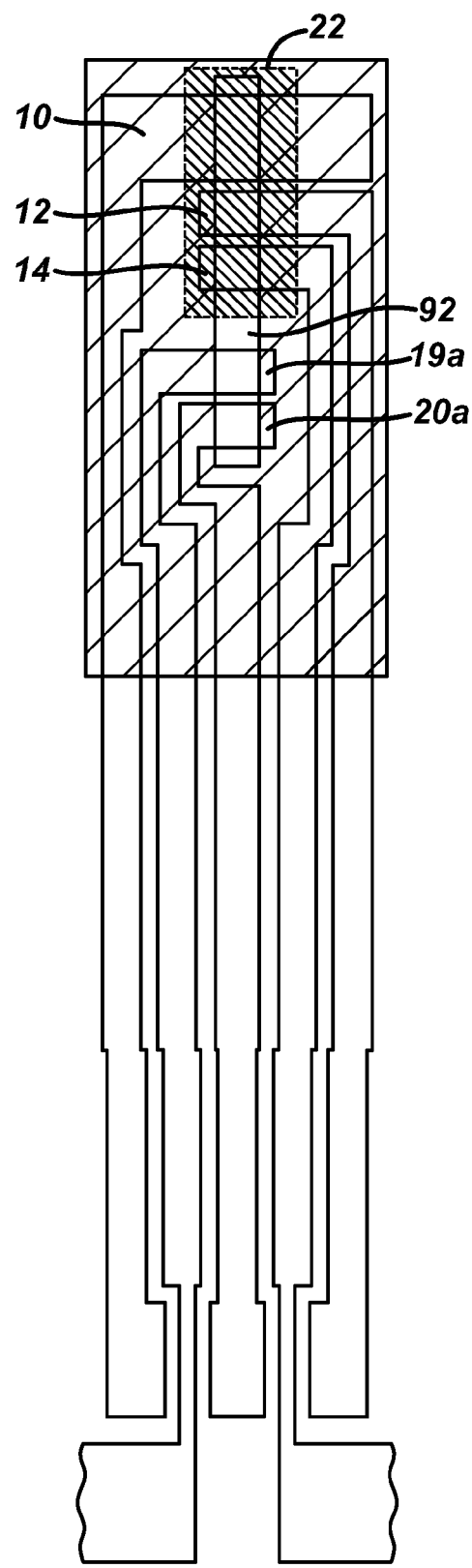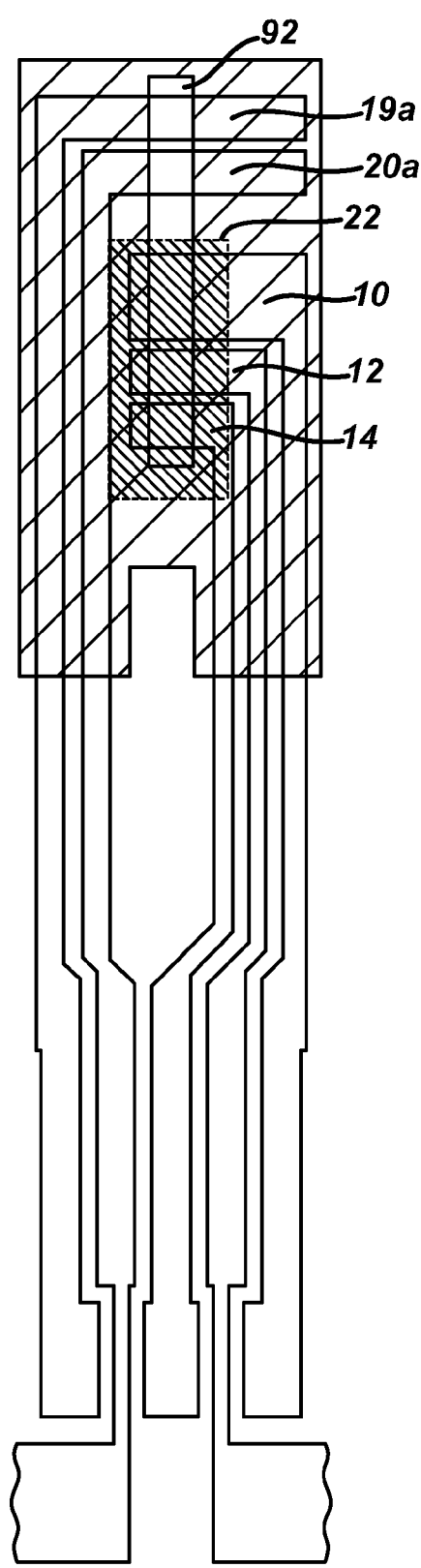
*FIG. 3D*  *FIG. 3E*

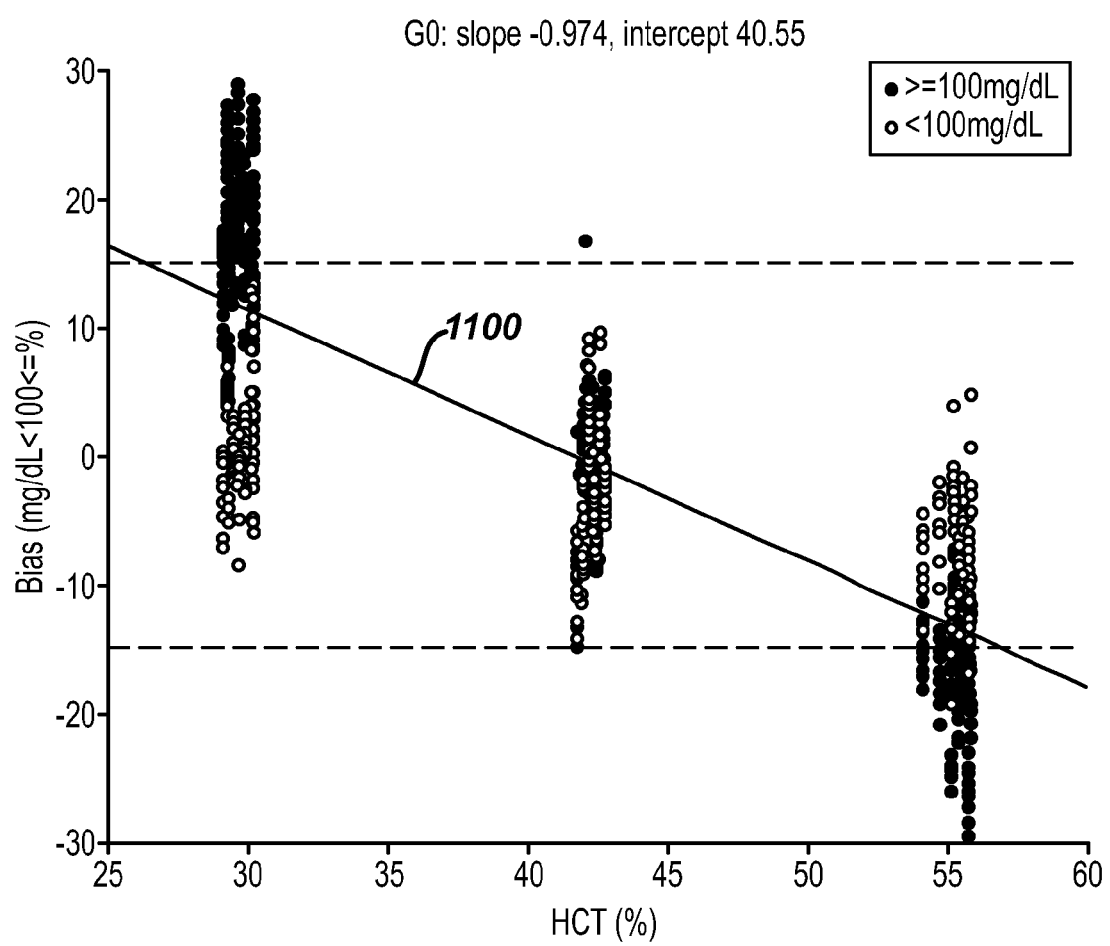
FIG. 8A _PRIOR ART_

ACCURATE ANALYTE MEASUREMENTS FOR ELECTROCHEMICAL TEST STRIP BASED ON MULTIPLE DISCRETE MEASUREMENTS DEFINED BY SENSED PHYSICAL CHARACTERISTIC(S) OF THE SAMPLE CONTAINING THE ANALYTE

PRIORITY

This National Stage application of International Application PCT/GB2012/053277 filed on Dec. 28, 2012 claims the benefits of priority of prior filed International Patent Application PCT/GB2012/053276; PCT/GB2012/053277; and PCT/GB2012/053279 on Dec. 28, 2012, in which each of the International Patent Applications claims benefits of priority to US Provisional Patent Application Ser. Nos. 61/581,087 ; 61/581,089 ; 61/581,099 ; and 61/581,100 , all filed on the same day of Dec. 29, 2011, and U.S. Provisional Patent Application Ser. No. 61/654,013 , filed on 31 May 2012, and in which all the prior patent applications are hereby incorporated by reference as if fully set forth herein this application.

BACKGROUND

Electrochemical glucose biosensors, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose biosensor are summarized below in Equations 1 and 2.

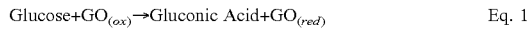

Glucose+$GO_{(ox)}$→Gluconic Acid+$GO_{(red)}$   Eq. 1

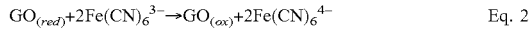

$GO_{(red)}+2Fe(CN)_6^{3-}$→$GO_{(ox)}+2Fe(CN)_6^{4-}$   Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ the oxidized (referred to as either oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test signal applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical biosensors. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there is less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, biosensors have been designed to incorporate meshes to remove red blood cells from the samples, or have included various compounds or formulations designed to increase the viscosity of red blood cells and attenuate the effect of low hematocrit on concentration determinations. Other test strips have included lysis agents and systems configured to determine hemoglobin concentration in an attempt to correct for the effects of hematocrit. Further, biosensors have been configured to measure hematocrit by measuring an electrical response of the fluid sample via alternating current signals or change in optical variations after irradiating the blood sample with light, or measuring hematocrit based on a function of sample chamber fill time. A common technique of the strategies involving detection of hematocrit is to use the measured hematocrit value to correct or change the measured analyte concentration, which technique is generally shown and described in the following respective US Patent Application Publication Nos. 2010/0283488; 2010/0206749; 2009/0236237; 2010/0276303; 2010/0206749; 2009/0223834; 2008/0083618; 2004/0079652; 2010/0283488; 2010/0206749; 2009/0194432; or U.S. Pat. Nos. 7,972,861 and 7,258,769, all of which are incorporated by reference herein to this application.

SUMMARY OF THE DISCLOSURE

Applicant has provided various embodiments of a technique to allow for improved glucose measurement using a relationship between sampling time point and hematocrit to derive or calculate a specific sampling time point that can be used to calculate a more accurate analyte concentration from an electrochemical biosensor. This newly provided technique does not rely on correction(s) or modification(s) to be made to an analyte measurement, thereby reducing test time while at the same time improving accuracy.

In a first aspect, a method of determining an analyte concentration from a physiological sample with a biosensor is provided. The biosensor has at least two electrodes and a reagent disposed on at least one electrode of the electrodes. The method can be achieved by: depositing a physiological sample on any one of the at least two electrodes to start an analyte test sequence; applying a first signal to the sample to derive a physical characteristic of the sample; driving a second signal to the sample for a first sampling time duration that overlaps with the test sequence to obtain a first transient signal output from the sample, the first transient signal correlated to both time and magnitude during the first sampling time duration; extracting a specific sampling time during the test sequence in the first sampling time duration based on the physical characteristic of the sample; defining a second sampling time duration based on the specific sampling time such that the second sampling time duration overlaps the first sampling time duration; obtaining from the first transient signal a second transient signal referenced with respect to the second sampling time duration; dividing the second transient signal into discrete intervals with respect to the second sampling time duration; deriving respective magnitudes of the second transient signal at discrete selected intervals in the second sampling time duration; and determining an analyte concentration based on respective magnitudes of the second transient signal at the discrete selected time intervals.

In a second aspect, a method of determining an analyte concentration from a physiological sample with a biosensor is provided. The biosensor has at least two electrodes and a reagent disposed on at least one electrode of the electrodes. The method can be achieved by: depositing a physiological sample on any one of the at least two electrodes to start an analyte test sequence; applying a first signal to the sample to derive a physical characteristic of the sample; driving a second signal to the sample for a first sampling time duration that overlaps with the test sequence to obtain a first transient signal output from the sample, the first transient signal correlated to both time and magnitude during the first sampling time duration; extracting a specific sampling time during the test sequence in the first sampling time duration based on the physical characteristic of the sample; obtaining from the first transient signal a second transient signal over a second sampling time duration; deriving respective magnitudes of the second transient signal at selected intervals in the second sampling time duration; and determining an analyte concentration based on respective magnitudes of the second transient signal at the selected time intervals.

In a third aspect, a method of determining an analyte concentration from a physiological sample with a biosensor is provided. The biosensor has at least two electrodes and a reagent disposed on at least one electrode of the electrodes. The method can be achieved by: depositing a physiological sample on any one of the at least two electrodes to start an analyte test sequence; applying a first signal to the sample to derive a physical characteristic of the sample; extracting a specific sampling time in a first sampling time duration; driving a second signal into the sample for the first sampling time duration; measuring or sampling a first transient signal output from the sample for the duration of the first sampling time duration; defining a specific range of time that includes the specific sampling time in the first sampling time duration; obtaining plural magnitudes of the first transient signal at respective discrete intervals within the specific range of time, and determining the analyte concentration based on the magnitudes of the first transient signal from the obtaining step.

In a fourth aspect, a method of determining an analyte concentration from a physiological sample with a biosensor is provided. The biosensor has at least two electrodes and a reagent disposed on at least one electrode of the electrodes. The method can be achieved by: depositing a physiological sample on any one of the at least two electrodes to start an analyte test sequence; applying a first signal to the sample to derive a physical characteristic of the sample; extracting a specific sampling time in a first sampling time duration; driving a second signal into the sample for the first sampling time duration; measuring or sampling a first transient signal output from the sample for the duration of the first sampling time duration; obtaining plural magnitudes of the first transient signal output at time intervals other than at about the specific sampling time; and deterring the analyte concentration based on the plural magnitudes of the first transient signal from the obtaining step.

In a fifth aspect, a method of determining an analyte concentration from a physiological sample with a biosensor is provided. The biosensor has at least two electrodes and a reagent disposed on at least one electrode of the electrodes. The method can be achieved by: depositing a physiological sample on any one of the at least two electrodes to start an analyte test sequence for each of a plurality of the biosensors; applying a first signal to the sample to derive a physical characteristic of the sample for each of a plurality of the biosensors; extracting a specific sampling time in a first sampling time duration for each of a plurality of the biosensors; driving a second signal into the sample for the first sampling time duration for each of a plurality of the biosensors; measuring or sampling a first transient signal output from the sample for the duration of the first sampling time duration for each of a plurality of the biosensors; defining a specific range of time that includes the specific sampling time in the first sampling time duration for each of a plurality of the biosensors; obtaining plural magnitudes of the first transient signal at respective discrete intervals within the specific range of time for each of a plurality of the biosensors, and determining the analyte concentration for each of the plurality of the biosensors based on the magnitudes of the first transient signal from the obtaining step such that an error between a plurality of analyte concentrations determined by the determining step for each of the plurality of the biosensors is less than ±15% as compared to referential value at each of 30%, 42%, and 55% hematocrits.

For these aspects, the following features may also be utilized in various combinations. For example, the specific range of time may include magnitudes of first transient signal measured before the specific sampling time; the step of extracting the specific sampling time may include calculating a defined specific sampling time in the first sampling time duration based on the physical characteristic of the sample; the calculating step for the defined specific sampling time may include utilizing an equation of the form:

$$\text{SpecificSamplingTime} = x_1 H^{x_2} + x_3$$

where
"SpecificSamplingTime" is designated as a time point from the start of the test sequence at which to sample the output signal of the biosensor,
H represents physical characteristic of the sample;
$x_1$ is about 4.3e5, or is equal to 4.3e5, or is equal to 4.3e5+/−10%, 5% or 1% of the numerical value provided hereof;

$x_2$ is about (−)3.9, or is equal to −3.9, or is equal to −3.9+/−10%, 5% or 1% of the numerical value provided hereof; and $x_3$ is about 4.8, or is equal to 4.8, or is equal to 4.8+/−10%, 5% or 1% of the numerical value provided herein.

With reference to these aspects, the following features may also be utilized in various combinations with these aspects. For example, the step of defining the second sampling time duration may include obtaining an absolute value of a difference between the defined specific sampling time and a predetermined time point to define a start time (T1) and an end time (T2) approximately equal to the specific sampling time point, and the first sampling time duration may include about 10 seconds or less from the step of depositing the sample; the step of obtaining further may include defining a second sampling time duration that overlaps the first sampling time duration and includes a portion of the first transient signal and its magnitudes with respect to time of the second sampling time duration, wherein the portion is designated as a second transient signal; the step of obtaining the second transient signal may include extracting from the first transient signal a portion of the first transient signal that is designated as a second transient signal that is within the second sampling time duration; the deriving of respective magnitudes of the second transient signal at discrete selected time intervals may include calculating a magnitude of the second transient signal during each selected time intervals; the dividing may include dividing the second transient signal into at least 22 intervals in sequence starting from interval one at about the start time to interval twenty-two at about the end time.

As with other features, the following features may also be utilized in combination with these aforementioned aspects. For example, the determination of analyte concentration may be obtained by utilizing an equation of the form:

$$G = \frac{\left(\frac{|I_3|}{|I_4|}\right)^{x_1} \times \left(\frac{|I_2| + x_4|I_5| - x_5|I_1|}{|I_2| + x_4|I_5|}|I_5|\right) - x_2}{x_3}$$

where:
G is representative of analyte concentration;
$I_1 \approx$ magnitude of second transient signal at interval 17, or $I_1 =$ magnitude of second transient signal at interval 17, or $I_1 =$ magnitude of second transient signal at interval 17, +/−10%, 5% or 1%;
$I_2 \approx$ magnitude of second transient signal at interval 13, or $I_2 =$ magnitude of second transient signal at interval 13, or $I_2 =$ magnitude of second transient signal at interval 13, +/−10%, 5% or 1%;
$I_3 \approx$ magnitude of second transient signal at interval 5, or $I_3 =$ magnitude of second transient signal at interval 5, or $I_3 =$ magnitude of second transient signal at interval 5, +/−10%, 5% or 1%;
$I_4 \approx$ magnitude of second transient signal at interval 3, $I_4 =$ magnitude of second transient signal at interval 3, or $I_4 =$ magnitude of second transient signal at interval 3, +/−10%, 5% or 1%;
$I_5 \approx$ magnitude of second transient signal at interval 22; $I_5 =$ magnitude of second transient signal at interval 22, or $I_5 =$ magnitude of second transient signal at interval 22, +/−10%, 5% or 1%
$x_1 \approx 0.75$, $x_1 = 0.75$, or $x_1 = 0.75$+/−10%, 5% or 1%;
$x_2 \approx 337.27$, $x_2 = 337.27$, or $x_2 = 337.27$+/−10%, 5% or 1%;
$x_3 \approx (-)16.81$, $x_3 = (-)16.81$, or $x_3 = (-)16.81$+/−10%, 5% or 1%;
$x_4 \approx 1.41$, $x_4 = 1.41$, or $x_4 = 1.41$+/−10%, 5% or 1%; and
$x_5 \approx 2.67$, $x_5 = 2.67$, or $x_5 = 2.67$+/−10%, 5% or 1%;
or the determination of analyte concentration may be obtained by utilizing an equation of the form:

$$G = \frac{x_1(|I_1|)^{\left(x_2 - \frac{x_3}{|I_2|}\right)} - x_4}{x_5}$$

where:
G is representative of analyte concentration;
$I_1 \approx$ magnitude of second transient signal at interval 11, $I_1 =$ magnitude of second transient signal at interval 11, or $I_1 =$ magnitude of second transient signal at interval 11, +/−10%, 5% or 1%;
$I_2 \approx$ magnitude of second transient signal at interval 7, $I_2 =$ magnitude of second transient signal at interval 7, or $I_2 =$ magnitude of second transient signal at interval 7, +/−10%, 5% or 1%;
$x_1 \approx 0.59$, $x_1 = 0.59$, or $x_1 = 0.59$+/−10%, 5% or 1%;
$x_2 \approx 2.51$, $x_2 = 2.51$, or $x_2 = 2.51$+/−10%, 5% or 1%;
$x_3 \approx (-)12.74$, $x_3 = (-)12.74$, or $x_3 = (-)12.74$+/−10%, 5% or 1%;
$x_4 \approx (-)188.31$, $x_4 = (-)188.31$, or $x_4 = (-)188.31$+/−10%, 5% or 1%; and
$x_5 \approx 9.2$, $x_5 = 9.2$, or $x_5 = 9.2$+/−10%, 5% or 1%;
or the determination of analyte concentration may be obtained by utilizing an equation of the form:

$$G = \frac{x_1 \ln\left(x_2 \frac{|I_1|}{|I_2|}\right)^{x_3} |I_3|^{x_4} - x_5}{x_6}$$

where
G is representative of analyte concentration;
$I_1 \approx$ magnitude of second transient signal at interval 20, $I_1 =$ magnitude of second transient signal at interval 20, or $I_1 =$ magnitude of second transient signal at interval 20, +/−10%, 5% or 1%;
$I_2 \approx$ magnitude of second transient signal at interval 22, $I_2 =$ magnitude of second transient signal at interval 22, or $I_2 =$ magnitude of second transient signal at interval 22, +/−10%, 5% or 1%;
$I_3 \approx$ magnitude of second transient signal at interval 19, $I_3 =$ magnitude of second transient signal at interval 19, or $I_3 =$ magnitude of second transient signal at interval 19, +/−10%, 5% or 1%;
$x_1 \approx 20.15$, $x_1 = 20.15$, or $x_1 = 20.15$+/−10%, 5% or 1%;
$x_2 \approx 1.0446$, $x_2 = 1.0446$, or $x_2 = 1.0446$+/−10%, 5% or 1%;
$x_3 \approx 0.95$, $x_3 = 0.95$, or $x_3 = 0.95$+/−10%, 5% or 1%;
$x_4 \approx 1.39$, $x_4 = 1.39$, or $x_4 = 1.39$+/−10%, 5% or 1%;
$x_5$ (−)0.71, $x_5 = (-)0.71$, or $x_5 = (-)0.71$+/−10%, 5% or 1%; and
$x_6 \approx 0.11$, $x_6 = 0.11$, or $x_6 = 0.11$+/−10%, 5% or 1%;
or the determination of analyte concentration may be obtained by utilizing an equation of the form:

$$G = \frac{x_3 \left|\frac{I_1}{I_2}\right|^{\left(x_1 - x_2 \left|\frac{I_3}{I_4}\right|\right)} \times |I_5| - x_5}{x_4}$$

where:
G is representative of analyte concentration;
$I_1 \approx$ magnitude of second transient signal at interval 5, $I_1 =$ magnitude of second transient signal at interval 5, or $I_1 =$ magnitude of second transient signal at interval 5, +/−10%, 5% or 1%;
$I_2 \approx$ magnitude of second transient signal at interval 1, $I_2 =$ magnitude of second transient signal at interval 1, or $I_2 =$ magnitude of second transient signal at interval 1, +/−10%, 5% or 1%;
$I_3 \approx$ magnitude of second transient signal at interval 2, $I_3 =$ magnitude of second transient signal at interval 2, or $I_3 =$ magnitude of second transient signal at interval 2, +/−10%, 5% or 1%;
$I_4 \approx$ magnitude of second transient signal at interval 10, $I_4 =$ magnitude of second transient signal at interval 10, or $I_4 =$ magnitude of second transient signal at interval 10, +/−10%, 5% or 1%;
$I_5 \approx$ magnitude of second transient signal at interval 22, $I_5 =$ magnitude of second transient signal at interval 22, $I_5 =$ magnitude of second transient signal at interval 22, +/−10%, 5% or 1%;
$x_1 \approx 0.70$, $x_1 = 0.70$, or $x_1 = 0.70$+/−10%, 5% or 1%,
$x_2 \approx 0.49$, $x_2 = 0.49$, or $x_2 = 0.49$+/−10%, 5% or 1%,
$x_3 \approx 28.59$, $x_3 = 28.59$, or $x_3 = 28.59$+/−10%, 5% or 1%,
$x_4 \approx 0.7$, $x_4 = 0.7$, or $x_4 = 0.7$+/−10%, 5% or 1%, and
$x_5 \approx 15.51$, $x_5 = 15.51$, or $x_5 = 15.51$+/−10%, 5% or 1%;
or the determination of analyte concentration may be obtained by utilizing an equation of the form:

$$G = \frac{\left(\left|\frac{I_1}{I_2}\right|^{x_1} \times \frac{x_2|I_3|^2 + x_3|I_3| + x_4}{x_5|I_4| + x_6}\right) - x_7}{x_8}$$

where:
G is representative of analyte concentration;
$I_1 \approx$ magnitude of second transient signal at interval 19, $I_1 =$ magnitude of second transient signal at interval 19, or $I_1 =$ magnitude of second transient signal at interval 19, +/−10%, 5% or 1%;
$I_2 \approx$ magnitude of second transient signal at interval 16, $I_2 =$ magnitude of second transient signal at interval 16, $I_2 =$ magnitude of second transient signal at interval 16, +/−10%, 5% or 1%;
$I_3 \approx$ magnitude of second transient signal at interval 11, $I_3 =$ magnitude of second transient signal at interval 11, or $I_3 =$ magnitude of second transient signal at interval 11, +/−10%, 5% or 1%;
$I_4 \approx$ magnitude of second transient signal at interval 5, $I_4 =$ magnitude of second transient signal at interval 5, or $I_4 =$ magnitude of second transient signal at interval 5, +/−10%, 5% or 1%;
$x_1 \approx (-)1.68$, $x_1 = (-)1.68$, or $x_1 = (-)1.68$+/−10%, 5% or 1%;
$x_2 \approx 0.95$, $x_2 = 0.95$, or $x_2 = 0.95$+/−10%, 5% or 1%;
$x_3 \approx (-)4.97$, $x_3 = (-)4.97$, or $x_3 = (-)4.97$+/−10%, 5% or 1%;
$x_4 \approx 6.29$, $x_4 = 6.29$, or $x_4 = 6.29$+/−10%, 5% or 1%;
$x_5 \approx 3.08$, $x_5 = 3.08$, or $x_5 = 3.08$+/−10%, 5% or 1%;
$x_6 \approx (-)5.84$, $x_6 = (-)5.84$, or $x_6 = (-)5.84$+/−10%, 5% or 1%;
$x_7 \approx (-)0.47$, $x_7 = (-)0.47$, or $x_7 = (-)0.47$+/−10%, 5% or 1%;
$x_8 \approx 0.01$, $x_8 = 0.01$, or $x_8 = 0.01$+/−10%, 5% or 1%;

or the determination of analyte concentration may be obtained by utilizing an equation of the form:

$$G = \frac{\left(\left|\frac{I_1}{I_2}\right|^{x_1} \times \frac{x_2|I_3|^3 + x_3|I_3|^2 + x_4|I_3| + x_5}{x_6|I_4|^2 + x_7|I_4| + x_8}\right) - x_9}{x_{10}}$$

where:
G is representative of analyte concentration;
$I_1 \approx$ magnitude of second transient signal at interval 16, $I_1 =$ magnitude of second transient signal at interval 16, or $I_1 =$ magnitude of second transient signal at interval 16, +/−10%, 5% or 1%;
$I_2 \approx$ magnitude of second transient signal at interval 5, $I_2 =$ magnitude of second transient signal at interval 5, or $I_2 =$ magnitude of second transient signal at interval 5, +/−10%, 5% or 1%;
$I_3 \approx$ magnitude of second transient signal at interval 12, $I_3 =$ magnitude of second transient signal at interval 12, or $I_3 =$ magnitude of second transient signal at interval 12, +/−10%, 5% or 1%;
$I_4 \approx$ magnitude of second transient signal at interval 14, $I_4 =$ magnitude of second transient signal at interval 14, or $I_4 =$ magnitude of second transient signal at interval 14, +/−10%, 5% or 1%;
$x_1 \approx 1.18$, $x_1 = 1.18$, or $x_1 = 1.18$+/−10%, 5% or 1%;
$x_2 \approx 0.97$, $x_2 = 0.97$, or $x_2 = 0.97$+/−10%, 5% or 1%;
$x_3 \approx (-)11.32$, $x_3 = (-)11.32$, or $x_3 = (-)11.32$+/−10%, 5% or 1%;
$x_4 \approx 38.76$, $x_4 = 38.76$, or $x_4 = 38.76$+/−10%, 5% or 1%;
$x_5 \approx (-)39.32$, $x_5 = (-)39.32$, or $x_5 = (-)39.32$+/−10%, 5% or 1%;
$x_6 \approx 0.0928$, $x_6 = 0.0928$, or $x_6 = 0.0928$+/−10%, 5% or 1%;
$x_7 \approx (-)0.85$, $x_7 = (-)0.85$, or $x_7 = (-)0.85$+/−10%, 5% or 1%;
$x_8 \approx 1.75$, $x_8 = 1.75$, or $x_8 = 1.75$+/−10%, 5% or 1%;
$x_9 \approx (-)9.38$, $x_9 = (-)9.38$, or $x_9 = (-)9.38$+/−10%, 5% or 1%; and
$x_{10} \approx 0.25$, $x_{10} = 0.25$, or $x_{10} = 0.25$+/−10%, 5% or 1%.

In any of these features, the magnitude of the second transient signal at each of the plurality of discrete intervals may include an average magnitude of the signal sampled throughout each interval; the applying of the first signal and the driving of the second signal may be in sequential order; the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature, or density of the sample; the directing may include driving first and second alternating signal at different respective frequencies in which a first frequency may include a frequency than the second frequency; the first frequency may be at least one order of magnitude lower than the second frequency; the first frequency may include any frequency in the range of about 10 kHz to about 250 kHz, or about 10 kHz to about 90 kHz; the obtaining may include extracting from the first transient signal a second transient signal referenced with respect to the second sampling time duration; the obtaining may include removing signals from the first transient signals that are outside of the second sampling time duration to leave the second transient signal within the second sampling time duration; the deriving may include storing magnitudes of the second transient signal for each discrete intervals in the second sampling time duration.

In a fifth aspect, an analyte measurement system is provided that includes a biosensor and an analyte meter. The biosensor includes a substrate, a plurality of electrodes connected to respective electrode connectors. The analyte meter includes a housing, a biosensor port connector configured to connect to the respective electrode connectors of the biosensor. The meter also includes a microprocessor in electrical communication with the biosensor port connector to apply electrical signals or sense electrical signals from the plurality of electrodes during a test sequence. The microprocessor is configured to: (a) apply a first signal to the plurality of electrodes so that a physical characteristic of the sample is derived to provide a specific sampling time, (b) apply a second signal to the plurality of electrodes, (c) measure a first transient output signal from the plurality of electrodes; (d) extract a second transient output signal from the first output signal; (e) determine a magnitude of the second transient output signal over a plurality of discrete time intervals; and (f) calculate the analyte concentration from the magnitudes of the second transient output signal at selected intervals of the plurality of discrete time intervals.

In a sixth aspect, an analyte measurement system is provided that includes a test strip and an analyte meter. The test strip includes a substrate, a plurality of electrodes disposed on the substrate and connected to respective electrode connectors. The analyte meter includes a housing, a test strip port connector configured to connect to the respective electrode connectors of the test strip. The meter also includes a microprocessor in electrical communication with the test strip port connector to apply electrical signals or sense electrical signals from the plurality of electrodes during a test sequence. The microprocessor in electrical communication with the test strip port connector to apply electrical signals or sense electrical signals from the plurality of electrodes during a test sequence, the microprocessor is configured to: (a) apply a first signal to the plurality of electrodes so that a physical characteristic of the sample is derived to provide a specific sampling time, (b) apply a second signal to the plurality of electrodes, (c) measure a first transient output signal from the plurality of electrodes; (d) extract a second transient output signal from the first output signal; (e) determine a magnitude of the second transient output signal over a plurality of discrete time intervals; and (f) calculate the analyte concentration from the magnitudes of the second transient output signal at selected intervals of the plurality of discrete time intervals to annunciate the analyte concentration within about 10 seconds of a start of the test sequence.

In a seventh aspect, an analyte meter is provided that includes a housing and a test strip port connector configured to connect to respective electrode connectors of a test strip. The meter also includes a microprocessor in electrical communication with the test strip port connector to apply electrical signals or sense electrical signals from a plurality of electrodes of the test strip during a test sequence. The microprocessor is configured to: (a) apply a first signal to the plurality of electrodes so that a physical characteristic of the sample is derived to provide a specific sampling time, (b) apply a second signal to the plurality of electrodes, (c) measure a first transient output signal from the plurality of electrodes; (d) extract a second transient output signal from the first output signal; (e) determine a magnitude of the second transient output signal over a plurality of discrete time intervals; and (f) calculate the analyte concentration from the magnitudes of the second transient output signal at selected intervals of the plurality of discrete time intervals.

In any of the fifth, sixth and seventh aspects, the following features can also be utilized in combination with the aforementioned aspects. For example, the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may comprise two electrodes to measure the physical characteristic and the analyte concentration; the plurality of electrodes may include two electrodes to measure the physical characteristic and the analyte concentration; all of the electrodes may be disposed on the same plane defined by the substrate; a reagent may be disposed proximate the at least two other electrodes and no reagent disposed on the at least two electrodes; the plurality of discrete time intervals may comprise at least 22 discrete time intervals, the specific sampling time may be calculated using an equation of the form:

$$\text{SpecificSamplingTime} = x_1 H^{x_2} + x_3$$

where
"SpecificSamplingTime" is designated as a time point from the start of the test sequence at which to sample the output signal of the biosensor,
H represents physical characteristic of the sample;
$x_1$ represents about 4.3e5, or is equal to 4.3e5, or is equal to 4.3e5+/−10%, 5% or 1% of the numerical value provided hereof;
$x_2$ represents about (−)3.9, or is equal to −3.9, or is equal to −3.9+/−10%, 5% or 1% of the numerical value provided hereof; and
$x_3$ represents about 4.8, or is equal to −3.9, or is equal to −3.9+/−10%, 5% or 1% of the numerical value provided hereof.

As indicated earlier, other features can also be used with the fifth, sixth and seventh aspects. For example, the microprocessor may calculate the analyte concentration with an equation of the form:

$$G = \frac{\left(\left|\frac{I_3}{I_4}\right|\right)^{x_1} \times \left(\frac{|I_2| + x_4|I_5| - x_5|I_1|}{|I_2| + x_4|I_5|}|I_5|\right) - x_2}{x_3}$$

where:
G is representative of analyte concentration;
$I_1 \approx$ magnitude of second transient signal at interval 17, or $I_1$=magnitude of second transient signal at interval 17, or $I_1$=magnitude of second transient signal at interval 17, +/−10%, 5% or 1%;
$I_2 \approx$ magnitude of second transient signal at interval 13, or $I_2$=magnitude of second transient signal at interval 13, or $I_2$=magnitude of second transient signal at interval 13, +/−10%, 5% or 1%;
$I_3 \approx$ magnitude of second transient signal at interval 5, or $I_3$=magnitude of second transient signal at interval 5, or $I_3$=magnitude of second transient signal at interval 5, +/−10%, 5% or 1%;

I$_4$≈magnitude of second transient signal at interval 3, I$_4$=magnitude of second transient signal at interval 3, or I$_4$=magnitude of second transient signal at interval 3, +/−10%, 5% or 1%;

I$_5$≈magnitude of second transient signal at interval 22; I$_5$=magnitude of second transient signal at interval 22, or I$_5$=magnitude of second transient signal at interval 22, +/−10%, 5% or 1% x$_1$≈0.75, x$_1$=0.75, or x$_1$=0.75+/−10%, 5% or 1%;
x$_2$≈337.27, x$_2$=337.27, or x$_2$=337.27+/−10%, 5% or 1%;
x$_3$≈(−)16.81, x$_3$=(−)16.81, or x$_3$=(−)16.81+/−10%, 5% or 1%;
x$_4$≈1.41, x$_4$=1.41, or x$_4$=1.41+/−10%, 5% or 1%; and
x$_5$≈2.67, x$_5$=2.67, or x$_5$=2.67+/−10%, 5% or 1%;

As another example, the microprocessor may also calculate the analyte concentration with an equation of the form:

$$G = \frac{x_1 (|I_1|)^{\left(x_2 - \frac{x_3}{|I_2|}\right)} - x_4}{x_5}$$

where:
G is representative of analyte concentration;
I$_1$≈magnitude of second transient signal at interval 11, I$_1$=magnitude of second transient signal at interval 11, or I$_1$=magnitude of second transient signal at interval 11, +/−10%, 5% or 1%;
I$_2$≈magnitude of second transient signal at interval 7, I$_2$=magnitude of second transient signal at interval 7, or I$_2$=magnitude of second transient signal at interval 7, +/−10%, 5% or 1%;
x$_1$≈0.59, x$_1$=0.59, or x$_1$=0.59+/−10%, 5% or 1%;
x$_2$≈2.51, x$_2$=2.51, or x$_2$=2.51+/−10%, 5% or 1%;
x$_3$≈(−)12.74, x$_3$=(−)12.74, or x$_3$=(−)12.74+/−10%, 5% or 1%;
x$_4$≈(−)188.31, x$_4$=(−)188.31, or x$_4$=(−)188.31+/−10%, 5% or 1%; and
x$_5$≈9.2, x$_5$=9.2, or x$_5$=9.2+/−10%, 5% or 1%

In an alternative example, the microprocessor may calculate the analyte concentration with an equation of the form:

$$G = \frac{x_1 \ln\left(x_2 \left|\frac{I_1}{I_2}\right|\right)^{x_3} |I_3|^{x_4} - x_5}{x_6}$$

where
G is representative of analyte concentration;
I$_1$≈magnitude of second transient signal at interval 20, I$_1$=magnitude of second transient signal at interval 20, or I$_1$=magnitude of second transient signal at interval 20, +/−10%, 5% or 1%;
I$_2$≈magnitude of second transient signal at interval 22, I$_2$=magnitude of second transient signal at interval 22, or I$_2$=magnitude of second transient signal at interval 22, +/−10%, 5% or 1%;
I$_3$≈magnitude of second transient signal at interval 19, I$_3$=magnitude of second transient signal at interval 19, or I$_3$=magnitude of second transient signal at interval 19, +/−10%, 5% or 1%;
x$_1$≈20.15, x$_1$=20.15, or x$_1$=20.15+/−10%, 5% or 1%;
x$_2$≈1.0446, x$_2$=1.0446, or x$_2$=1.0446+/−10%, 5% or 1%;
x$_3$≈0.95, x$_3$=0.95, or x$_3$=0.95+/−10%, 5% or 1%;
x$_4$≈1.39, x$_4$=1.39, or x$_4$=1.39+/−10%, 5% or 1%;
x$_5$≈(−)0.71, x$_5$=(−)0.71, or x$_5$=(−)0.71+/−10%, 5% or 1%; and
x$_6$≈0.11, x$_6$=0.11, or x$_6$=0.11+/−10%, 5% or 1%;

Alternatively, the microprocessor may calculate the analyte concentration with an equation of the form:

$$G = \frac{x_3 \left|\frac{I_1}{I_2}\right|^{\left(x_1 - x_2 \left|\frac{I_3}{I_4}\right|\right)} \times |I_5| - x_5}{x_4}$$

where:
G is representative of analyte concentration
I$_1$≈magnitude of second transient signal at interval 5, I$_1$=magnitude of second transient signal at interval 5, or I$_1$=magnitude of second transient signal at interval 5, +/−10%, 5% or 1%;
I$_2$≈magnitude of second transient signal at interval 1, I$_2$=magnitude of second transient signal at interval 1, or I$_2$=magnitude of second transient signal at interval 1, +/−10%, 5% or 1%;
I$_3$≈magnitude of second transient signal at interval 2, I$_3$=magnitude of second transient signal at interval 2, or I$_3$=magnitude of second transient signal at interval 2, +/−10%, 5% or 1%;
I$_4$≈magnitude of second transient signal at interval 10, I$_4$=magnitude of second transient signal at interval 10, or I$_4$=magnitude of second transient signal at interval 10, +/−10%, 5% or 1%;
I$_5$≈magnitude of second transient signal at interval 22, I$_5$=magnitude of second transient signal at interval 22, I$_5$=magnitude of second transient signal at interval 22, +/−10%, 5% or 1%;
x$_1$≈0.70, x$_1$=0.70, or x$_1$=0.70+/−10%, 5% or 1%,
x$_2$≈0.49, x$_2$=0.49, or x$_2$=0.49+/−10%, 5% or 1%,
x$_3$≈28.59, x$_3$=28.59, or x$_3$=28.59+/−10%, 5% or 1%,
x$_4$≈0.7, x$_4$=0.7, or x$_4$=0.7+/−10%, 5% or 1%, and
x$_5$≈15.51, x$_5$=15.51, or x$_5$=15.51+/−10%, 5% or 1%;
or the microprocessor calculates the analyte concentration with an equation of the form:

$$G = \frac{\left(\left|\frac{I_1}{I_2}\right|^{x_1} \times \frac{x_2 |I_3|^2 + x_3 |I_3| + x_4}{x_5 |I_4| + x_6}\right) - x_7}{x_8}$$

where:
G is representative of analyte concentration;
I$_1$≈magnitude of second transient signal at interval 19, I$_1$=magnitude of second transient signal at interval 19, or I$_1$=magnitude of second transient signal at interval 19, +/−10%, 5% or 1%;
I$_2$≈magnitude of second transient signal at interval 16, I$_2$=magnitude of second transient signal at interval 16, I$_2$=magnitude of second transient signal at interval 16, +/−10%, 5% or 1%;
I$_3$≈magnitude of second transient signal at interval 11, I$_1$=magnitude of second transient signal at interval 11, or I$_3$=magnitude of second transient signal at interval 11, +/−10%, 5% or 1%;
I$_4$≈magnitude of second transient signal at interval 5, I$_4$=magnitude of second transient signal at interval 5, or I$_4$=magnitude of second transient signal at interval 5, +/−10%, 5% or 1%;

$x_1 \approx (-)1.68$, $x_1 = (-)1.68$, or $x_1 = (-)1.68 +/- 10\%$, 5% or 1%;

$x_2 \approx 0.95$, $x_2 = 0.95$, or $x_2 = 0.95 +/- 10\%$, 5% or 1%;

$x_3 \approx (-)4.97$, $x_3 = (-)4.97$, or $x_3 = (-)4.97 +/- 10\%$, 5% or 1%;

$x_4 \approx 6.29$, $x_4 = 6.29$, or $x_4 = 6.29 +/- 10\%$, 5% or 1%;

$x_5 \approx 3.08$, $x_5 = 3.08$, or $x_5 = 3.08 +/- 10\%$, 5% or 1%;

$x_6 \approx (-)5.84$, $x_6 = (-)5.84$, or $x_6 = (-)5.84 +/- 10\%$, 5% or 1%;

$x_7 \approx (-)0.47$, $x_7 = (-)0.47$, or $x_7 = (-)0.47 +/- 10\%$, 5% or 1%;

$x_8 \approx 0.01$, $x_8 = 0.01$, or $x_8 = 0.01 +/- 10\%$, 5% or 1%;

or the microprocessor calculates the analyte concentration with an equation of the form:

$$G = \frac{\left(\left|\frac{I_1}{I_2}\right|^{x_1} \times \frac{x_2 |I_3|^3 + x_3 |I_3|^2 + x_4 |I_3| + x_5}{x_6 |I_4|^2 + x_7 |I_4| + x_8}\right) - x_9}{x_{10}}$$

where:

G is representative of analyte concentration;

$I_1 \approx$ magnitude of second transient signal at interval 16, $I_1 =$ magnitude of second transient signal at interval 16, or $I_1 =$ magnitude of second transient signal at interval 16, +/-10%, 5% or 1%;

$I_2 \approx$ magnitude of second transient signal at interval 5, $I_2 =$ magnitude of second transient signal at interval 5, or $I_2 =$ magnitude of second transient signal at interval 5, +/-10%, 5% or 1%;

$I_3 \approx$ magnitude of second transient signal at interval 12, $I_3 =$ magnitude of second transient signal at interval 12, or $I_3 =$ magnitude of second transient signal at interval 12, +/-10%, 5% or 1%;

$I_4 \approx$ magnitude of second transient signal at interval 14, $I_4 =$ magnitude of second transient signal at interval 14, or $I_4 =$ magnitude of second transient signal at interval 14, +/-10%, 5% or 1%;

$x_1 \approx 1.18$, $x_1 = 1.18$, or $x_1 = 1.18 +/- 10\%$, 5% or 1%;

$x_2 \approx 0.97$, $x_2 = 0.97$, or $x_2 = 0.97 +/- 10\%$, 5% or 1%;

$x_3 \approx (-)11.32$, $x_3 = (-)11.32$, or $x_3 = (-)11.32 +/- 10\%$, 5% or 1%;

$x_4 \approx 38.76$, $x_4 = 38.76$, or $x_4 = 38.76 +/- 10\%$, 5% or 1%;

$x_5 \approx (-)39.32$, $x_5 = (-)39.32$, or $x_5 = (-)39.32 +/- 10\%$, 5% or 1%;

$x_6 \approx 0.0928$, $x_6 = 0.0928$, or $x_6 = 0.0928 +/- 10\%$, 5% or 1%;

$x_7 \approx (-)0.85$, $x_7 = (-)0.85$, or $x_7 = (-)0.85 +/- 10\%$, 5% or 1%;

$x_8 \approx 1.75$, $x_8 = 1.75$, or $x_8 = 1.75 +/- 10\%$, 5% or 1%;

$x_9 \approx (-)9.38$, $x_9 = (-)9.38$, or $x_9 = (-)9.38 +/- 10\%$, 5% or 1%; and $x_{10} \approx 0.25$, $x_{10} = 0.25$, or $x_{10} = 0.25 +/- 10\%$, 5% or 1%.

Additional features can also be utilized with the fifth, sixth and seventh aspects. For example, the magnitude of the second transient signal at each of the plurality of discrete intervals may include an average magnitude of the signal sampled throughout each interval; an error between a plurality of analyte concentrations calculated by the microprocessor may be less than ±15% as compared to referential value at 30% hematocrits; an error between a plurality of analyte concentrations calculated by the microprocessor may be less than ±15% as compared to referential value at 42% hematocrits; an error between a plurality of analyte concentrations calculated by the microprocessor may be less than ±15% as compared to referential value at 55% hematocrits.

These and other embodiments, features and advantages will become apparent to those skilled in the art when taken with reference to the following more detailed description of the exemplary embodiments of the disclosure in conjunction with the accompanying drawings that are first briefly described.

In any of the above aspects, the fluid/physiological sample may be blood. In any of the above aspects, the analyte may be glucose. In any of the above aspects, the physical characteristic may include at least one of viscosity, hematocrit, or density of the sample, or the physical characteristic may be hematocrit, wherein, optionally, the hematocrit level is between 30% and 55%. In any of the above aspects, the first and/or second signal may be an electrical signal. In particular, the alternating signal may be an alternating electrical signal. In any of the above aspects, where H represents, or is, the physical characteristic of the sample, it may be in the form of hematocrit. In any of the above aspects, the physical characteristic may be determined from a measured characteristic, such as the impedance or phase angle difference or offset between the input signal and the output signal from the sample.

In the aforementioned aspects of the disclosure, the steps of extracting, defining, obtaining, dividing, deriving, determining, calculating and/or storing (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

BRIEF DESCRIPTION OF THE DRAWINGS

The accompanying drawings, which are incorporated herein and constitute part of this specification, illustrate presently preferred embodiments of the disclosure, and, together with the general description given above and the detailed description given below, serve to explain features of the disclosure (wherein like numerals represent like elements), in which:

FIG. 3A(1) illustrates the biosensor 100 of the system of FIG. 1 in which there are two physical characteristic sensing electrodes upstream of the measurement electrodes.

FIG. 3A(2) illustrates a variation of the test strip of FIG. 3A(1) in which a shielding or grounding electrode is provided for proximate the entrance of the test chamber;

FIG. 3A(3) illustrates a variation of the test strip of FIG. 3A(2) in which a reagent area has been extended upstream to cover at least one of the physical characteristic sensing electrodes;

FIG. 3A(4) illustrates a variation of test strip 100 of FIGS. 3A(1), 3A(2) and 3A(3) in which certain components of the test strip have been integrated together into a single unit;

FIG. 3A(5) illustrates a plan view of the biosensor.

FIG. 3A(6) illustrates a close-up plan view of the electrodes in the biosensor.

FIG. 3B illustrates a variation of the biosensor of FIGS. 3A(1-6) in which one physical characteristic sensing electrode is disposed proximate the entrance and the other physical characteristic sensing electrode is at the terminal end of the test cell with the measurement electrodes disposed between the pair of physical characteristic sensing electrodes.

FIGS. 3C and 3D illustrate variations of FIGS. 3A(1-6) in which the physical characteristic sensing electrodes are disposed next to each other at the terminal end of the test chamber with the measurement electrodes upstream of the physical characteristic sensing electrodes.

FIGS. 3E and 3F illustrates a physical characteristic sensing electrodes arrangement similar to that of FIGS. 3A(1-6) in which the pair of physical characteristic sensing electrodes are proximate the entrance of the test chamber.

FIG. 3J is a simplified cross-sectional end view of the analytical biosensor of

FIG. 3H taken along line B-B of FIG. 3H; and

FIG. 8A illustrates data from test measurements conducted with the known technique which shows relatively high bias along with substantial variations in the bias with respect to upper and lower hematocrit values.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. As used herein, "an absolute value" of a difference refers to the magnitude of the difference, i.e. it is always positive. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably.

Figure 1:
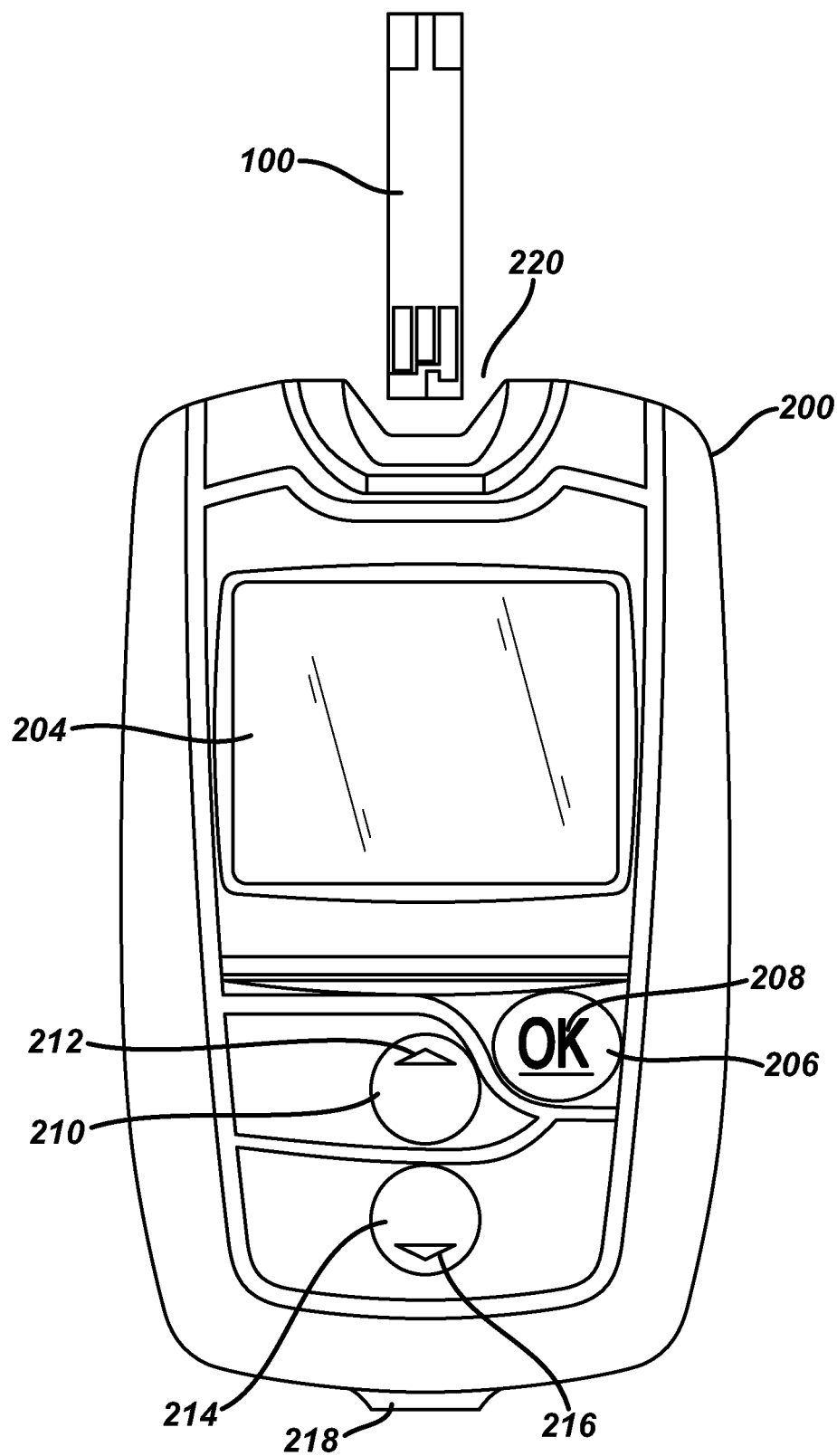
FIG. 1 illustrates an analyte measurement system.

FIG. 1 illustrates a test meter 200, for testing analyte (e.g., glucose) levels in the blood of an individual with a biosensor produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a biosensor 100 (or its variants 400, 500, or 600) into a strip port connector 220, by pressing and briefly holding first user interface input 206, or by the detection of data traffic across a data port 218. Test meter 200 can be switched off by removing biosensor 100 (or its variants 400, 500, or 600), pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2A:
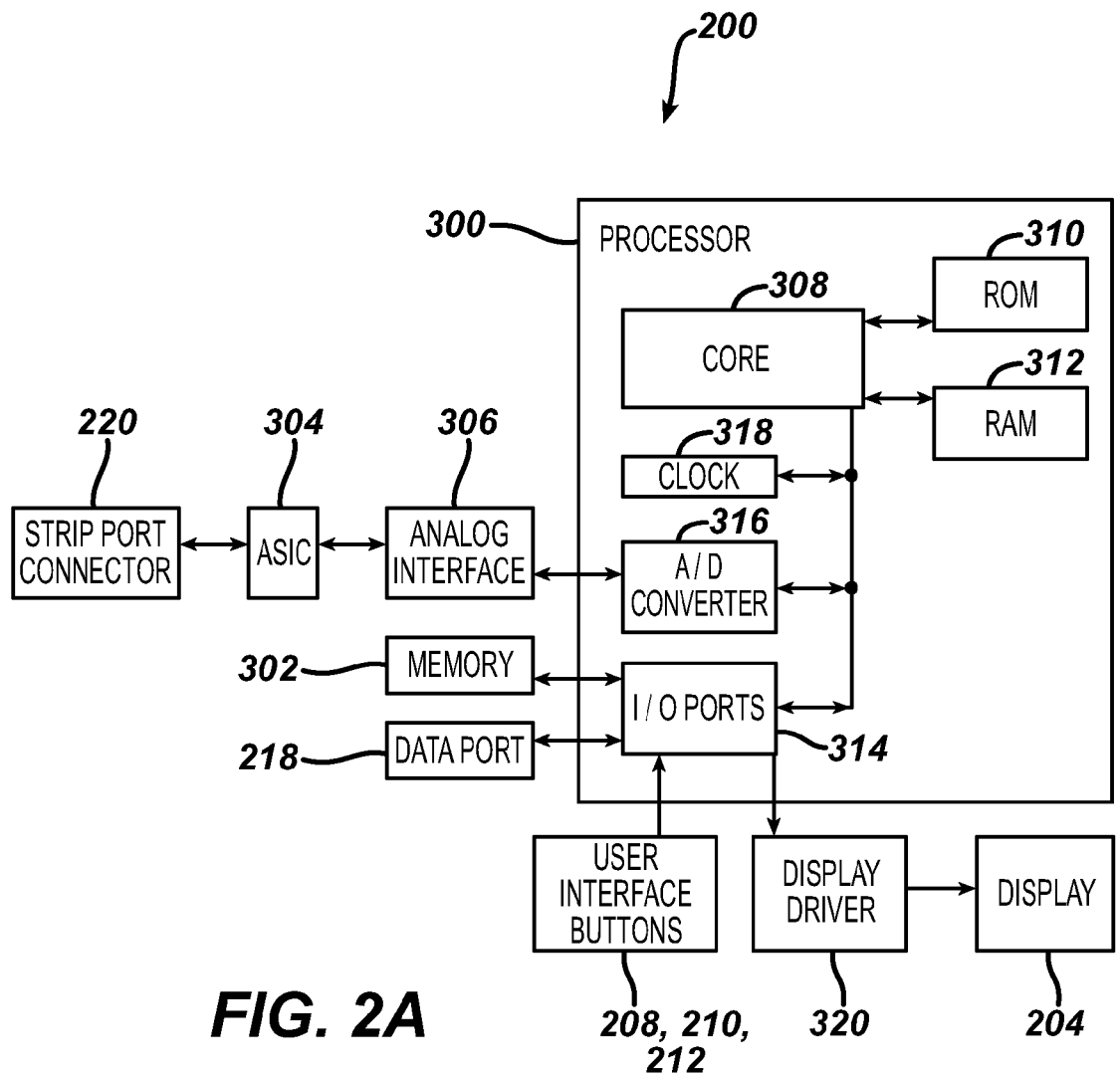
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a biosensor 100 (or its variants 400, 500, or 600) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006070200, which is hereby incorporated by reference into this application as if fully set forth herein.

FIG. 3A(1) is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14 are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A(1).

Test strip 100 may include a sample-receiving chamber 92 through which a physiological fluid sample 95 may be drawn through or deposited (FIG. 3A(2)). The physiological fluid sample discussed herein may be blood. Sample-receiving chamber 92 can include an inlet at a proximal end and an outlet at the side edges of test strip 100, as illustrated in FIG. 3A(1). A fluid sample 95 can be applied to the inlet along axis L-L (FIG. 3A(2)) to fill a sample-receiving chamber 92 so that analyte can be measured from the sample. The side edges of a first adhesive pad 24 and a second adhesive pad 26 located adjacent to reagent layer 22 each define a wall of sample-receiving chamber 92, as illustrated in FIG. 3A(1). A bottom portion or "floor" of sample-receiving chamber 92 may include a portion of substrate 5, conductive layer 50, and insulation layer 16, as illustrated in FIG. 3A(1). A top portion or "roof" of sample-receiving chamber 92 may include distal hydrophilic portion 32, as illustrated in FIG. 3A(1). For test strip 100, as illustrated in FIG. 3A(1), substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS 15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A(1), first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A(1).

In the embodiment of FIG. 3A(2) which is a variation of the test strip of FIG. 3A(1), an additional electrode 10a is provided as an extension of any of the plurality of electrodes 19a, 20a, 14, 12, and 10. It must be noted that the built-in shielding or grounding electrode 10a is used to reduce or eliminate any capacitance coupling between the finger or body of the user and the characteristic measurement electrodes 19a and 20a. The grounding electrode 10a allows for any capacitance to be directed away from the sensing electrodes 19a and 20a. To do this, the grounding electrode 10a can be connected any one of the other five electrodes or to its own separate contact pad (and track) for connection to ground on the meter instead of one or more of contact pads 15, 17, 13 via respective tracks 7, 8, and 9. In a preferred embodiment, the grounding electrode 10a is connected to one of the three electrodes that has reagent 22 disposed thereon. In a most preferred embodiment, the grounding electrode 10a is connected to electrode 10. Being the grounding electrode, it is advantageous to connect the grounding electrode to the reference electrode (10) so not to contribute any additional current to the working electrode measurements which may come from background interfering compounds in the sample. Further by connecting the shield or grounding electrode 10a to electrode 10, this is believed to effectively increase the size of the counter electrode 10 which can become limiting especially at high signals. In the embodiment of FIG. 3A(2), the reagent are arranged so that they are not in contact with the measurement electrodes 19a and 20a. Alternatively, in the embodiment of FIG. 3A(3), the reagent 22 is arranged so that the reagent 22 contacts at least one of the sensing electrodes 19a and 20a.

In alternate version of test strip 100, shown here in FIG. 3A(4), the top layer 38, hydrophilic film layer 34 and spacer 29 have been combined together to form an integrated assembly for mounting to the substrate 5 with reagent layer 22' disposed proximate insulation layer 16'.

In FIG. 3A(5), it can be seen in the plan view that the first two electrodes 19a and 20a are nearest to the entrance of the blood receiving channel 18. The tracks of the electrodes are configured to mate with five respective contact surfaces of the strip receiving port. As shown in FIG. 3A(6), which is a close-up of sample receiving end of the strip 100, the first electrode track 19a is spaced at a distance L1 from the second electrode track 20a. The second electrode track 20a is spaced at a distance L2 from electrode 10, which distance L2 may be from about 1 to about ½ of L1. The thickness h1 of the electrode 19a can be the same or different in size as compared to thickness h2 of the second electrode 20a. For electrode 10, the thickness h3 can be about 6 to about 7 times that of thickness h1 whereas respective thicknesses h4 and h5 can be about 2 to about 4 times that of h1 or h2. In the preferred embodiment, the distance L1 may be about 1.2 millimeters and the thickness h1 may be about 0.2 millimeters.

Figure 3F:
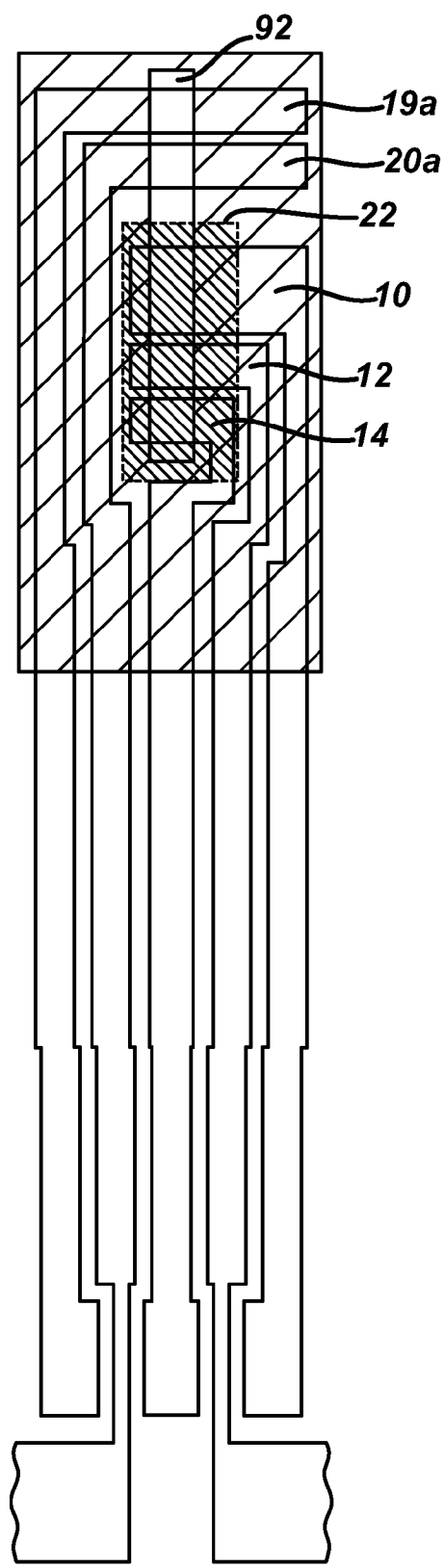
Figure 3G:
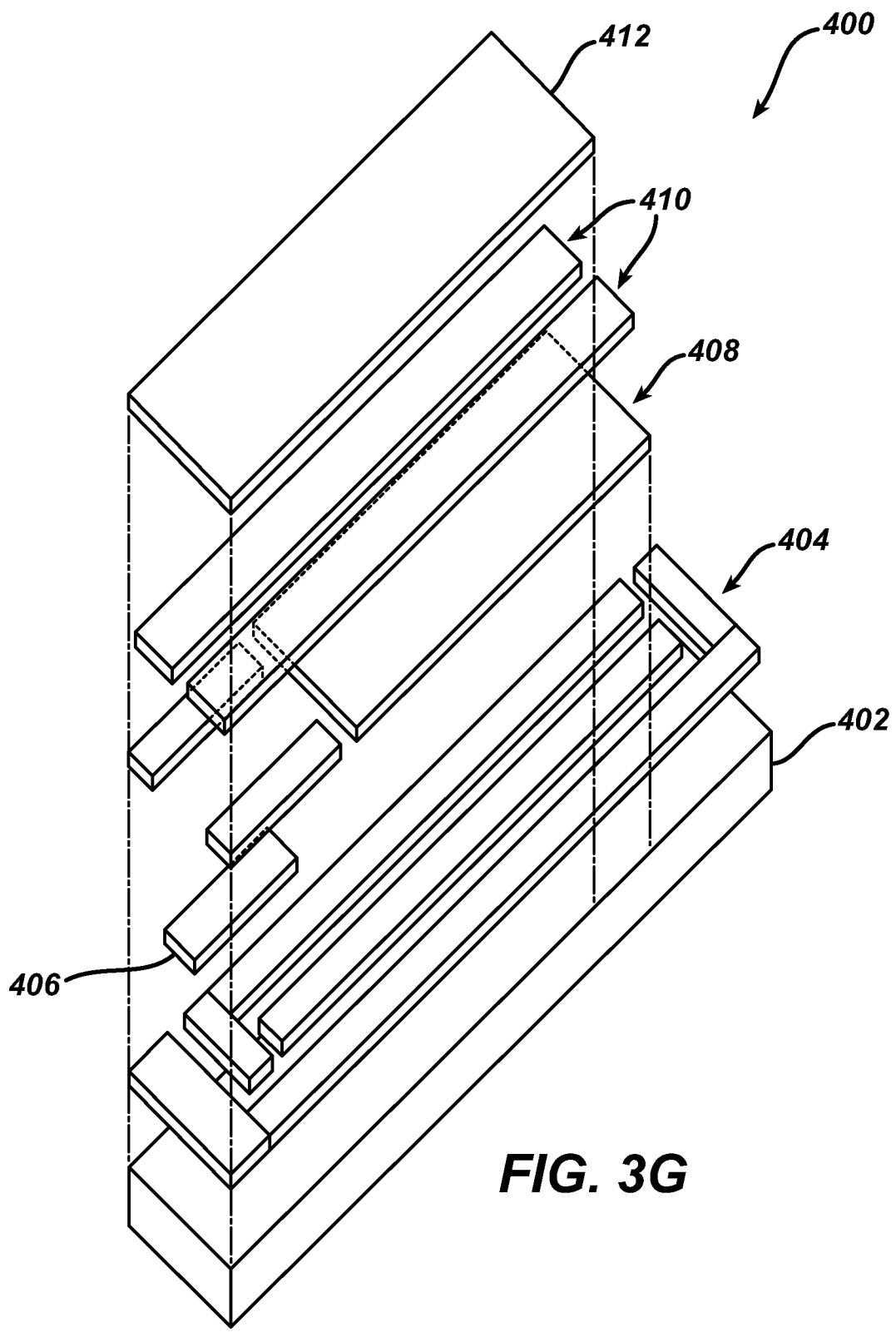
FIG. 3G is a simplified, perspective, exploded view of an analytical biosensor according to an embodiment of the present disclosure.
Figure 3H:
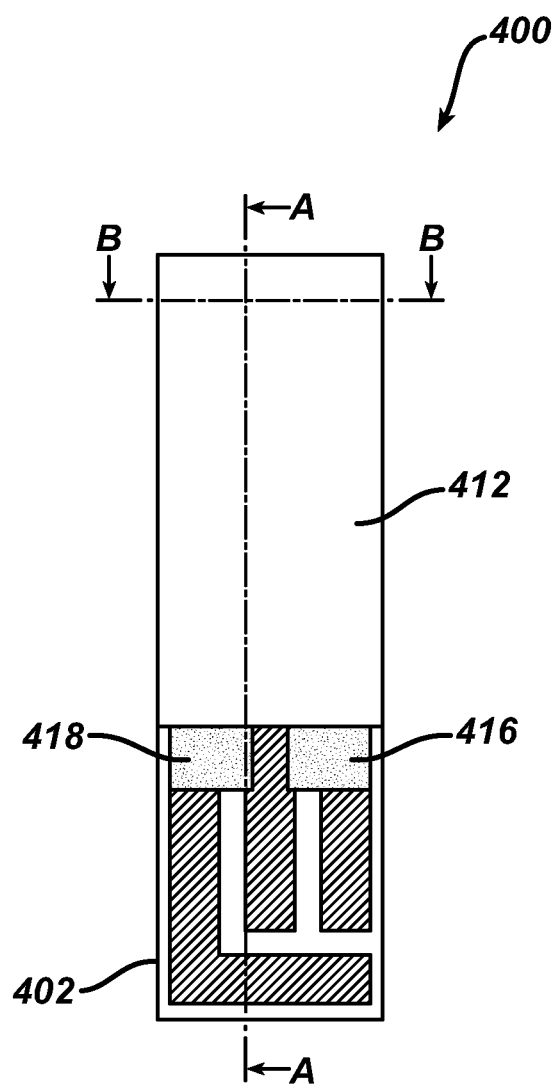
FIG. 3H is a simplified top view of the analytical biosensor of FIG. 3G.
Figure 3I:
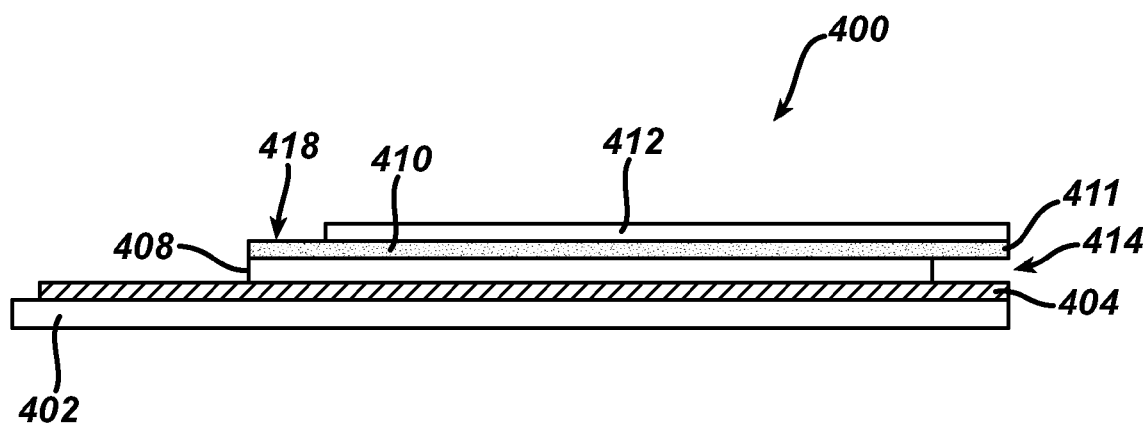
FIG. 3I is a simplified cross-sectional side view of the analytical biosensor of FIG. 3H taken along line A-A of FIG. 3H.
Figure 3J:
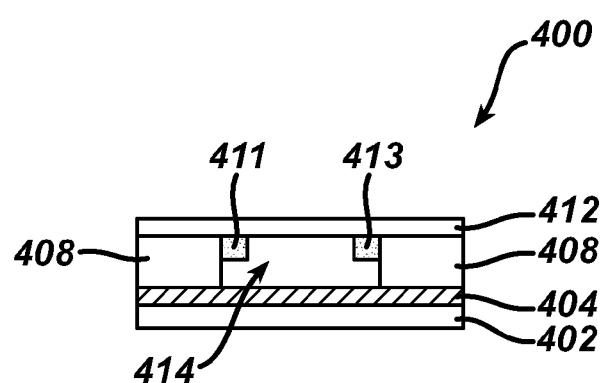
Figure 3K:
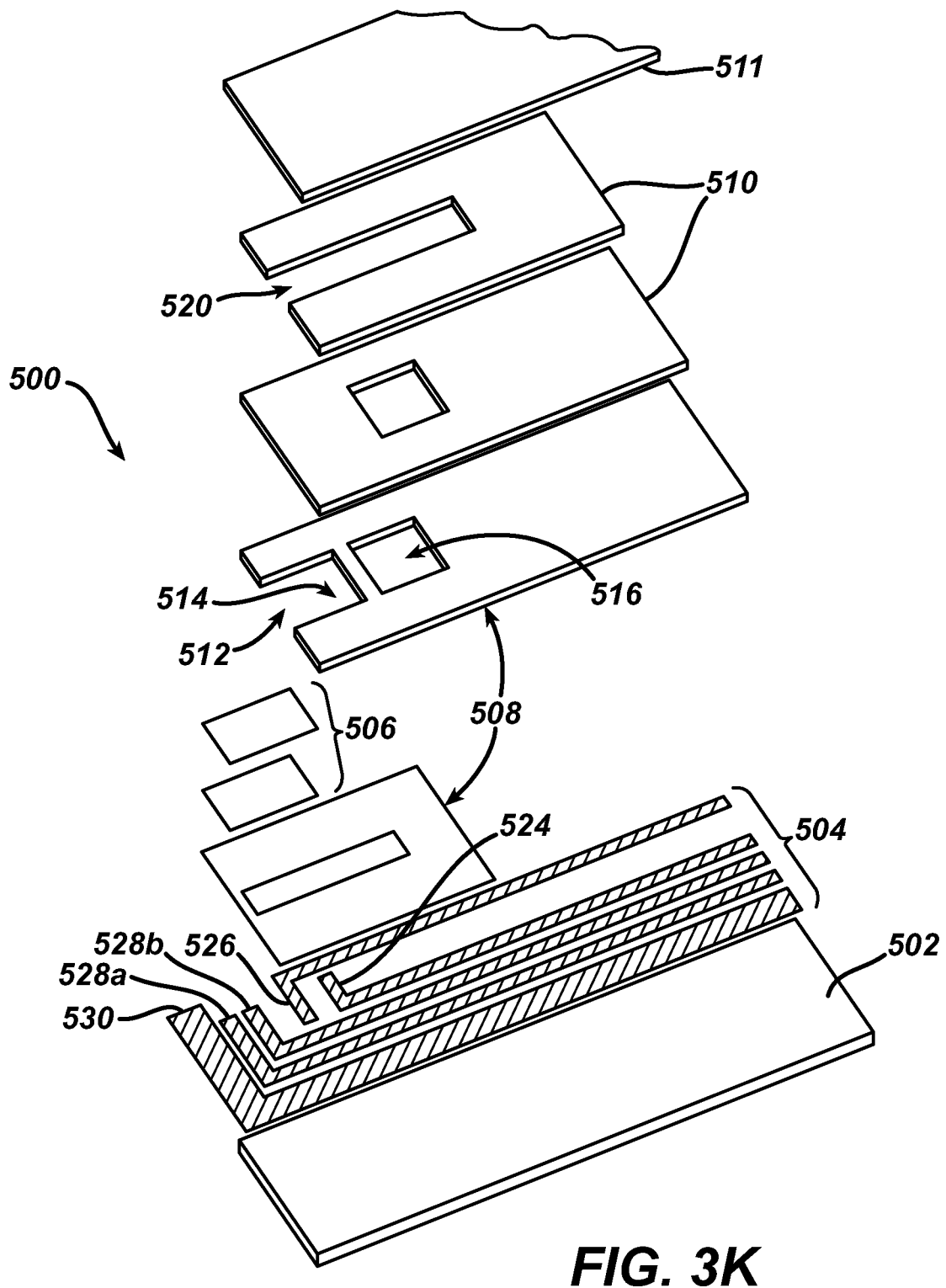
FIG. 3K is a simplified, perspective exploded view of an analytical test strip according to an embodiment of the present disclosure.
Figure 3L:
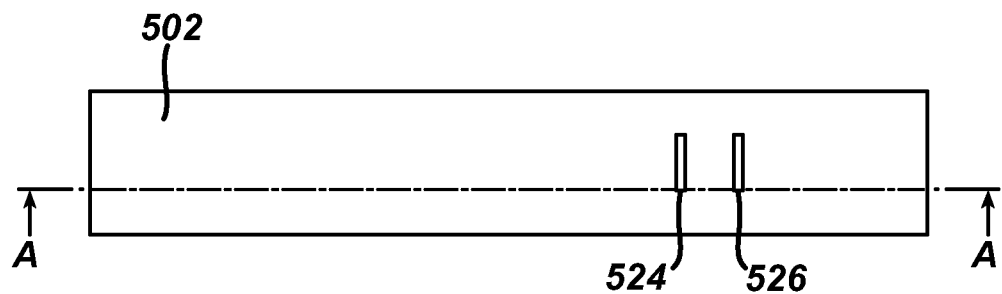
FIG. 3L is a simplified top view of the electrically-insulating substrate and a portion of a first patterned conductor layer of an analytical biosensor of FIG. 3K.
Figure 3M:
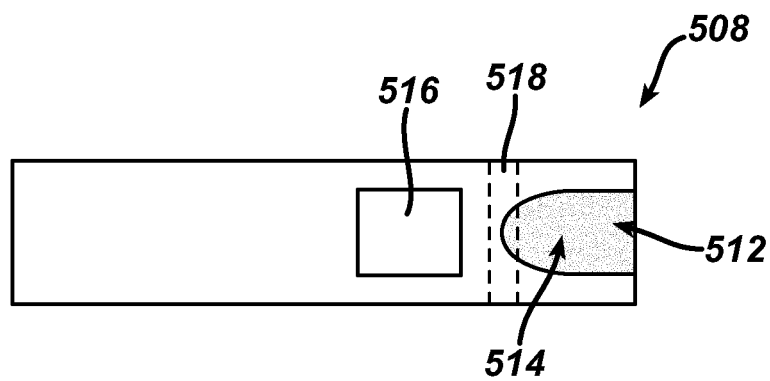
FIG. 3M is a simplified top view of the first patterned spacer layer of the analytical biosensor of FIG. 3K.
Figure 3N:
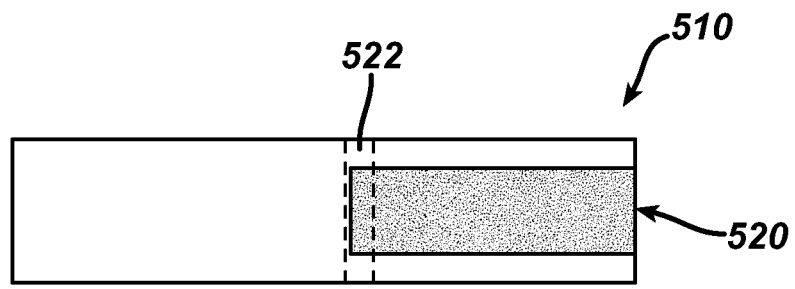
FIG. 3N is a simplified top view of the second patterned spacer layer of the analytical biosensor of FIG. 3K.
Figure 3O:
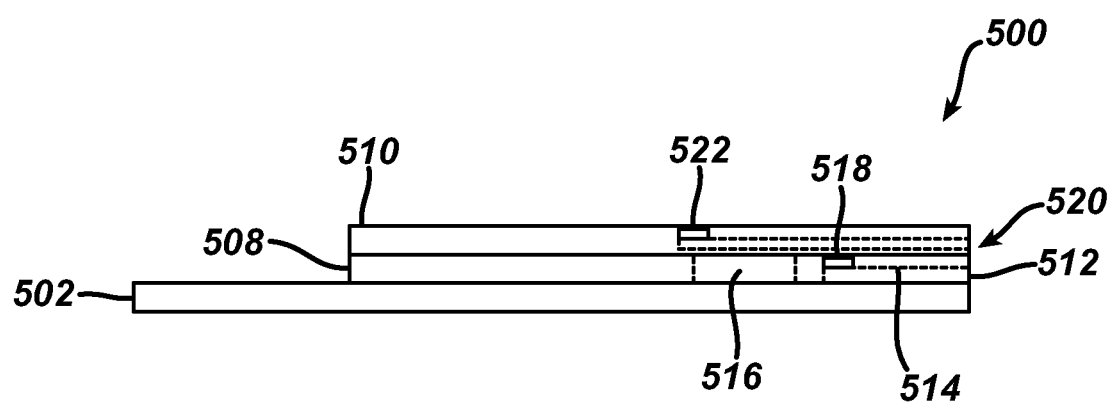
FIG. 3O is a simplified cross-sectional side view of the analytical biosensor of FIG. 3K taken along line A-A of FIGS. 2A.
Figure 3P:
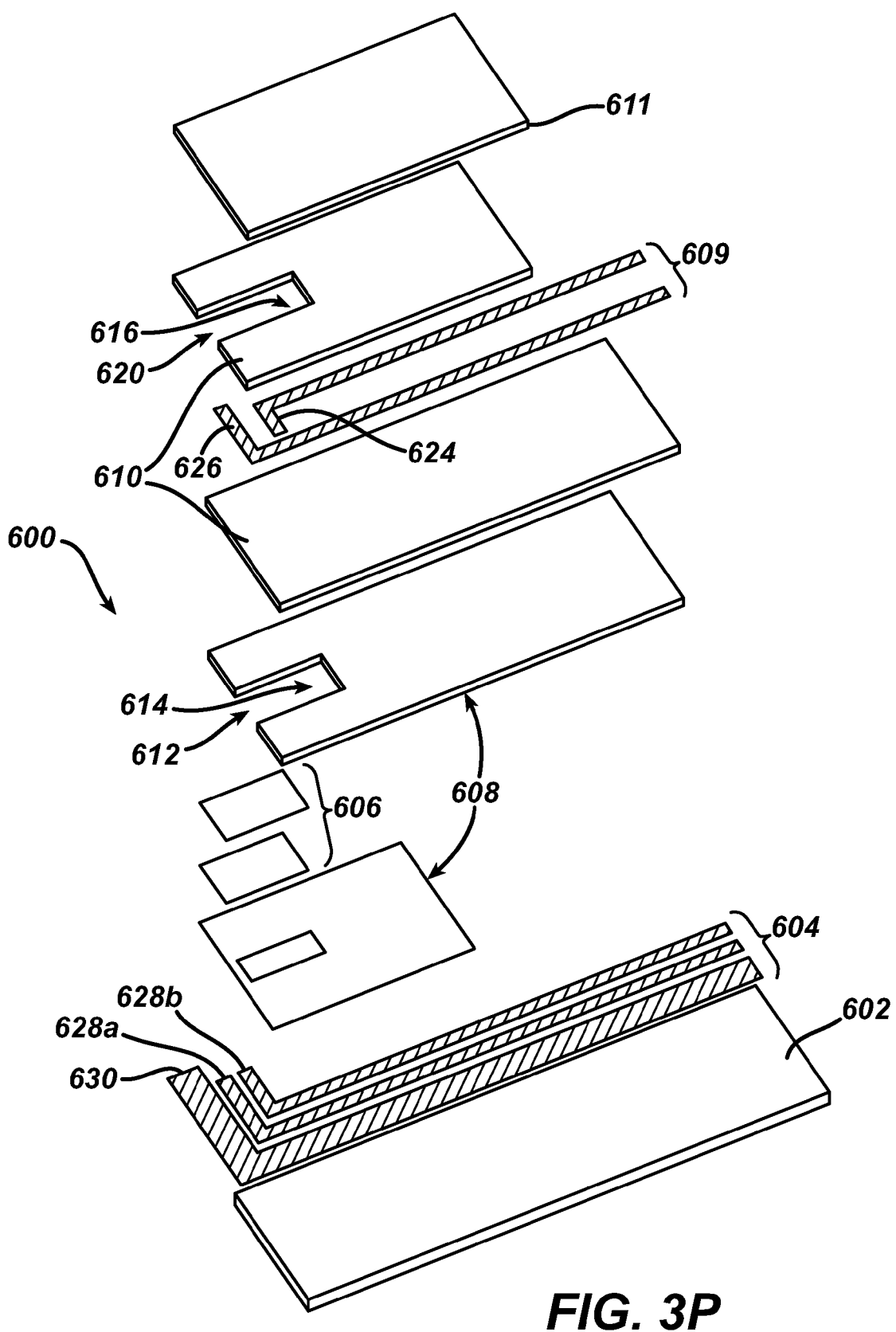
FIG. 3P is a simplified, perspective exploded view of an analytical test strip according to another embodiment of the present disclosure.
Figure 3Q:
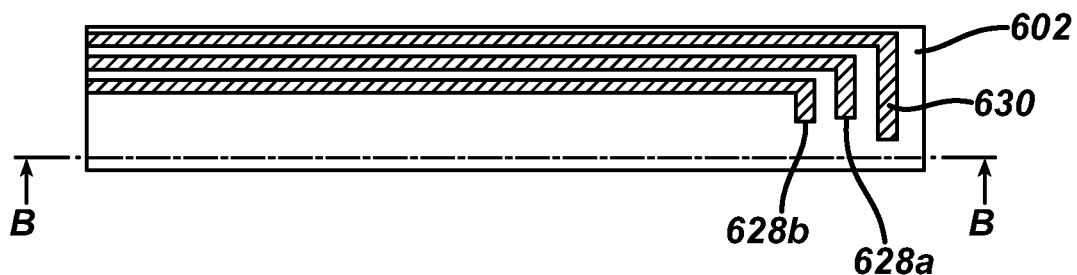
FIG. 3Q is a simplified top view of the electrically insulating substrate and first patterned conductor layer of the analytical biosensor of FIG. 3P.
Figure 3R:
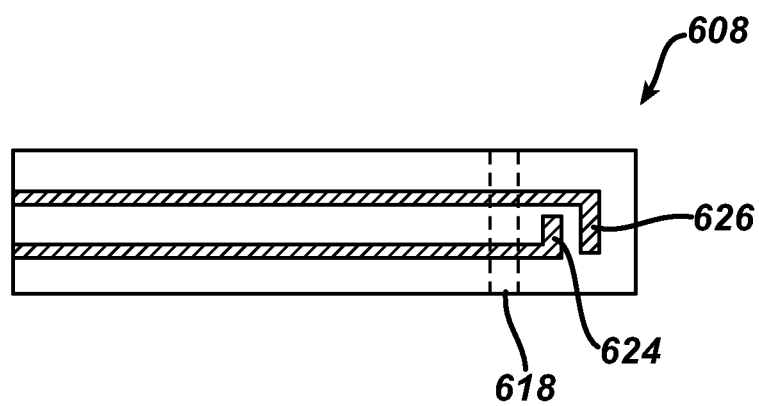
FIG. 3R is a simplified top view of a portion of a second patterned spacer layer and second patterned conductor layer of the analytical biosensor of FIG. 3P.
Figure 3S:
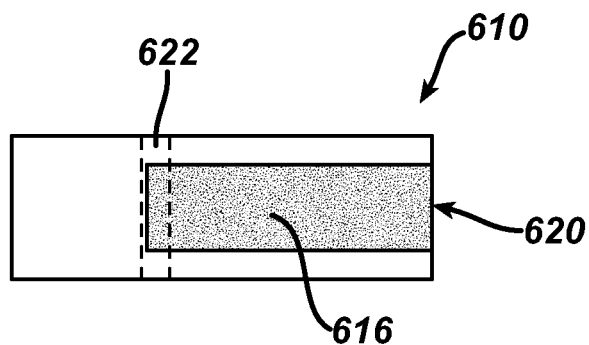
FIG. 3S is a simplified top view of a third patterned spacer layer of the analytical biosensor of FIG. 3P.
Figure 3T:
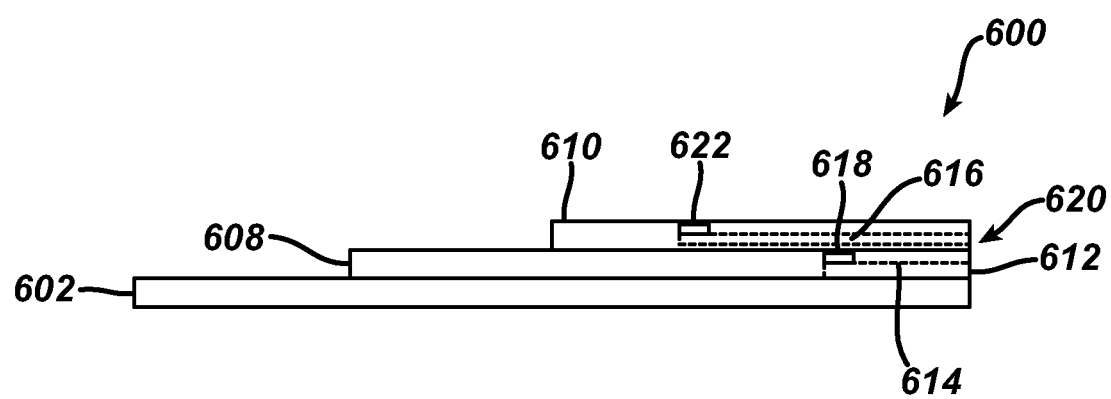
FIG. 3T is a simplified cross-sectional side view of the analytical biosensor of FIG. 3P taken along line B-B of FIG. 3Q.

Variations of the biosensor 100 (FIGS. 3A (1-6)) are shown in FIGS. 3B-3T. Briefly, with regard to variations of biosensor 100 (illustrated exemplarily in FIGS. 3B through 3T), these biosensors include an enzymatic reagent layer disposed on the working electrode, a patterned spacer layer disposed over the first patterned conductive layer and configured to define a sample chamber within the analytical biosensor, and a second patterned conductive layer disposed above the first patterned conductive layer. The second patterned conductive layer includes a first phase-shift measurement electrode and a second phase-shift measurement electrode. Moreover, the first and second phase-shift measurement electrodes are disposed in the sample chamber and are configured to measure, along with the hand-held test meter, a phase shift of an electrical signal forced through a bodily fluid sample introduced into the sample chamber during use of the analytical biosensor. Such phase-shift measurement electrodes are also referred to herein as bodily fluid phase-shift measurement electrodes. Analytical biosensors of various embodiments described herein are believed to be advantageous in that, for example, the first and second phase-shift measurement electrodes are disposed above the working and reference electrodes, thus enabling a sample chamber of advantageously low volume. This is in contrast to a configuration wherein the first and second phase-shift measurement electrodes are disposed in a co-planar relationship with the working and reference electrodes thus requiring a larger bodily fluid sample volume and sample chamber to enable the bodily fluid sample to cover the first and second phase-shift measurement electrodes as well as the working and reference electrodes.

In the embodiment of FIG. 3B, the analyte measurement electrodes 10, 12, and 14 are disposed in generally the same configuration as in FIG. 3A(1, 2, 3, 4, 5, or 6). The electrodes 19a and 20a to sense hematocrit level, however, are disposed in a spaced apart configuration in which one electrode 19a is proximate an entrance 92a to the test chamber 92 and another electrode 20a is at the opposite end of the test chamber 92. At least one of the electrodes on the biosensor is disposed to be in contact with a reagent layer 22.

In FIGS. 3C, 3D, 3E and 3F, the hematocrit sensing electrodes 19a and 20a are disposed adjacent each other and may be placed at the opposite end 92b of the entrance 92a to the test chamber 92 (FIGS. 3C and 3D) or adjacent the entrance 92a (FIGS. 3E and 3F). In all of these embodiments, the physical characteristic sensing electrodes are spaced apart from the reagent layer 22 so that these physical characteristic sensing electrodes are not impacted by the electrochemical reaction of the reagent in the presence of a fluid sample (e.g., blood or interstitial fluid) containing glucose.

Referring to FIGS. 3G through 3J, electrochemical-based analytical biosensor 400 includes an electrically-insulating substrate layer 402, a first patterned conductive layer 404 disposed on the electrically-insulating substrate layer, an enzymatic reagent layer 406 (for clarity depicted in FIG. 3G only), a patterned spacer layer 408, a second patterned conductive layer 410 disposed above first patterned conductive layer 404, and an electrically-insulating top layer 412. Patterned spacer layer 408 is configured such that electrochemical-based analytical biosensor 400 also includes a sample chamber 414 formed therein with patterned spacer layer 408 defining outer walls of sample chamber 414.

First patterned conductive layer 404 includes three electrodes, a counter electrode 404a (also referred to as a reference electrode), a first working electrode 404b and a second working electrode 404c (see FIG. 3G).

Second patterned conductive layer 410 includes a first phase-shift measurement electrode 411 and a second phase shift measurement electrode 413. Second patterned conductive layer 410 also includes a first phase-shift probe contact 416 and a second phase-shift probe contact 418.

During use of electrochemical-based analytical biosensor 400 to determine an analyte in a bodily fluid sample (e.g., blood glucose concentration in a whole blood sample), electrodes 404a, 404b and 404c are employed by an associated meter (not shown) to monitor an electrochemical response of the electrochemical-based analytical biosensor. The electrochemical response can be, for example, an electrochemical reaction induced current of interest. The magnitude of such a current can then be correlated, taking into consideration the physical characteristic (e.g., hematocrit) of the bodily fluid sample as determined by the bodily fluid sample's phase shift, with the amount of analyte present in the bodily fluid sample under investigation. During such use, a bodily fluid sample is applied to electrochemical-based analytical biosensor 400 and, thereby, received in sample chamber 414.

Electrically-insulating substrate layer 402 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, a polystyrene substrate, a silicon substrate, ceramic substrate, glass substrate or a polyester substrate (e.g., a 7 millimeters thick polyester substrate). The electrically-insulating substrate can have any suitable dimensions including, for example, a width dimension of about 5 mm, a length dimension of about 27 mm and a thickness dimension of about 0.5 mm.

First patterned conductive layer 404 can be formed of any suitable electrically conductive material such as, for example, gold, palladium, carbon, silver, platinum, tin oxide, iridium, indium, or combinations thereof (e.g., indium doped tin oxide). Moreover, any suitable technique or combination of techniques can be employed to form first patterned conductive layer 404 including, for example, sputtering, evaporation, electro-less plating, screen-printing, contact printing, laser ablation or gravure printing. A typical but non-limiting thickness for the patterned conductive layer is in the range of 5 nanometers to 400 nanometers.

As is known, conventional electrochemical-based analyte biosensors (e.g. test strips) employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte biosensor for the determination of glucose concentration in a blood sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application. In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a blood sample, enzymatic reagent layer 406 can include glucose oxidase or glucose dehydrogenase along with other components necessary for functional operation.

In general, enzymatic reagent layer 406 includes at least an enzyme and a mediator. Examples of suitable mediators include, for example, ruthenium, Hexaammine Ruthenium (III) Chloride, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 406 can be applied during manufacturing using any suitable technique including, for example, screen printing.

Applicant notes that enzymatic reagent layer 406 may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, analytical test strips and related methods described herein, are in U.S. Pat. No. 6,733,655, which is hereby fully incorporated by reference herein to this application.

Patterned spacer layer 408 can be formed of any suitable material including, for example, a 95 micrometers thick, double-sided pressure sensitive adhesive layer, a heat activated adhesive layer, or a thermo-setting adhesive plastic layer. Patterned spacer layer 408 can have, for example, a thickness in the range of from about 1 micron to about 500 microns, preferably between about 10 microns and about 400 microns, and more preferably between about 40 microns and about 200 microns.

Second patterned conductive layer 410 can be formed of any suitable conductive material including, for example, copper, silver, palladium, gold and conductive carbon materials. Second patterned conductive layer 410 can be, for example, disposed on a lower surface of electrically-insulating top layer 412 (as depicted in FIGS. 3G-3J) or embedded in the lower surface of electrically-insulating top layer 412. Second patterned conductive layer 410 can have any suitable thickness including, for example, a thickness in the range of 20 microns to 400 microns.

First phase-shift measurement electrode 411 and second phase shift measurement electrode 413 of second patterned conductive layer 410 are separated within sample chamber 414 by a gap (in the horizontal direction of FIG. 3J) that is suitable for phase-shift measurement. Such a gap can be, for example, in the range of 20 microns to 1,400 microns with a typical gap being 500 microns. Moreover, the surface area of first phase-shift measurement electrode 111 and second phase shift measurement electrode 113 that is exposed to a bodily fluid sample within sample chamber 414 is typically about 0.5 mm$^2$ but can range, for example, from about 0.1 mm$^2$ to about 2.0 mm$^2$.

Electrochemical-based analytical biosensor 400 can be manufactured, for example, by the sequential aligned formation of first patterned conductive layer 404, enzymatic reagent layer 406, patterned spacer layer 408, second patterned conductive layer 410 and electrically insulating top layer 412 onto electrically-insulating substrate layer 402. Any suitable techniques known to one skilled in the art can be used to accomplish such sequential aligned formation, including, for example, screen printing, photolithography, photogravure, chemical vapour deposition, sputtering, tape lamination techniques and combinations thereof.

Analytical biosensors according to embodiments provided herein can be configured, for example, for operable electrical connection (via, for example, first and second phase shift probe contacts 416 and 418) and use with the analytical test strip sample cell interface of a hand-held test meter as described in co-pending patent application 13/250,525, which is hereby incorporated by reference herein to this application with a copy provided in the Appendix.

It has been determined that a relationship exists between the reactance of a whole blood sample and the physical characteristic (e.g., hematocrit) of that sample. Electrical modeling of a bodily fluid sample (e.g., a whole blood sample) as parallel capacitive and resistive components indicates that when an alternating current (AC) signal is forced through the bodily fluid sample, the phase shift of the alternating signal will be dependent on both the frequency of the alternating signal voltage and the physical characteristic (e.g., hematocrit) of the sample. Therefore, the physical characteristic (e.g., hematocrit) of a bodily fluid sample can be measured by, for example, driving alternating signals of a known frequency (or known frequencies) through the bodily fluid sample and detecting their phase shift. The phase-shift measurement electrodes of analytical biosensors of various embodiments described herein are particularly suitable for use in such phase-shift measurements since the first and second phase shift measurement electrodes are in direct contact with a bodily fluid sample present in the sample chamber.

Applicant notes that for various embodiments of analytical biosensors (e.g., an electrochemical-based analytical test strip) described here for use with a hand-held test meter in the determination of an analyte (such as glucose) in a bodily fluid sample (for example, a whole blood sample) may include an electrically insulating substrate, a first patterned conductor layer disposed on the electrically insulating substrate and having a working electrode and a reference electrode. The analytical biosensor may also include an enzymatic reagent layer disposed on the working electrode, a first patterned spacer layer disposed over the first patterned conductor layer and defining both a first sample-receiving channel and an analyte determination sample chamber within the analytical biosensor, and a second patterned spacer layer disposed over the first patterned spacer layer and defining at least a second sample-receiving channel. In addition, the analytical biosensor further includes a bodily fluid phase-shift sample chamber in fluidic communication with the second sample-receiving channel. Moreover, the first sample-receiving channel and analyte determination sample chamber of the analytical biosensor are isolated from the second sample-receiving channel and bodily fluid phase-shift sample chamber of the analytical biosensor.

Analytical biosensors of various embodiments described herein are believed by applicant to be beneficial in that, for example, the isolation (fluidic and electrical) between the analyte determination sample chamber and the bodily fluid phase-shift sample chamber prevents potential interference between the determination of the analyte in the bodily fluid sample and a phase-shift measurement of the bodily fluid. Applicant notes that certain advantages are obtained by having the first sample-receiving channel and analyte determination chamber are separated from the second sample-receiving channel and bodily fluid phase-shift sample chamber by portions of the first and/or second patterned spacer layers that can be thinner, thus providing for an analytical biosensor with a small, yet mechanically stable, cross-section.

Referring to FIGS. 3K-3O, electrochemical-based analytical biosensor 500 includes an electrically-insulating substrate 502, a first patterned conductor layer 504 disposed on the electrically-insulating substrate layer, an enzymatic reagent layer 506 (for clarity depicted in FIG. 3K only), a first patterned spacer layer 508, a second patterned spacer layer 510, and a top cover 511. In the embodiment of FIG. 3K, first patterned spacer layer 508 and second patterned spacer layer 510 are depicted as bi-layer structures. However, the first and second patterned spacer layers employed in various embodiments provided herein can be unitary layers or any other suitably formed layer.

First patterned spacer layer 508 is configured such that electrochemical-based analytical biosensor 500 also includes a first sample-receiving channel 512 and an analyte determination sample chamber 514. First patterned spacer layer 508 is also configured to define a bodily fluid phase-shift sample chamber 516 and an analyte determination sample chamber vent 518 (for clarity not depicted in FIG. 3K).

Second patterned spacer layer 510 is configured to define a second sample-receiving channel 520 and a bodily fluid phase-shift chamber vent 522 (for clarity not depicted in FIG. 3K).

First patterned conductor layer 504 includes a first phase-shift measurement electrode 524, a second phase-shift measurement electrode 526, two working electrodes 528a and 528b and a reference electrode 530. For clarity, FIG. 3L depicts only first phase-shift measurement electrode 524 and second phase-shift measurement electrode 526 and not the entirety of first patterned conductor layer 504.

First sample-receiving channel 512 and analyte determination sample chamber 514 are isolated, both fluidically and electrically, from second sample-receiving channel 520 and bodily fluid phase-shift sample chamber 516 (see FIG. 3O in particular wherein the first and second patterned conductor layers are omitted for clarity). Moreover, in the embodiment of FIG. 3O, the bodily fluid phase-shift sample chamber is disposed in a side-by-side configuration with the analyte determination sample chamber.

During use of electrochemical-based analytical biosensor 500 to determine an analyte in a bodily fluid sample (e.g., blood glucose concentration in a whole blood sample), working and reference electrodes are employed by an associated meter (not shown) to monitor an electrochemical response of the electrochemical-based analytical biosensor. The electrochemical response can be, for example, an electrochemical reaction induced current of interest. The magnitude of such a current can then be correlated, taking into consideration the haematocrit of the bodily fluid sample as determined by the bodily fluid sample's phase shift, with the amount of analyte present in the bodily fluid sample under investigation. During such use, a bodily fluid sample is applied to electrochemical-based analytical biosensor 500 and, thereby, received in both analyte determination sample chamber 514 and bodily fluid phase-shift sample chamber 516.

Electrically-insulating substrate 502 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, a polystyrene substrate, a silicon substrate, ceramic substrate, glass substrate or a polyester substrate (e.g., a 7 millimeters thick polyester substrate). The electrically-insulating substrate can have any suitable dimensions including, for example, a width dimension of about 5 mm, a length dimension of about 27 mm and a thickness dimension of about 0.5 mm.

First patterned conductor layer 504 can be formed of any suitable electrically conductive material such as, for example, gold, palladium, carbon, silver, platinum, tin oxide, iridium, indium, or combinations thereof (e.g., indium doped tin oxide). Moreover, any suitable technique or combination of techniques can be employed to form first patterned conductor layer 504 including, for example, sputtering, evaporation, electro-less plating, screen-printing, contact printing, laser ablation or gravure printing. A typical but non-limiting thickness for the patterned conductor layer is in the range of 5 nanometers to 500 nanometers.

Applicant notes that conventional electrochemical-based analyte biosensors employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte biosensor for the determination of glucose concentration in a blood sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application. In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a blood sample, enzymatic reagent layer 506 can include glucose oxidase or glucose dehydrogenase along with other components necessary for functional operation.

In general, enzymatic reagent layer 506 includes at least an enzyme and a mediator. Examples of suitable mediators include, for example, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 506 can be applied during manufacturing using any suitable technique including, for example, screen printing.

Applicant notes that enzymatic reagent layer 506 may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, bodily-fluid phase-shift sample chambers and second sample receiving channels analytical test strips and related methods described herein, are in U.S. Pat. No. 6,733,655, which is hereby fully incorporated by reference herein to this application.

First and second patterned spacer layers 508 and 510 respectively can be formed of any suitable material including, for example, a 95 micrometers thick, double-sided pressure sensitive adhesive layer, a heat activated adhesive layer, or a thermo-setting adhesive plastic layer. First patterned spacer layer 508 can have, for example, a thickness in the range of from about 1 micron to about 500 microns, preferably between about 10 microns and about 400 microns, and more preferably between about 40 microns and about 600 microns.

Electrochemical-based analytical biosensor 500 can be manufactured, for example, by the sequential aligned formation of first patterned conductor layer 504, enzymatic reagent layer 506, first patterned spacer layer 508, and second patterned spacer layer 510 onto electrically-insulating substrate 502. Any suitable techniques known to one skilled in the art can be used to accomplish such sequential aligned formation, including, for example, screen printing, photolithography, photogravure, chemical vapour deposition, sputtering, tape lamination techniques and combinations thereof.

Analytical biosensors according to embodiments can be configured, for example, for operable electrical connection and use with the analytical biosensor sample cell interface of a hand-held test meter as described in co-pending patent application 13/250,525, which is hereby incorporated by reference herein to this application with a copy provided in the Appendix.

It has been determined that a relationship exists between the reactance of a whole blood sample and the physical characteristic (e.g., hematocrit) of that sample. Electrical modeling of a bodily fluid sample (e.g., a whole blood sample) as parallel capacitive and resistive components indicates that when an alternating signal such as, for example, alternating-current (AC) signal is forced through the bodily fluid sample, the phase shift of the alternating signal will be dependent on both the frequency of the alternating signal voltage and the physical characteristic (e.g., hematocrit, viscosity, temperature) of the sample. Therefore, the physical characteristic (e.g., hematocrit, viscosity, temperature) of a bodily fluid sample can be measured by, for example, driving alternating signals of known frequencies through the bodily fluid sample and detecting their phase shift. The phase-shift measurement electrodes of analytical test strips of various embodiments described herein are particularly suitable for use in such phase-shift measurements since the first and second phase shift measurement electrodes are in direct contact with a bodily fluid sample present in the sample chamber.

Referring to FIGS. 3P-3T, electrochemical-based analytical test strip 600 includes an electrically-insulating substrate 602, a first patterned conductor layer 604 disposed on the electrically-insulating substrate layer, an enzymatic reagent layer 606 (for clarity depicted in FIG. 3P only), a first patterned spacer layer 608, a second patterned conductor layer 609, a second patterned spacer layer 610, and a top cover 611. In the embodiment of FIG. 3P, first pattered spacer layer 608 and second patterned spacer layer 610 are depicted as bi-layer structures. However, the first and second patterned spacer layers employed in various embodiments provided herein can be unitary layers or any other suitably formatted layer.

First patterned spacer layer 608 is configured such that electrochemical-based analytical biosensor 600 also includes a first sample-receiving channel 612, an analyte determination sample chamber 614 and an analyte determination sample chamber vent 618 (not depicted in FIG. 3P but depicted with dashed lines in FIG. 3R). Analyte determination sample chamber vent 618 is configured to aid in the introduction of a bodily fluid sample into analyte determination sample chamber 614 via first sample-receiving channel 612.

Second patterned spacer layer 610 is configured to define a second sample-receiving channel 620, a bodily fluid phase-shift sample chamber 616 and a bodily fluid phase-shift chamber vent 622 (not depicted in FIG. 3P but depicted with dashed lines in FIG. 3S). Bodily fluid phase-shift chamber vent 622 is configured to aid in the introduction of a bodily fluid sample into bodily fluid phase-shift sample chamber 616 via second sample-receiving channel 620.

First patterned conductor layer 604 two working electrodes 628a and 628b (depicted in FIGS. 3P and 3Q) and a reference electrode 630 (also depicted in FIGS. 3P and 3Q). Second patterned conductor layer 609 includes a first phase-shift measurement electrode 624 and a second phase-shift measurement electrode 626 and is disposed above first patterned spacer layer 608 and embedded in the bi-layer structure of second pattered spacer layer 610.

First sample-receiving channel 612 and analyte determination sample chamber 614 are isolated, both fluidically and electrically, from second sample-receiving channel 620 and bodily fluid phase-shift sample chamber 616 (see FIG. 3T in particular wherein the first and second patterned conductor layers are not depicted for clarity).

In the various embodiments of the test strip, there are two measurements that are made to a blood sample deposited on the test strip. One measurement is that of the glucose in the blood sample while the other is that of physical characteristic (e.g., hematocrit) in the same sample. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. Each measurement is discussed in detail as follow with respect to FIGS. 4A, 4B and 5.

Figure 4A:
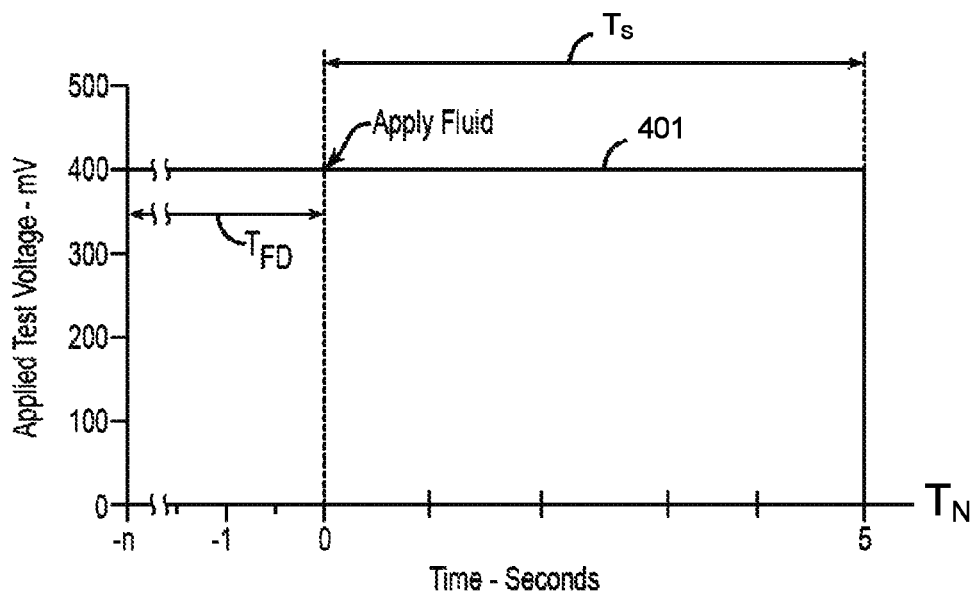
FIG. 4A illustrates a graph of time over applied potential to the biosensor of FIG. 1.

FIG. 4A is an exemplary chart of a test signal applied to test strip 100 and its variations shown here in FIGS. 3A-3T. Before a fluid sample is applied to test strip 100 (or its variants 400, 500, or 600), test meter 200 is in a fluid detection mode in which a first test signal of about 400 millivolts is applied between second working electrode and reference electrode. A second test signal of about 400 millivolts is preferably applied simultaneously between first working electrode (e.g., electrode 12 of strip 100) and reference electrode (e.g., electrode 10 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants 400, 500, or 600) such that the fluid wets second working electrode 14 and reference electrode 10. Once test meter 200 recognizes that the physiological fluid has been applied because of, for example, a sufficient increase in the measured test current at second working electrode 14, test meter 200 assigns a zero second marker at zero time "0" and starts the test time interval $T_1$. Test meter 200 may sample the current transient output at a suitable sampling rate, such as, for example, every 1 milliseconds to every 100 milliseconds. Upon the completion of the test time interval $T_1$, the test signal is removed. For simplicity, FIG. 4A only shows the first test signal applied to test strip 100 (or its variants 400, 500, or 600).

Hereafter, a description of how analyte (e.g., glucose) concentration is determined from the known current transients (e.g., the measured electrical current response in microamperes as a function of time) that are measured when the test voltages of FIG. 4A are applied to the test strip 100 (or its variants 400, 500, or 600).

Figure 4B:
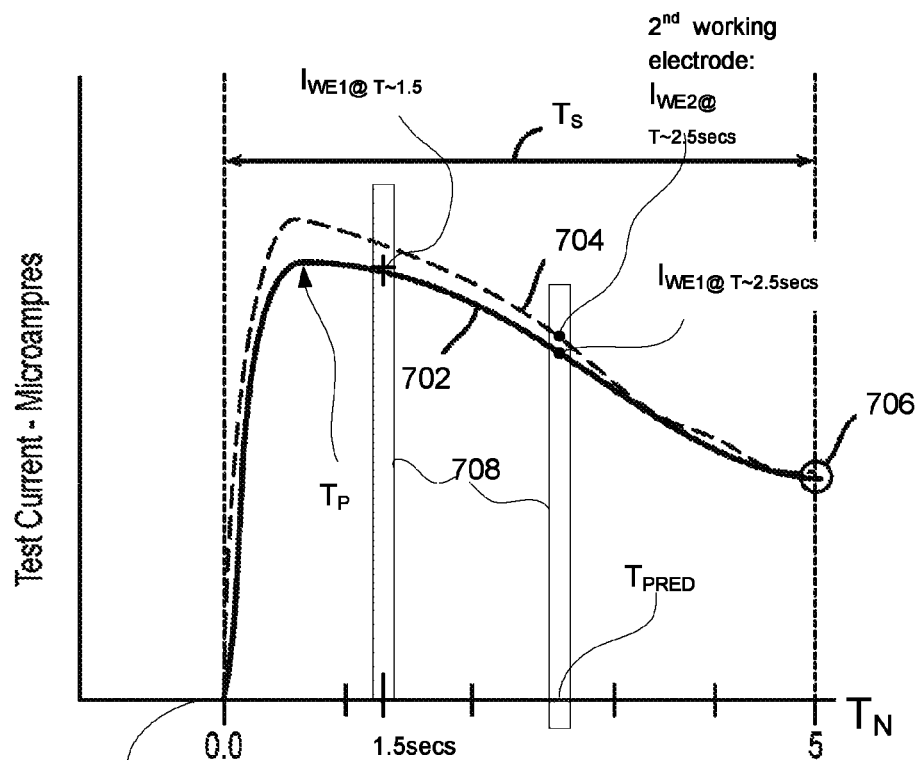
FIG. 4B illustrates a graph of time over output current from the biosensor of FIG. 1.

In FIG. 4A, the first and second test voltages applied to test strip 100 (or its variants described herein) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to time $t_0$. As the voltage 401 is maintained in FIG. 4A for the duration of $T_S$, output signals are generated, shown here in FIG. 4B with the current transient 702 for the first working electrode 12 being generated starting at zero time and likewise the current transient 704 for the second working electrode 14 is also generated with respect to the zero time. It is noted that while the signal transients 702 and 704 have been placed on the same referential zero point for purposes of explaining the process, in physical term, there is a slight time differential between the two signals due to fluid flow in the chamber towards each of the working electrodes 12 and 14 along axis L-L. However, the current transients are sampled and configured in the microcontroller to have the same start time. In FIG. 4B, the current transients build up to a peak proximate peak time Tp at which time, the current slowly drops off until approximately one of 2.5 seconds or 5 seconds after zero time. At the point 706, approximately at 5 seconds, the output signal for each of the working electrodes 12 and 14 may be measured and added together. Alternatively, the signal from only one of the working electrodes 12 and 14 can be doubled.

Referring back to FIG. 2B, the system drives a signal to measure or sample the output signals $I_E$ from at least one the working electrodes (12 and 14) at any one of a plurality of time points or positions $T_1, T_2, T_3, \ldots T_N$. As can be seen in FIG. 4B, the time position can be any time point or interval in the test sequence $T_S$. For example, the time position at which the output signal is measured can be a single time point $T_{1.5}$ at 1.5 seconds or an interval 708 (e.g., interval-10 milliseconds or more depending on the sampling rate of the system) overlapping the time point $T_{2.8}$ proximate 2.8 seconds.

From knowledge of the batch calibration code offset and batch slope for the particular test strip 100 and its variations in FIGS. 3B-3T, the analyte (e.g., glucose) concentration can be calculated.

It is noted that "Intercept" and "Slope" are the values obtained by measuring calibration data from a batch of test strips. Typically around 1500 strips (or more in some instances) are selected at random from the lot or batch. Physiological fluid (e.g., blood samples) from donors is spiked to various analyte levels, typically six different glucose concentrations. Typically, blood from 12 different donors is spiked to each of the six levels. Eight strips are given blood from identical donors and levels so that a total of 12×6×8≈576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope m and batch intercept c for the remaining strips from the lot or batch.

It is worthwhile here to note that the various components, systems and procedures described earlier allow for applicant to provide for analyte measurement system that heretofore was not available in the art. In particular, this system includes a test strip that has a substrate and a plurality of electrodes disposed on the substrate and connected to respective electrode connectors. The system further includes an analyte meter that has a housing, a test strip port connector configured to connect to the respective electrode connectors of the test strip, and a microprocessor 300. The microprocessor 300 is in electrical communication with the test strip port connector 220 to apply electrical signals or sense electrical signals from the plurality of electrodes.

Figure 2B:
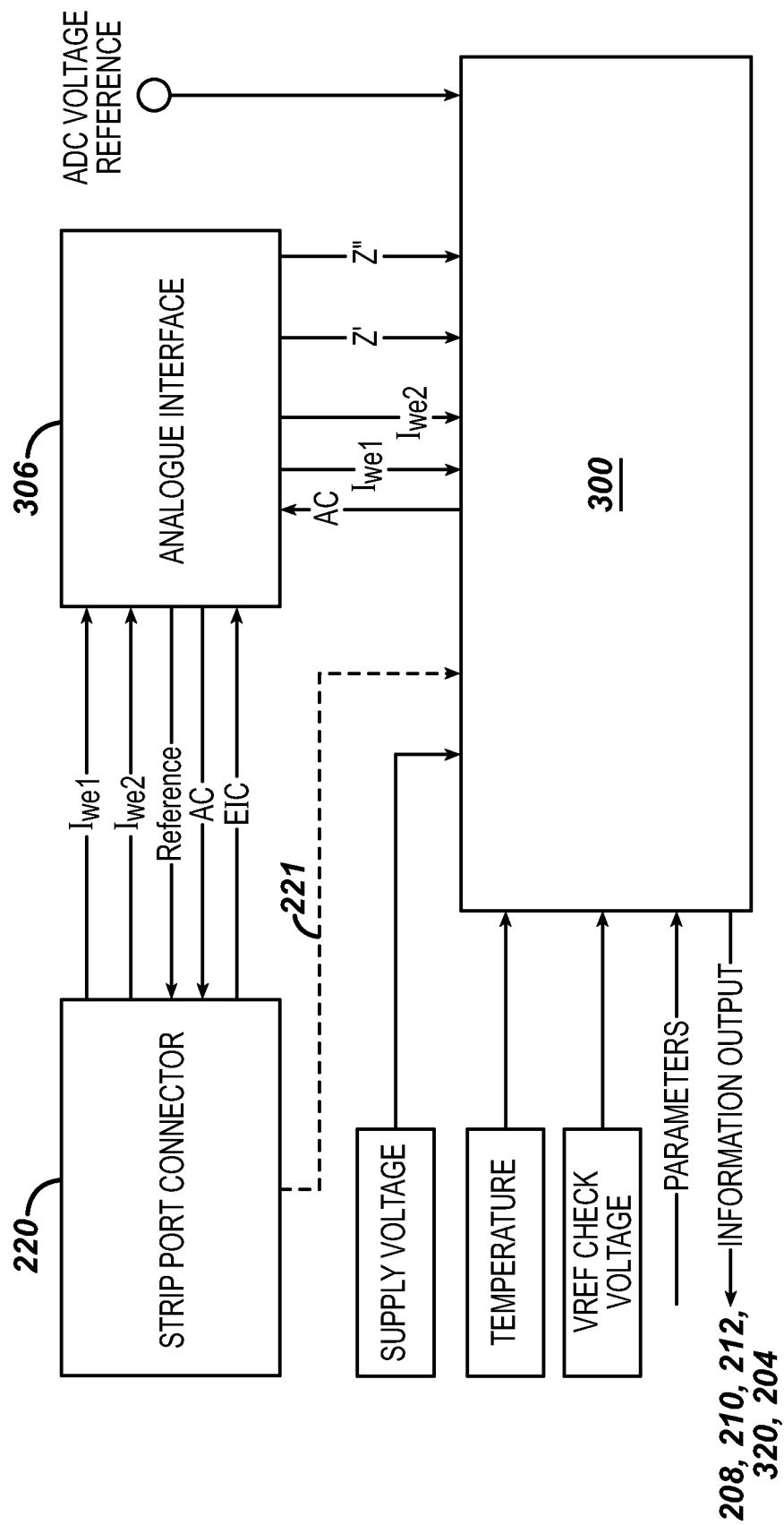
FIG. 2B illustrates in schematic form the components of yet another variation of the components of the meter 200.

Referring to FIG. 2B, details of a preferred implementation of meter 200 where the same numeral in respective FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line Ref for a reference electrode, and current sensing lines from respective working electrode 1 and working electrode 2 (i.e., $I_{we1}$ and $I_{we2}$). A strip detection line 221 can also be provided for the connector 220 to indicate insertion of a test strip. The analog interface 306 provides four inputs to the processor 300: (1) real impedance Z'; (2) imaginary impedance Z"; (3) current sampled or measured from working electrode 1 of the biosensor or $I_{we1}$; (4) current sampled or measured from working electrode 2 of the biosensor or $I_{we2}$. There is one output from the processor 300 to the interface 306 to drive an oscillating signal AC (of any value from about 25 kHz to 250 kHz or higher) to the physical characteristic sensing electrodes. A phase differential P (in degrees) can be determined from the real impedance Z' and imaginary impedance Z" where:

$$P = \tan^{-1}\{Z''/Z'\} \qquad \text{Eq. 3.1}$$

and magnitude M (in ohms and conventionally written as |Z|) from line Z' and Z" of the interface 306 can be determined where $$M = \sqrt{(Z')^2 + (Z'')^2} \qquad \text{Eq. 3.2}$$

In this system, the microprocessor is configured to: (a) apply a first signal to the plurality of electrodes so that a specific sampling time point is determined from a physical characteristic of a physiological fluid sample is derived, (b) apply a second signal to the plurality of electrodes, and (c) measure a current output from one of the plurality of electrodes at the defined specific time point so that an analyte concentration is determined. The "specific time point" may also be referred to herein as a "specified time point". For this system, the plurality of electrodes of the test strip or biosensor includes at least two electrodes to measure the physical characteristic and at least two other electrodes to measure the analyte concentration. For example, the at least two electrodes and the at least two other electrodes are disposed in the same chamber provided on the substrate. Alternatively, the at least two electrodes and the at least two other electrodes are disposed in different chambers provided on the substrate. It is noted that for some embodiments, all of the electrodes are disposed on the same plane defined by the substrate. In particular, in some of the embodiments described herein, a reagent is disposed proximate the at least two other electrodes and no reagent is disposed on the at least two electrodes. One feature of note in this system is the ability to provide for an accurate analyte measurement within about 10 seconds of deposition of a physiological sample onto the biosensor as part of the test sequence.

Figure 5:
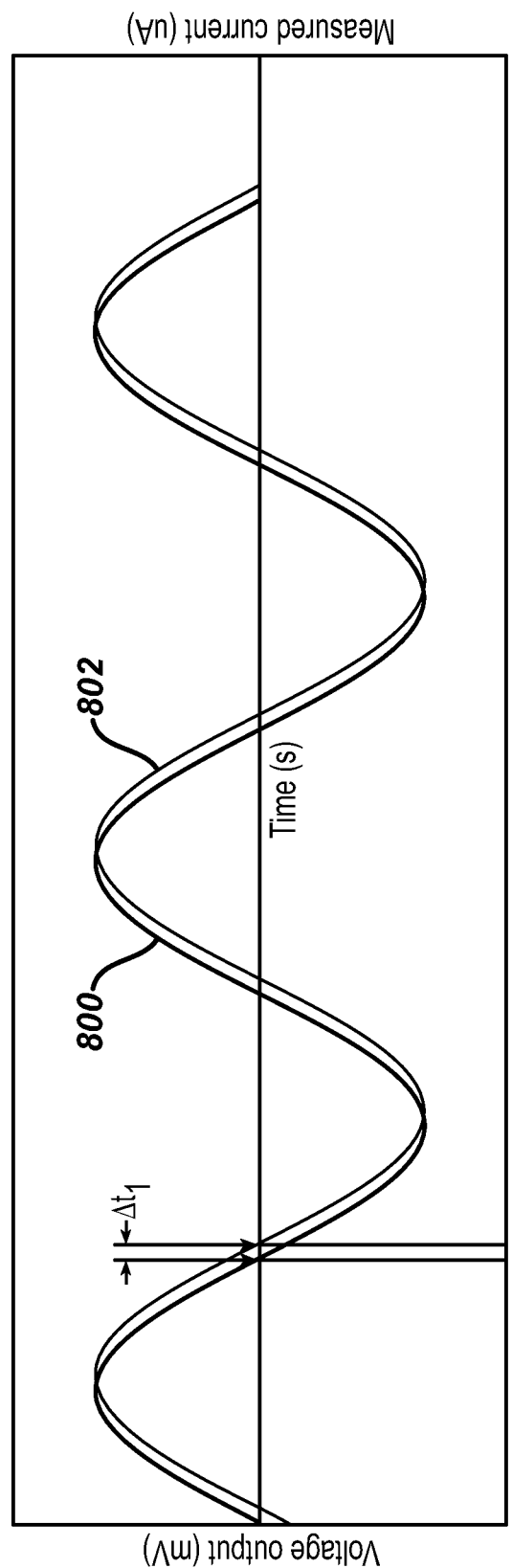
FIG. 5 illustrates a waveform applied to the test chamber and a waveform as measured from the test chamber to show a time delay between the waveforms.

A description of applicant's technique to determine the physical characteristic (e.g., hematocrit) of the blood sample is provided in relation to FIG. 5. In FIG. 5, the system 200 (FIG. 2) applies a first oscillating input signal 800 at a first frequency (e.g., of about 25 kilo-Hertz to 250 kHz or higher) to a pair of electrodes. The system is also set up to measure or detect a first oscillating output signal 802 from the third and fourth electrodes, which in particular involve measuring a first time differential $\Delta t_1$ between the first input and output oscillating signals. At the same time or during overlapping time durations, the system may also apply a second oscillating input signal (not shown for brevity) at a second frequency (e.g., about 100 kilo-Hertz to about 1MegaHertz or more, and preferably about 250 kilo Hertz) to a pair of electrodes and then measure or detect a second oscillating output signal from the third and fourth electrodes, which may involve measuring a second time differential $\Delta t_2$ (not shown) between the first input and output oscillating signals. From these signals, the system estimates a physical characteristic (e.g., hematocrit) of the blood sample based on the first and second time differentials $\Delta t_1$ and $\Delta t_2$. Thereafter, the system is able to derive a glucose concentration. The estimate of the physical characteristic (e.g., hematocrit) can be done by applying an equation of the form $$HCT_{EST} = \frac{(C_1 \Delta t_1 - C_2 \Delta t_2 - C_3)}{m_1} \qquad \text{Eq. 3.3}$$

where each of $C_1$, $C_2$, and $C_3$ is an operational constant for the test strip, $m_1$ represent a parameter from regressions data.

Details of this exemplary technique can be found in Provisional U.S. Patent Application Ser. No. 61/530,795 filed on Sep. 2, 2011, entitled, "Hematocrit Corrected Glucose Measurements for Electrochemical Test Strip Using Time Differential of the Signals", which is hereby incorporated by reference.

Another technique to determine physical characteristic (e.g., hematocrit) can be by two independent measurements of physical characteristic (e.g., hematocrit). This can be obtained by determining: (a) the impedance of the blood sample at a first frequency and (b) the phase angle of the blood sample at a second frequency substantially higher than the first frequency. In this technique, the blood sample is modeled as a circuit having unknown reactance and unknown resistance. With this model, an impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art. Details of this technique is shown and described in pending provisional patent application Ser. No. 61/530,808 filed Sep. 2, 2011, which is incorporated by reference. Other suitable techniques for determining the physical characteristic (e.g., hematocrit, viscosity, or density) of the physiological fluid sample can also be utilized such as, for example, U.S. Pat. No. 4,919,770 or "Electric Cell-Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi:10.1006/excr.2000.4919, available online at http://www.idealibrary.coml; "Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. Vol. 80, No. 1, 158-165 (2007), all of these documents are incorporated by reference.

Another technique to determine the physical characteristic (e.g., hematorcrits, density, or temperature) can be obtained by knowing the phase difference (e.g., phase angle) and magnitude of the impedance of the sample. In one example, the following relationship is provided for the estimate of the physical characteristic or impedance characteristic of the sample ("IC"):

$$IC = M^{2*}y_1 + M^*y_2 + y_3 + P^{2*}y_4 + P^*y_5 \qquad \text{Eq. 3.4}$$

where: M (from Equation 3.2) represents a magnitude |Z| of a measured impedance (in ohms);

P (from Equation 3.1) represents a phase difference between the input and output signals (in degrees))

$y_1$ is about -3.2e-08 and ±10%, 5% or 1% of the numerical value provided hereof;

$y_2$ is about 4.1e-03 and ±10%, 5% or 1% of the numerical value provided hereof;

$y_3$ is about -2.5e+01 and ±10%, 5% or 1% of the numerical value provided hereof);

$y_4$ is about 1.5e-01 and ±100%, 5% or 1% of the numerical value provided hereof; and $y_5$ is about 5.0 and ±10%, 5% or 1% of the numerical value provided hereof It is noted here that where the frequency of the input AC signal is high (e.g., greater than 75 kHz) then the parametric terms $y_1$ and $y_2$ relating to the magnitude of impedance M may be ±200% of the exemplary values given hereinsuch that each of the parametric terms may include zero or even a negative value. On the other hand, where the frequency of the AC signal is low (e.g., less than 75 kHz), the parametric terms $y_4$ and $y_5$ relating to the phase angle P may be ±200% of the exemplary values given hereinsuch that each of the parametric terms may include zero or even a negative value. It is noted here that a magnitude of H, as used herein, is generally equal to the magnitude of IC. In one exemplary implementation, the term H or HCT is equal to IC as the term H or HCT is used herein this application.

In another alternative implementation, Equation 3.5 is provided. Equation 3.5 is the exact derivation of the quadratic relationship, without using phase angles as in Equation 3.4.

$$IC = \frac{-y_2 + \left| \sqrt{y_2^2 - (4y_3(y_1 - M))} \right|}{2y_1} \qquad \text{Eq. 3.5}$$

where:
- IC is the Impedance Characteristic [%];
- M is the Magnitude of impedance [Ohm];
- $y_1$ is about 1.2292e1 and ±10%, 5% or 1% of the numerical value provided hereof;
- $y_2$ is about −4.3431e2 and ±10%, 5% or 1% of the numerical value provided hereof;
- $y_3$ is about 3.5260e4 and ±10%, 5% or 1% of the numerical value provided hereof By virtue of the various components, systems and insights provided herein, at least a method of determining an analyte concentration from a physiological sample, which may, for example, be blood (and variations of such method) is achieved by applicant. Briefly, applicant's techniques involve obtaining information or data on at least one physical characteristic of a physiological fluid sample (such as, for example, hematocrit or viscosity), deriving a specific sampling time in a test sequence sampling time duration, driving a predetermined signal into the sample, measuring or sampling a first transient signal output from the sample for the duration of the test sequence sampling time duration; defining a specific range of time that includes the specific sampling time in the test sequence sampling time duration, extracting magnitudes of the first transient signal at respective discrete intervals within the specific range of time, and determining the analyte concentration based on the extracted magnitudes of the first transient signal contained within the specific range of time.

Figure 6A:
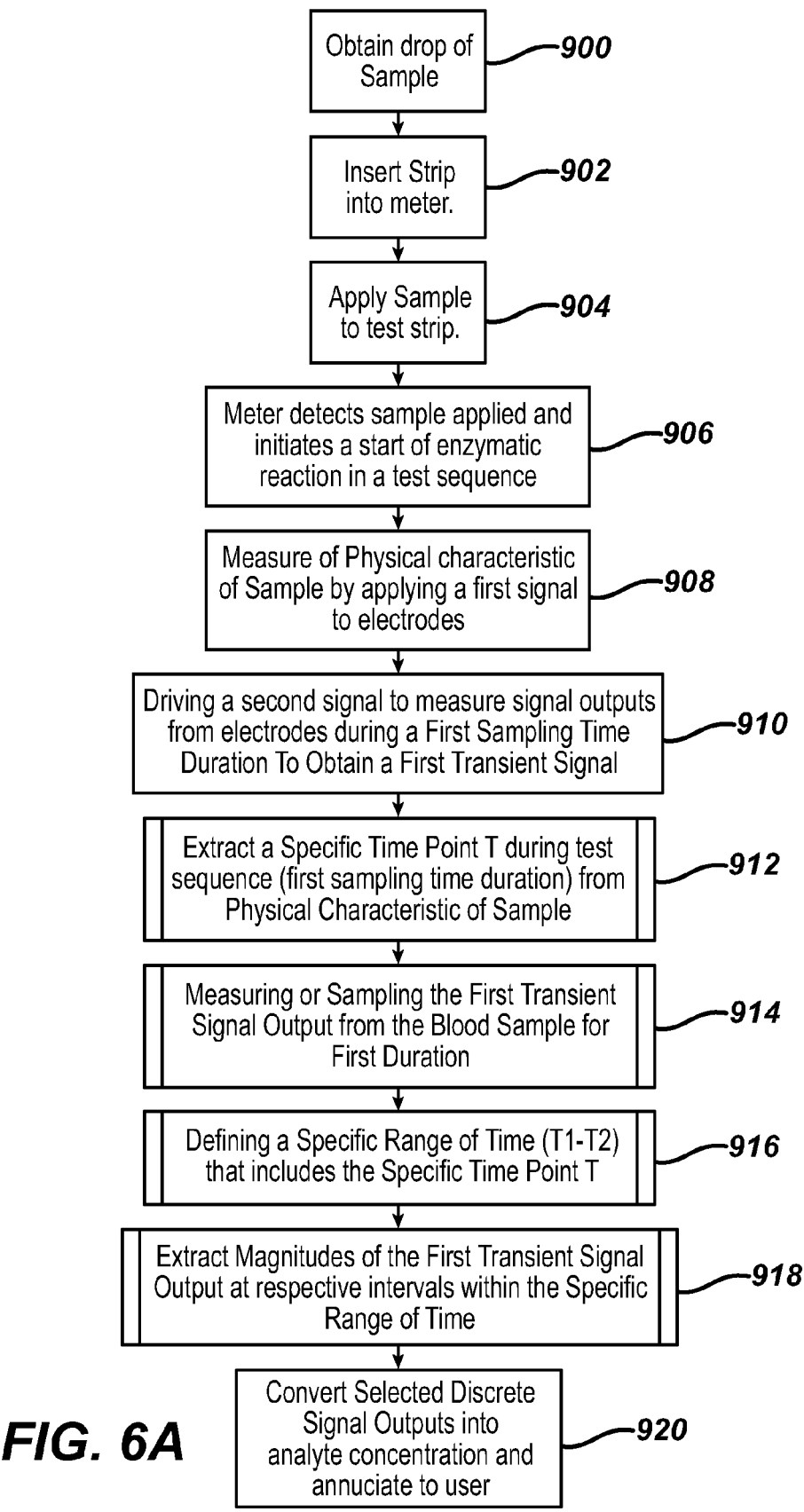
FIG. 6A illustrates a logic diagram of an exemplary method to achieve a more accurate analyte determination.

With reference to FIG. 6A, the method involves depositing a physiological sample on a biosensor at step 904 (e.g., in the form of a test strip 100 as shown in FIGS. 3A(1-6)-3T and preferably FIGS. 3A(1-6) that has been inserted into a meter (step 902). Once the meter 200 is turned on, a voltage is applied to the strip 100 (or its variants 400, 500, or 600) and when the sample is deposited onto the test chamber, the applied voltage physically transforms the analyte in the sample into a different form due to the enzymatic reaction of the analyte with the reagent in the test chamber. As the sample flows into the capillary channel of the test cell, at least one physical characteristic of the sample is obtained (step 908). In particular, the step of obtaining or measuring the physical characteristic (step 908) may include applying a first signal to the sample to derive a physical characteristic of the sample, while the step 906 of initiating an enzymatic reaction (e.g., by applying electrical signals to the sample and reagent) may involve driving a second signal to the sample for a duration that may coincide with the test sequence ("first sampling time duration"). The driving of a second signal into the sample (via electrodes) in step 910 allows for a measurement of output signals from the sample (via the electrodes) over a time period, which can be the same as the first sampling time duration. The output signal can also be characterized here as a first-transient-signal (e.g., transient curves 1002, 1004, and 1006 in FIG. 7A that relate to time and magnitudes) that is referenced with respect to both magnitudes (e.g., microamps) and time (e.g, milliseconds). At step 912, an extraction or determination of a specific sampling time T is made based on the values of the physical characteristic of the sample. A discussion of how specific sampling time T is extracted from the physical characteristics will be provided at a later point in this application. Referring back to FIG. 6A, at step 914, the first transient signal output is measured or sampled (and represented in FIG. 7A, in which the first transient signal is correlated to both time and magnitude, giving a plot of magnitude (e.g. current) against time) over a test sequence sampling time duration from about 0 seconds to about 10 seconds. At step 916, a specific range of time (from T1 to T2) that would include specific sampling time T on the first sampling time duration is defined to be a second sampling time duration. At step 918, magnitudes of the first transient signal (e.g., 1002a) that are found within the specific range of time (or second sampling time duration) are measured or sampled by the system processor. Although all of the magnitudes are measured at step 918, only selected magnitudes occurring at different intervals within the second sampling time duration (or specific time range) are utilized by the processor to convert these magnitudes into an analyte concentration value in step 920.

Figure 7A:
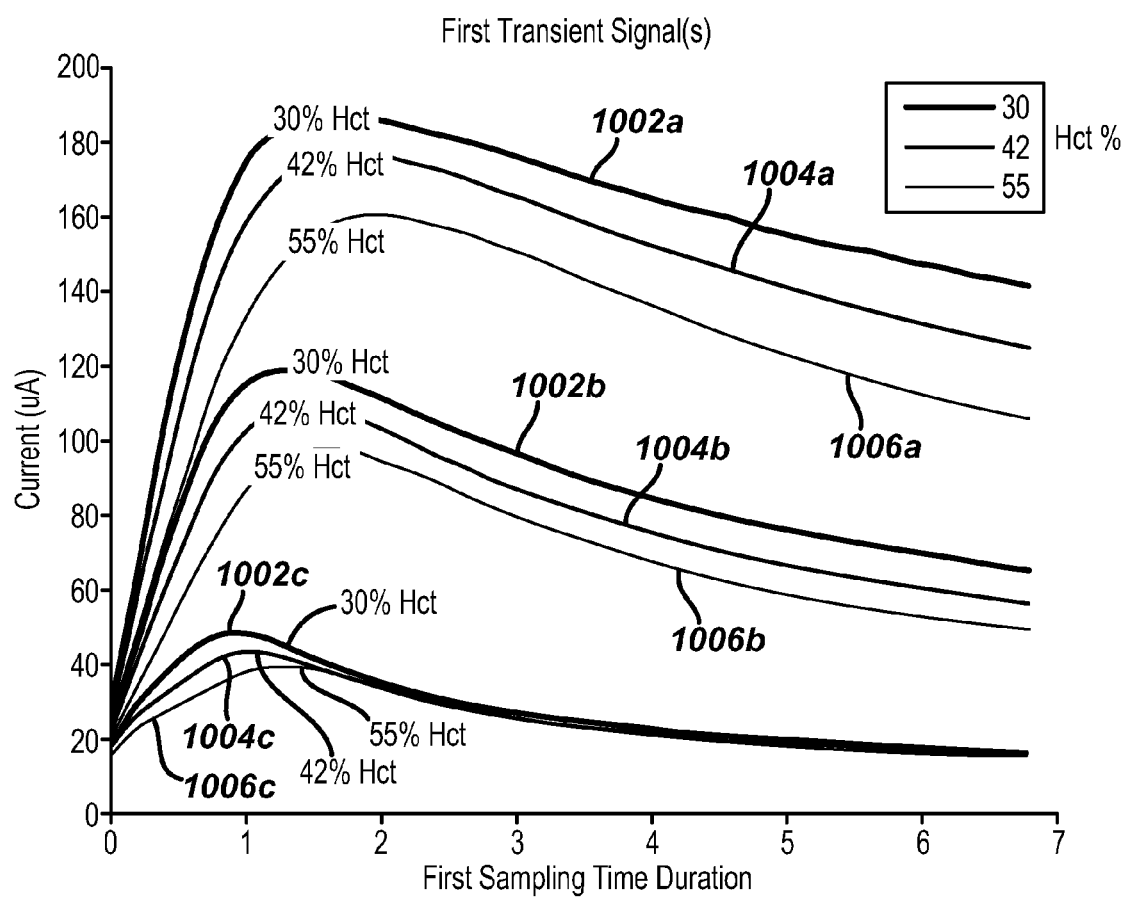
FIG. 7A illustrates output signal transients that are sampled during a test sequence duration for respective high, medium, and low glucose concentrations for each range of hematocrits at 30%, 42% and 55%.
Figure 7B:
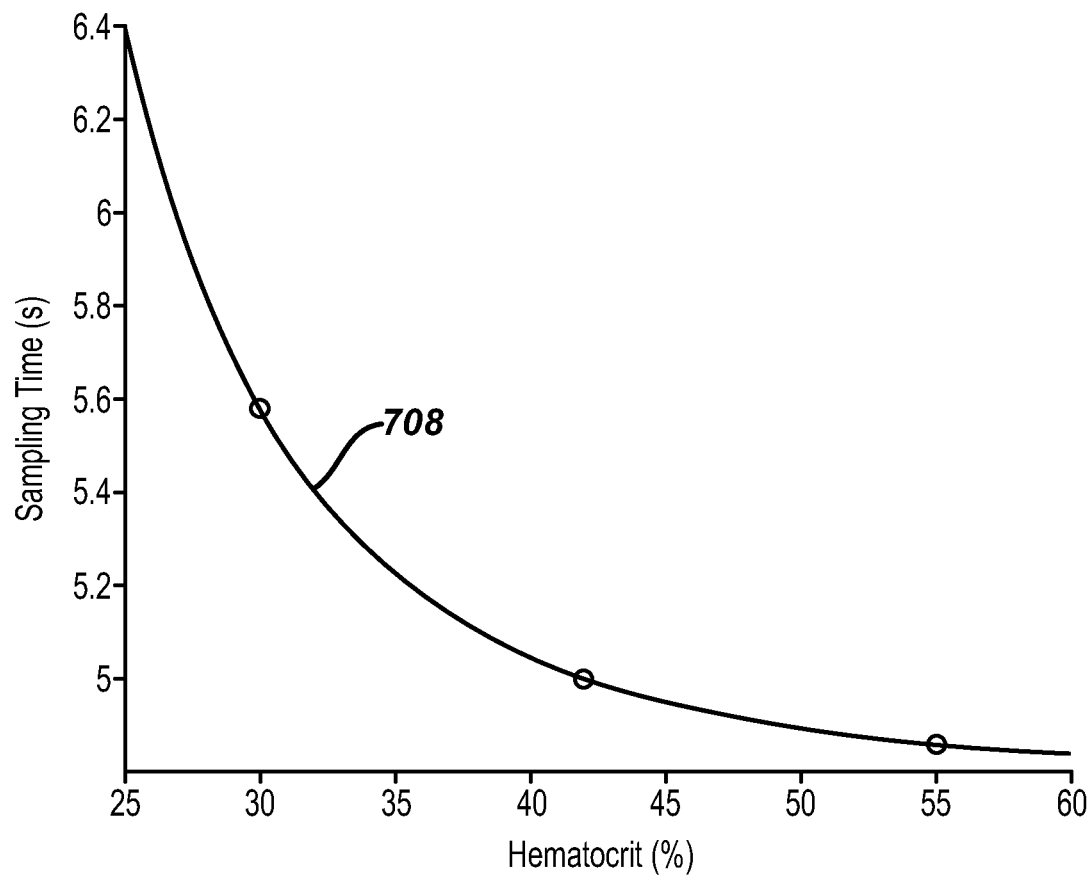
FIG. 7B illustrates the relationship between hematocrits and the time at which a magnitude of the transient signal is measured.
Figure 7C:
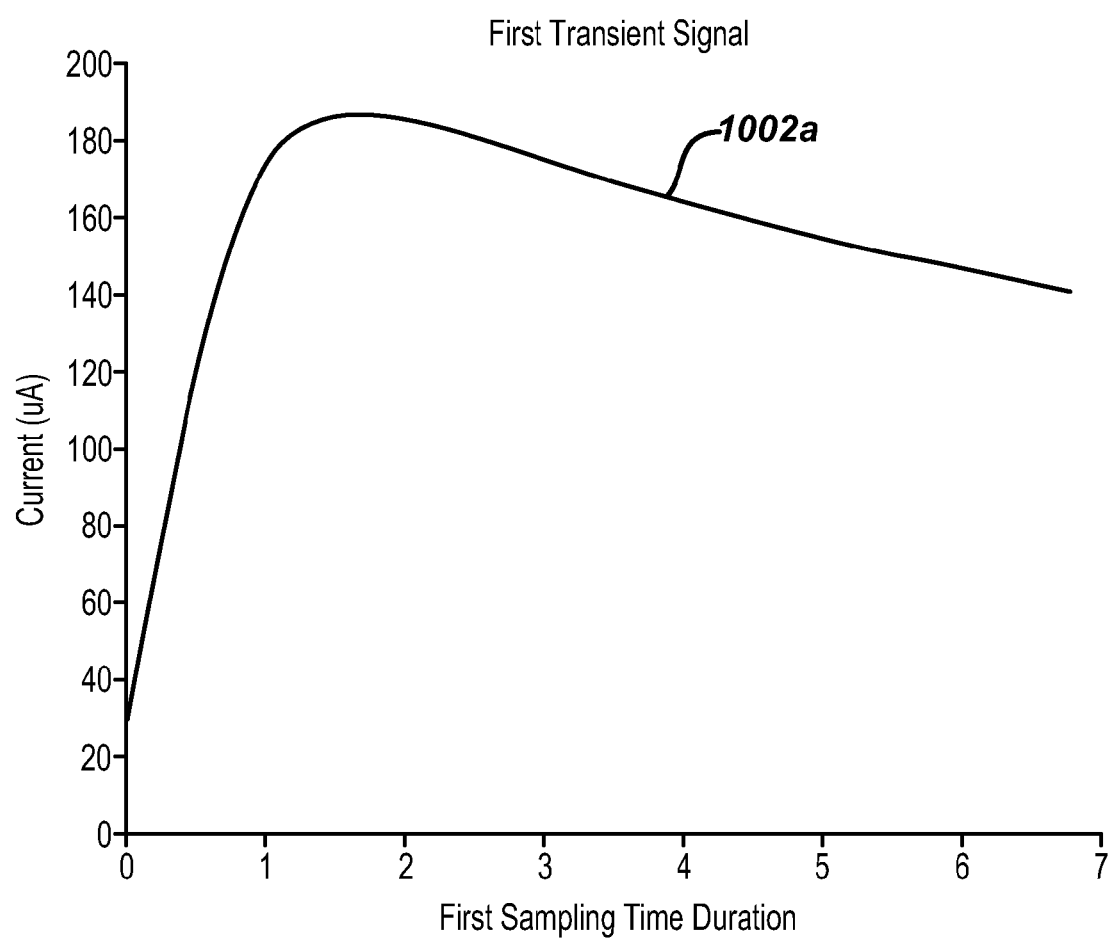
FIG. 7C illustrates one transient signal output, i.e., a "first transient signal" from the transient signals of FIG. 7B.
Figure 7D:
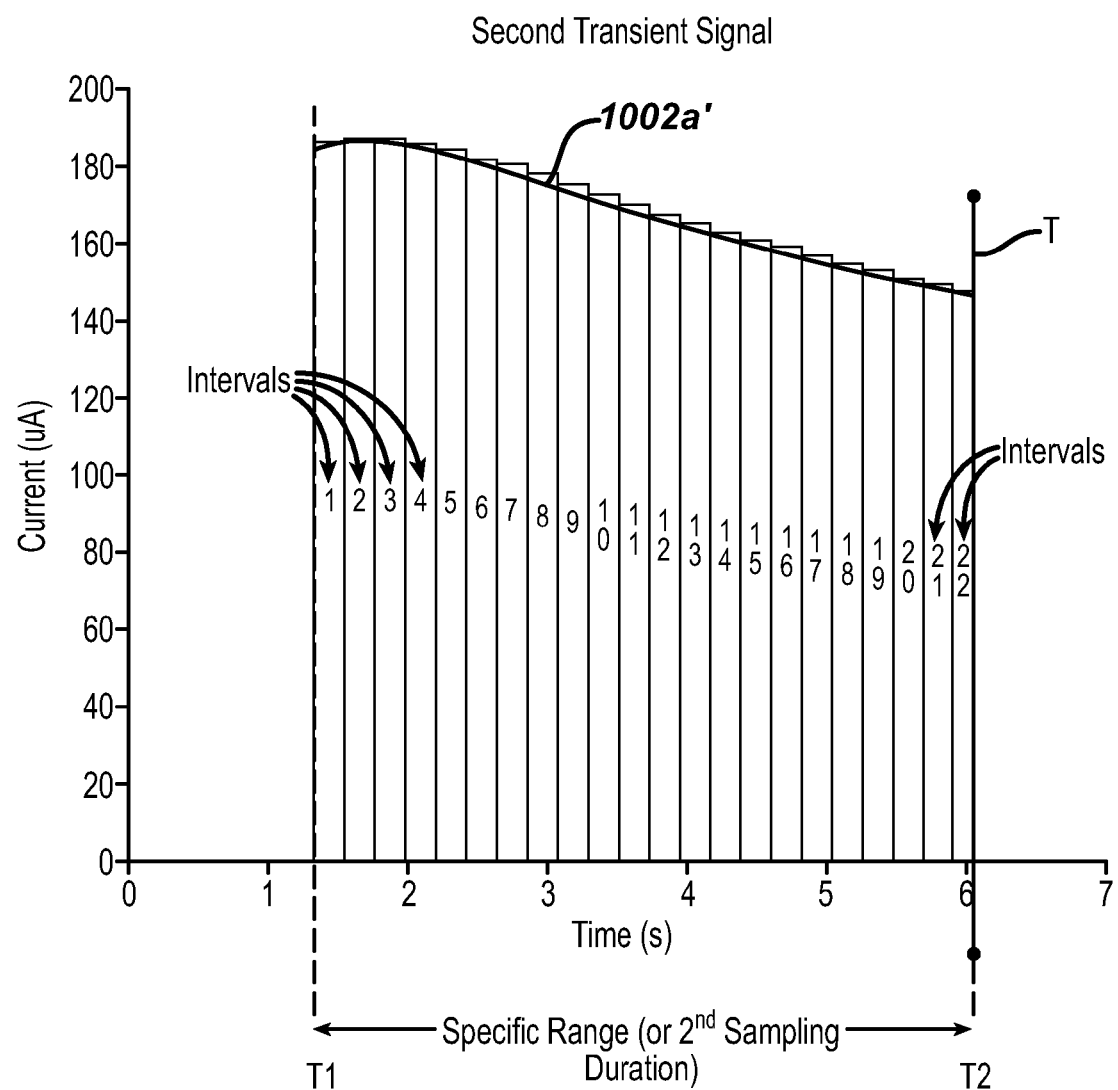
FIG. 7D illustrates the extraction of a portion of the one transient signal output in FIG. 7C and the exemplary timing intervals for measuring the magnitudes of this portion, characterized here as a "second transient signal."

The process of extracting magnitudes of the first transient signal to provide for the second transient signal can be understood with reference to FIGS. 7C and 7D. In FIG. 7C, the first transient signal 1002a is illustrated with reference to magnitude (in micro-amps from about 20 to about 180 microamps) and time (first sampling time duration from about 0 to about 7 seconds). In order to extract selected magnitudes of the first transient signal 1002a, the system must first define the specific time range T1-T2, characterized here as "second sampling time duration." This is done by determining the specific sampling time T.

Figure 7E:
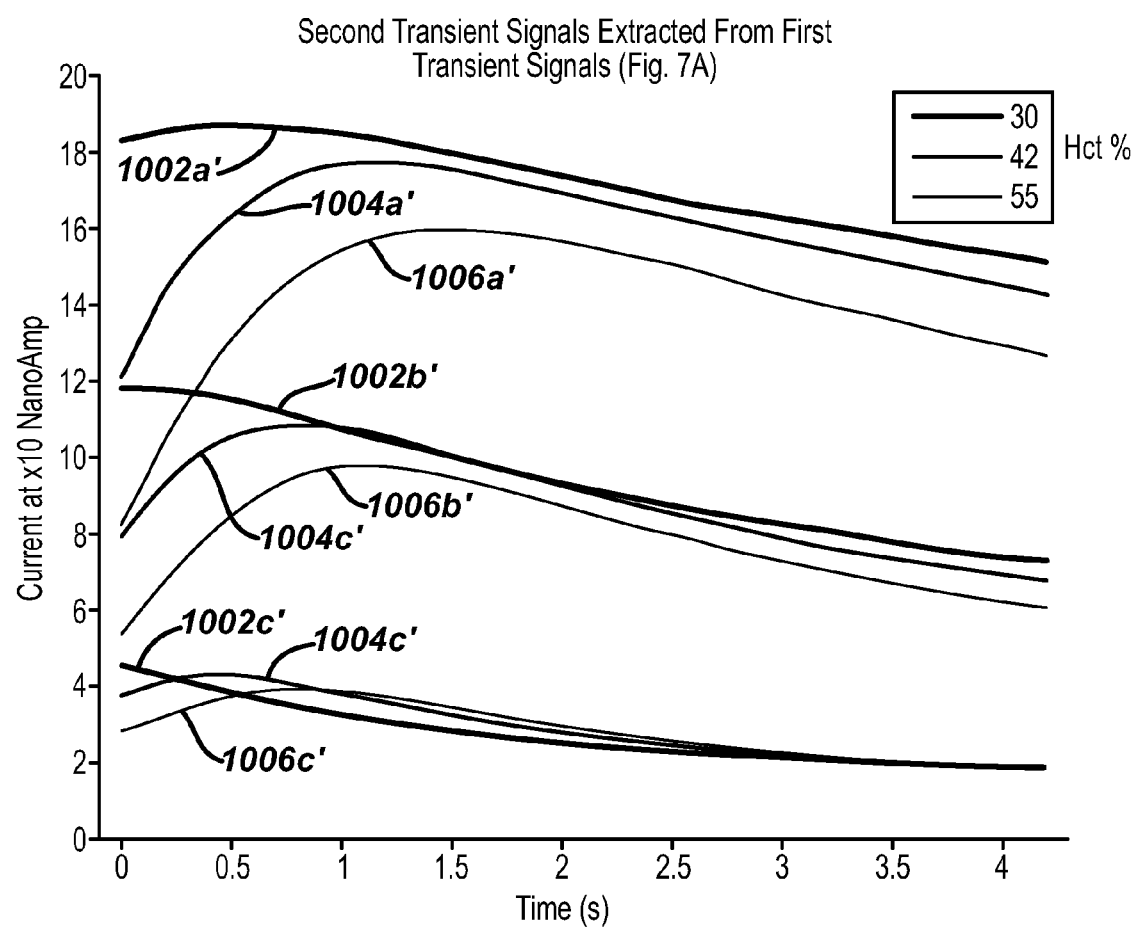
FIG. 7E illustrates the extracted signals of FIG. 7B and shifted to the left so that the start time for each of the second transient signals is about zero.

Once specific sampling time T is determined, the start time T1 of this specific range can be determined by taking a difference of specific sampling time T (in seconds) and a predetermined time A (also in seconds). The end time T2 is set to be equal to about specific sampling time T. Once range T1-T2 is defined, the system removes all transient signals outside of this specific time range, which is seen in FIG. 7D. To allow for processing, the remaining transient signal (now defined as a second transient signal 1002a') can be divided into intervals (which is preferably equal intervals but may be of unequal intervals) and designated in FIG. 7D as numerals "1" to "22" for each interval of the second transient 1002a'. The system may determine as close a value of the magnitude for each interval as possible. However, it is preferable, for ease of processing to utilize an average of the sampled magnitudes within each interval as the magnitude representative of that specific interval. It is noted that the second transient signal 1002a' can be offset to reduce confusion in computing the selected magnitudes so that the start time T1 would be set to start at zero seconds, shown here in FIG. 7E, along with other transient signals extracted from first transient signals of FIG. 7A.

Now that an overview has been provided of applicant's technique, details will now be given of particular techniques used in some of the steps in FIG. 6A or 6B. In particular, the step of applying of the first signal involves directing an alternating signal provided by an appropriate power source (e.g., the meter 200) to the sample so that a physical characteristic of the sample is determined from an output of the alternating signal. The physical characteristic being detected may be one or more of viscosity, hematocrit or density. This may include driving first and second alternating signal at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" can have some portions of the signal alternating in polarity or all alternating current signal or an alternating current with a direct current offset or even a multi-directional signal combined with a direct-current signal.

Once the physical characteristic of the sample has been determined or obtained from a suitable technique, the physical characteristic can be used to define a specific sampling time T at which point during the test sequence the output signal of the test chamber is used for further refinement of measured transient output signals to provide for an output of the analyte concentration in the sample. Specifically, applicant has found a relationship between the physical characteristic (e.g., hematocrit) and the analyte concentration, as shown here in FIG. 7A, where hematocrit is related to the analyte concentration (shown by current magnitudes in microamps). This relationship has been further explored such that the inventor was able to derive a direct relationship between the specific sampling time of the sample and the physical characteristic of the sample (e.g., hematocrit), shown here in FIG. 7B as line 708. As a consequence, by knowing the physical characteristic of the sample (e.g., hematocrit) from Equation 4 above, the relationship 708 in FIG. 7B can be exploited to allow the specific sampling time to be specified to accommodate the different levels of physical characteristic (e.g., hematocrit) so as to achieve much more accurate glucose concentration measurements.

In FIG. 7A, it can be seen that as the analyte concentration (proportional to the current output) increases, the peak of the high glucose concentration (denoted by 1002a, 1004a, and 1006a) is shifted to the right as compared to the medium glucose concentration (denoted by 1002b, 1004b, and 1006b). Similarly, the peak of the medium glucose concentration is further to the right of FIG. 7A as compared to low glucose concentration (denoted by 1002c, 1004c, and 1006c). It can also be seen here that the steady-state of the low glucose concentrations (1002c, 1004c, and 1006c) is reached earlier than the medium glucose concentrations (1002b, 1004b, and 1006b). This pattern is repeated for high glucose concentration (1002a, 1004a, and 1006b) as compared to medium glucose concentrations.

From data in FIG. 7A, the inventor was able to derive a second degree relationship between the sensed physical characteristic and the sampling time, shown here as line 708 in FIG. 7B. In FIG. 7B, a curve 708 is fitted to hematocrit values at about 30%, 42% and about 55% and glucose values for these ranges of hematocrits (from FIG. 7A). This fitted curve is found by the inventor to be an equation of the form:

$$\text{SpecificSamplingTime} = x_1 H^{x_2} + x_3 \quad \text{Eq. 4}$$

where (for convenience),
"SpecificSamplingTime" is designated as an approximate time point from the start of the test sequence at which to sample the output signal of the test strip,
H represents physical characteristic of the sample (e.g. in the form of hematocrit);
$x_1$ is about 4.3e5;
$x_2$ is about −3.9; and
$x_3$ is about 4.8.

Although the method may indicate only one sampling time point, the method may include sampling as many time points as required, such as, for example, sampling the current output over multiple discrete time points or continuously (e.g., at specified sampling time such as, every 10 milliseconds to 100 milliseconds or constantly over a duration) from the start of the test sequence until at least about 10 seconds or less after the start and the results stored for processing near the end of the test sequence. Applicant notes that the appropriate sampling time is measured from the start of the test sequence but any appropriate datum may be utilized in order to determine when to sample the output current. As a practical matter, the system can be programmed to sample the output current at an appropriate time sampling interval during the entire test sequence such as for example, one sampling every 100 milliseconds or even as little as about every 1 milliseconds. In this variation, the specific sampling time is the value used to further determine a specific time range of the first sampling time duration.

Instead of calculating from Equation 4 for the specific sampling time in the test sequence from about 0 to about 7 seconds, a look-up table, represented exemplarily here with reference to Table 1 can also be utilized in place of Equation 4 or in addition to Equation 4 to specify an appropriate sampling time point. In Table 1, the value of the physical characteristic is used by the processor of the system to look up the appropriate time at which the signal output of the biosensor is sampled or measured to determine the analyte concentration. For example, once the physical characteristic has been determined, in this case 33% hematocrit, the time at which the signal output of the biosensor 100 is utilized in determining the analyte concentration can be gleaned from Table 1, which shows that specific sampling time is at approximately 5.32 seconds after the start of the test sequence.

TABLE 1

| Physical Characteristic (e.g., Hematocrit %) | Specific Time T (seconds) |
| --- | --- |
| 30 | 5.56 |
| 31 | 5.46 |
| 32 | 5.38 |
| 33 | 5.32 |
| 34 | 5.26 |
| 35 | 5.2 |
| 36 | 5.16 |
| 37 | 5.12 |
| 38 | 5.08 |
| 39 | 5.06 |
| 40 | 5.02 |
| 41 | 5 |
| 42 | 5 |
| 43 | 4.98 |
| 44 | 4.96 |
| 45 | 4.96 |
| 46 | 4.94 |
| 47 | 4.92 |
| 48 | 4.92 |
| 49 | 4.9 |
| 50 | 4.9 |
| 51 | 4.9 |
| 52 | 4.88 |
| 53 | 4.88 |
| 54 | 4.88 |
| 55 | 4.86 |

It should be noted that the step of applying the first signal and the driving of the second signal is in sequential order in that the order may be the first signal then the second signal or both signals overlapping in sequence; alternatively, the second signal first then the first signal or both signals overlapping in sequence. Alternatively, the applying of the first signal and the driving of the second signal may take place simultaneously.

It is noted that in the preferred embodiments, the measurement of a current output for the glucose concentration is performed prior to the estimation of the physical characteristic (e.g., hematocrit). Alternatively, the physical characteristic (e.g., hematocrit) level can be estimated, measured, or obtained prior to the measurement of the glucose concentration.

Figure 6B:
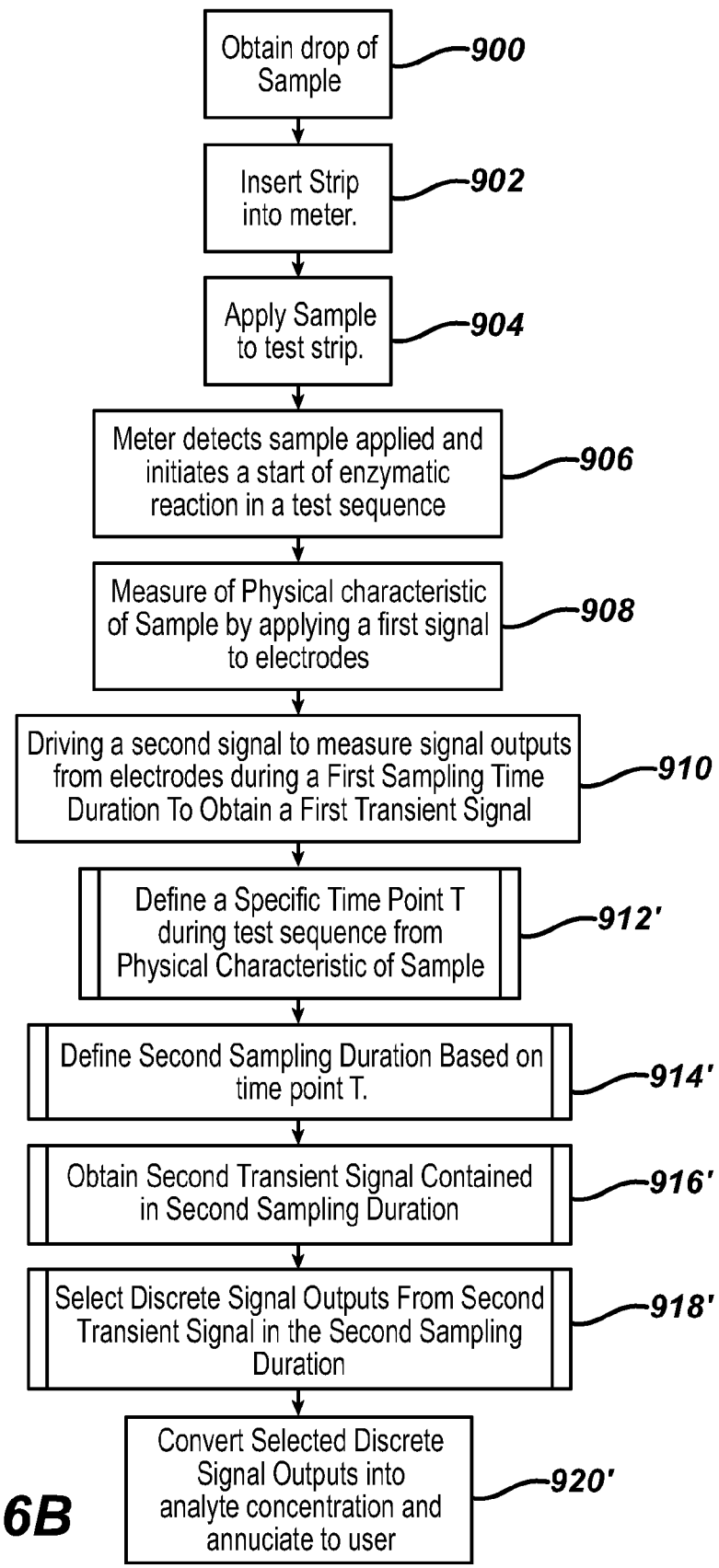
FIG. 6B illustrates a variation on the logical process of FIG. 6A.

With reference to FIG. 6B, a refinement of the method of FIG. 6A is discussed. Steps 900-910 are the same as discussed with reference to FIG. 6A and therefore are not repeated for brevity. At step 912', a specific sampling time T in the first sampling time duration is defined based on the physical characteristic of the sample. A second sampling duration time is defined based on the specific sampling time T in step 914'. A second transient signal (1002a' in FIG. 7D) that is obtained by deleting magnitudes of the first transient signal 1002a (FIG. 7C) that are outside of the specific time range T1-T2 in FIG. 7D. By this process, a second transient signal (1002a' in FIG. 7D) is obtained from the first transient signal (1002a in FIG. 7C). As shown in FIG. 7D, the specific time range T1 to T2 includes specific sampling time T. In particular, T1 is about equal to the difference between the specific sampling time T and a predetermined time A and T2 is about equal to specific sampling time T. In another embodiment, T1 is about equal to an absolute value of the difference of specific sampling time T and A, and where T2 is about equal to T. In the preferred embodiments, A is approximately 4.2 seconds. With reference to step 920 in FIG. 6A or 6B, analyte concentration may be determined in step 920 by application of certain selected magnitudes of the second transient signal (e.g., 1002a') in various mathematical algorithms derived by applicant based on a large amount of known analyte concentrations, as actually measured, as compared to laboratory referential analyte concentrations which are referred to herein as referential or datum values for determining accuracy of the known analyte concentration. In particular, a first algorithm may utilize five different magnitudes of the second transient to arrive at the analyte concentration (G). The magnitudes of second transient signal are typically quoted in nA, thus the intercept is typically quoted in nA, and the slope is typically quoted in nA/(mg/dL), giving analyte concentration in mg/dL. The first analyte concentration algorithm is represented here as Equation 5:

$$G = \frac{\left(\left|\frac{I_3}{I_4}\right|\right)^{x_1} \times \left(\frac{|I_2| + x_4|I_5| - x_5|I_1|}{|I_2| + x_4|I_5|}|I_5|\right) - x_2}{x_3} \quad \text{Eq. 5}$$

where:
- $I_1$ = magnitude of signal at interval 17 (approximately 3.3 seconds from T1);
- $I_2$ = magnitude of signal at interval 13 (approximately 2.5 seconds from start time T1);
- $I_3$ = magnitude of signal at interval 5 (approximately 0.9 seconds from start time T1);
- $I_4$ = magnitude of signal at interval 3 (approximately 0.5 seconds from start time T1);
- $I_5$ = magnitude of signal at interval 22 (approximately 4.3 seconds from start time T1);
- $x_1 = 0.7503$, $x_2 = 337.27$, $x_3 = (-)16.811$, $x_4 = 1.4128$, $x_5 = 2.6707$, wherein, as noted above, the magnitudes of second transient signal may be quoted in nA, $x_2$ may be quoted in nA, and $x_3$ may be quoted in nA/(mg/dL).

In a second variation of the algorithm, only two magnitudes of the extracted second transient signal may be used to determine the analyte concentration (G), which in this case is glucose. The second algorithm is represented by Eq. 6:

$$G = \frac{x_1(|I_1|)^{\left(x_2 - \frac{x_3}{|I_2|}\right)} - x_4}{x_5} \quad \text{Eq. 6}$$

where:
- $I_1$ = magnitude of signal at interval 11 (approximately 2.1 seconds from start time T1);
- $I_2$ = magnitude of signal at interval 7 (approximately 1.3 seconds from start time T1);
- $x_1 = 0.5865$, $x_2 = 2.5099$, $x_3 = (-)12.738$, $x_4 = (-)188.31$, $x_5 = 9.1996$, wherein, as noted above, the magnitudes of second transient signal may be quoted in nA, $x_4$ may be quoted in nA, and $x_5$ may be quoted in nA/(mg/dL).

In a third variation of the algorithm, only three magnitudes of the second transient signal may be used to determine the analyte concentration (G), which in this case is glucose. The third algorithm is represented by Eq. 7:

$$G = \frac{x_1 \ln\left(x_2 \left|\frac{I_1}{I_2}\right|\right)^{x_3} |I_3|^{x_4} - x_5}{x_6} \quad \text{Eq. 7}$$

where:
- $I_1$ = magnitude of signal at interval 20 (approximately 3.9 seconds from start time T1);
- $I_2$ = magnitude of signal at interval 22 (approximately 4.3 seconds from start time T1);
- $I_3$ = magnitude of signal at interval 19 (approximately 3.7 seconds from start time T1);
- $x_1 = 20.154$, $x_2 = 1.0446$, $x_3 = 0.9546$, $x_4 = 1.3894$, $x_5 = 00.7141$, $x_6 = 0.1163$, wherein, as noted above, the magnitudes of second transient signal may be quoted in nA, $x_5$ may be quoted in nA, and $x_6$ may be quoted in nA/(mg/dL).

In a fourth variation of the algorithm, five magnitudes of the second transient signal may be used to determine the analyte concentration (G), which in this case is glucose. The fourth algorithm is represented by Eq. 8:

$$G = \frac{x_3 \left|\frac{I_1}{I_2}\right|^{\left(x_1 - x_2 \left|\frac{I_3}{I_4}\right|\right)} \times |I_5| - x_5}{x_4} \quad \text{Eq. 8}$$

where:
- $I_1$ = magnitude of signal at interval 5 (approximately 0.9 seconds from start time T1);
- $I_2$ = magnitude of signal at interval 1 (approximately 0.1 seconds from start time T1);
- $I_3$ = magnitude of signal at interval 2 (approximately 0.3 seconds from start time T1);
- $I_4$ = magnitude of signal at interval 10 (approximately 1.9 seconds from start time T1);
- $I_5$ = magnitude of signal at interval 22 (approximately 4.3 seconds from start time T1);
- $x_1 = 0.7060$, $x_2 = 0.4864$, $x_3 = 28.5946$, $x_4 = 0.6979$, $x_5 = 15.5099$, wherein, as noted above, the magnitudes of second transient signal may be quoted in nA, $x_5$ may be quoted in nA, and $x_4$ may be quoted in nA/(mg/dL).

In a fifth variation of the algorithm, four magnitudes of the second transient signal may be used to determine the analyte concentration (G), which in this case is glucose. The fifth algorithm is represented by Eq. 9:

$$G = \frac{\left(\left|\frac{I_1}{I_2}\right|^{x_1} \times \frac{x_2|I_3|^2 + x_3|I_3| + x_4}{x_5|I_4| + x_6}\right) - x_7}{x_8} \qquad \text{Eq. 9}$$

where:
- $I_1$ = magnitude of signal at interval 19 (approximately 3.7 seconds from start time T1);
- $I_2$ = magnitude of signal at interval 16 (approximately 3.1 seconds from start time T1);
- $I_3$ = magnitude of signal at interval 11 (approximately 2.1 seconds from start time T1);
- $I_4$ = magnitude of signal at interval 5 (approximately 0.9 seconds from start time T1);
- $x_1 = (-)1.6842$, $x_2 = 0.9527$, $x_3 = (-)4.9724$, $x_4 = 6.2936$, $x_5 = 3.0770$, $x_6 = (-)5.8427$, $x_7 = (-)0.4714$, $x_8 = 0.0079$,
- wherein, as noted above, the magnitudes of second transient signal may be quoted in nA, $x_7$ may be quoted in nA, and $x_8$ may be quoted in nA/(mg/dL).

In a sixth variation of the algorithm, four magnitudes of the second transient signal may be used to determine the analyte concentration (G), which in this case is glucose. The sixth algorithm is represented by Eq. 10:

$$G = \frac{\left(\left|\frac{I_1}{I_2}\right|^{x_1} \times \frac{x_2|I_3|^3 + x_3|I_3|^2 + x_4|I_3| + x_5}{x_6|I_4|^2 + x_7|I_4| + x_8}\right) - x_9}{x_{10}} \qquad \text{Eq. 10}$$

where:
- $I_1$ = magnitude of signal at interval 16 (approximately 3.1 seconds from start time T1);
- $I_2$ = magnitude of signal at interval 5 (approximately 0.9 seconds from start time T1);
- $I_3$ = magnitude of signal at interval 12 (approximately 2.3 seconds from start time T1);
- $I_4$ = magnitude of signal at interval 14 (approximately 2.7 seconds from start time T1);
- $x_1 = 1.1842$, $x_2 = 0.9740$, $x_3 = (-)11.316$, $x_4 = 38.763$, $x_5 = (-)39.319$, $x_6 = 0.0928$, $x_7 = (-)0.8503$, $x_8 = 1.7545$, $x_9 = (-)9.3804$, $x_{10} = 0.2465$,
- wherein, as noted above, the magnitudes of second transient signal may be quoted in nA, $x_9$ may be quoted in nA, and $x_{10}$ may be quoted in nA/(mg/dL).

It is noted that each of the current outputs (e.g., $I_1$, $I_2$, $I_3$, $I_4$, $I_5$) in Equations 5-10 being measured can be a current output from one working electrode in a biosensor that has one working electrode or where there is more than one working electrode, a sum of current outputs from the plurality of working electrodes in a biosensor with plural working electrodes. In the exemplary embodiments, each of the current outputs at the specified sampling time points (e.g., $I_1$, $I_2$, $I_3$, $I_4$, $I_5$) is a total of or a sum of the current outputs from working electrodes 12 and 14 of exemplary biosensor 100. For example, in Equation 10, if the current output for first working electrode at the sixteenth interval (at ~3.1 secs) is 120 nanoamperes and the current output at the second working electrode is 150 nanoamperes at the same interval (~3.1 secs), the magnitude of $I_1$ is the sum of both values and therefore 270 nanoamperes. Similarly, the current output of $I_2$ is the sum of the current output from first working electrode 12 at the fifth interval (~0.9 sec) and the current output from second working electrode 14 at the fifth interval. The remainder of the currents are obtained in the same manner for Equation 10.

Instead of a total current summed from each working electrode for each sampling time, an average of the current from each working electrode at each sampling time can be used in the Equations 5-10 described herein, and of course, with appropriate modification to the operational coefficients (as known to those skilled in the art) to account for a lower measured current at each sampling time than as compared to an embodiment where the measured currents at each sampling time point are added together. Alternatively, the average of the measured currents at each sampling time required by Equations 5-10 can be multiplied by two and used without the necessity of deriving the operational coefficients as in the prior example.

Figure 8B:
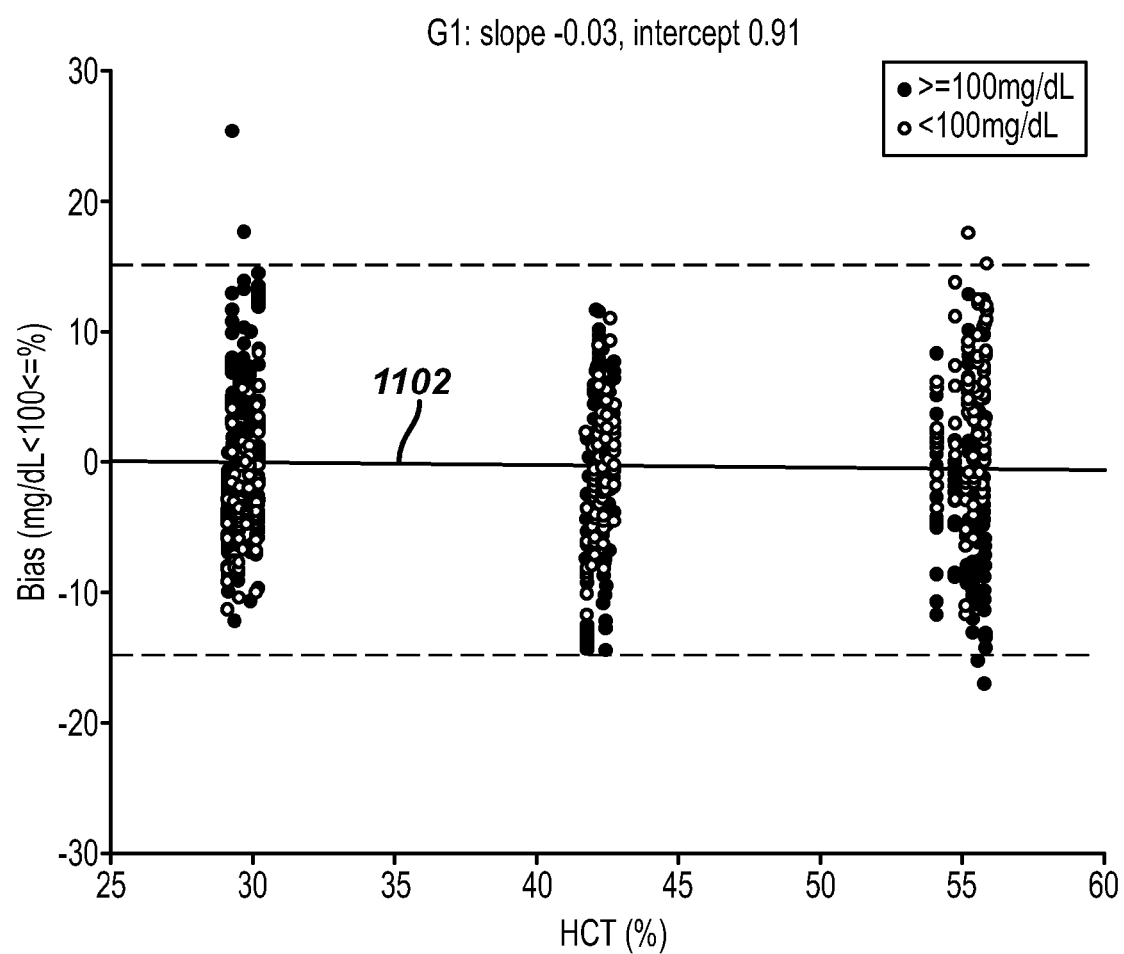
FIGS. 8B, 8C, 8D, 8E, 8F, and 8G illustrate data from test measurements conducted with variations of the exemplary technique herein such that the data show the bias of less than ±15% for the hematocrit range of about 30% to about 55% while attainting relatively little variations in bias for hematocrits at extreme values.
Figure 8C:
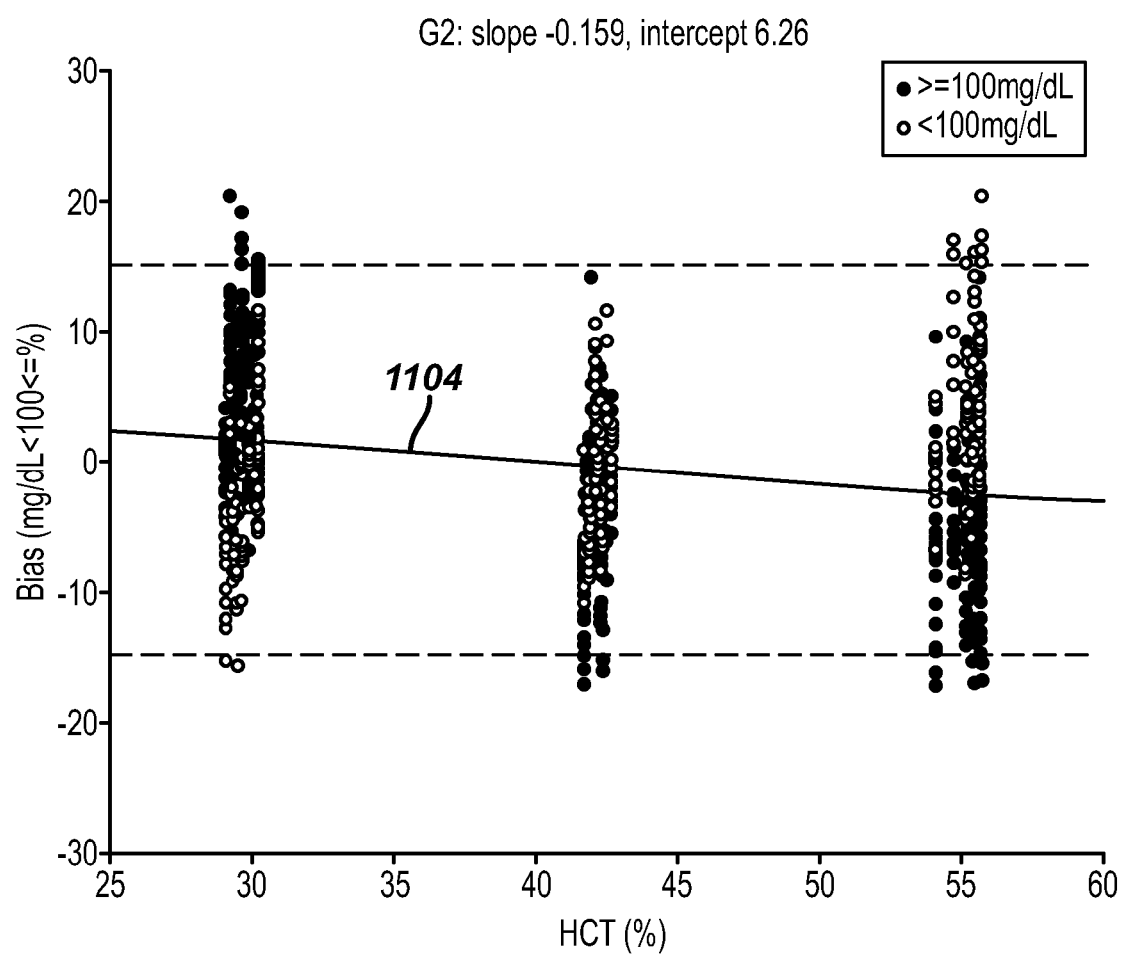
Figure 8D:
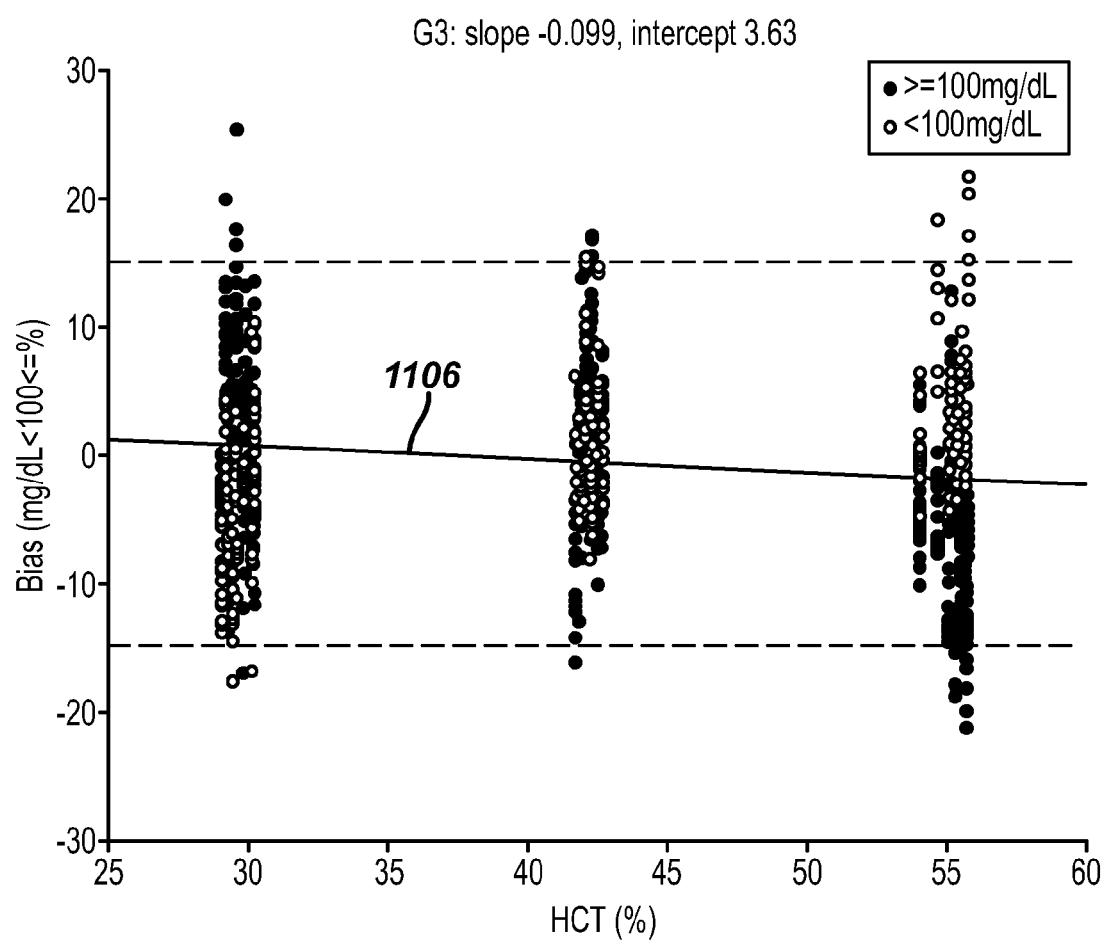
Figure 8E:
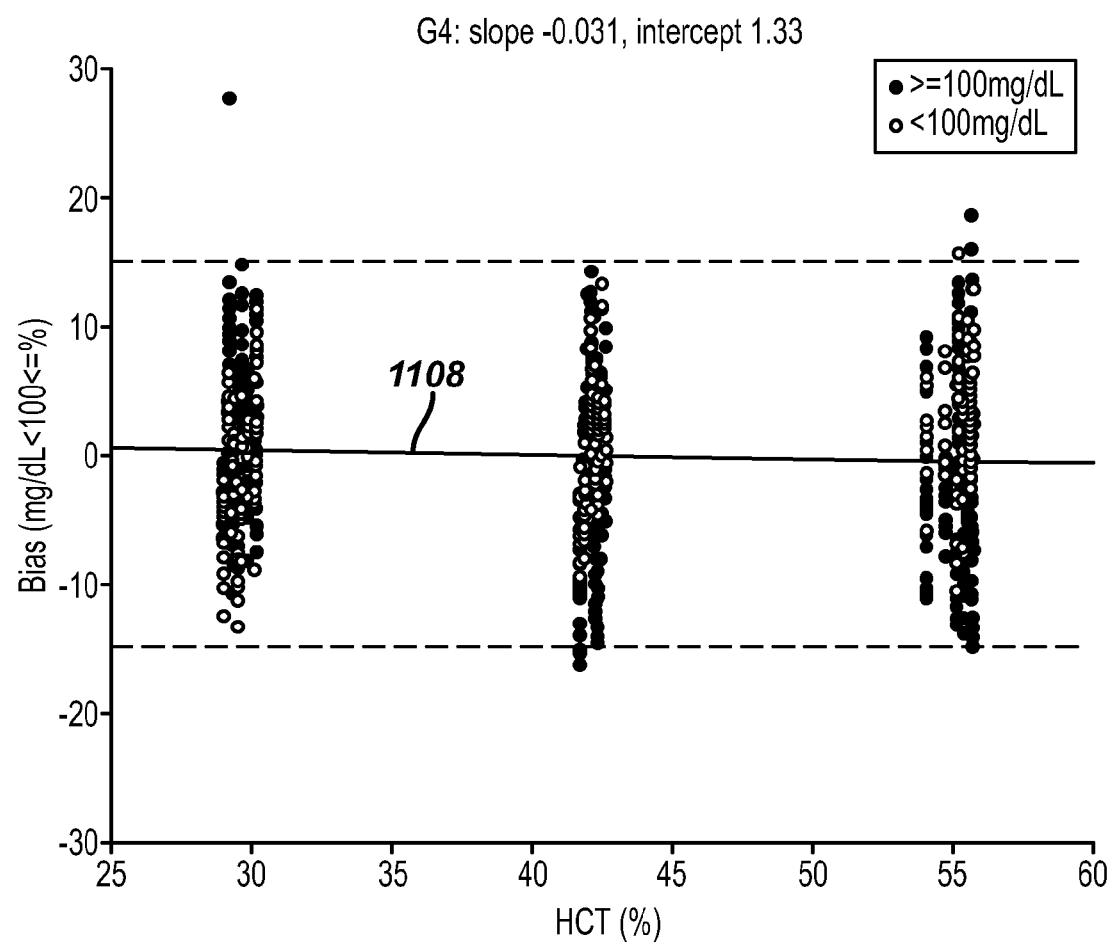
Figure 8F:
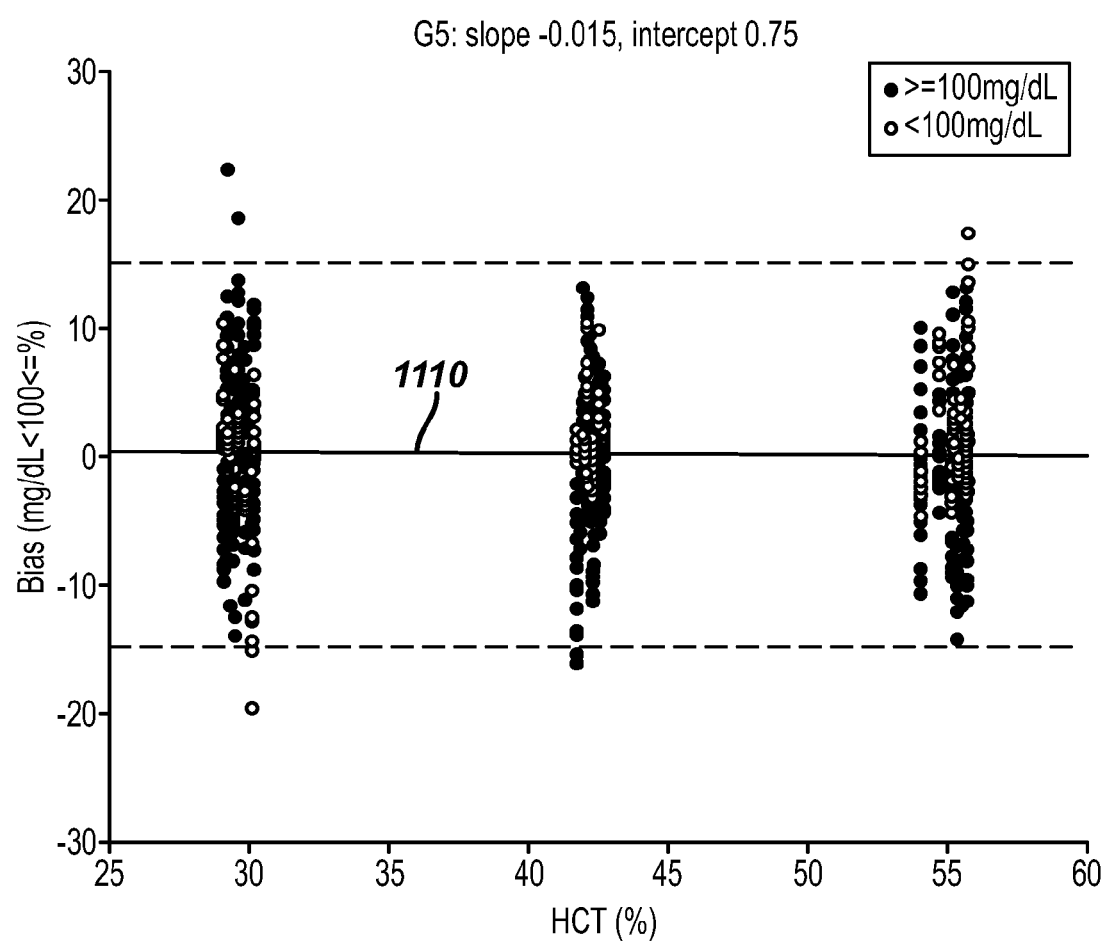
Figure 8G:
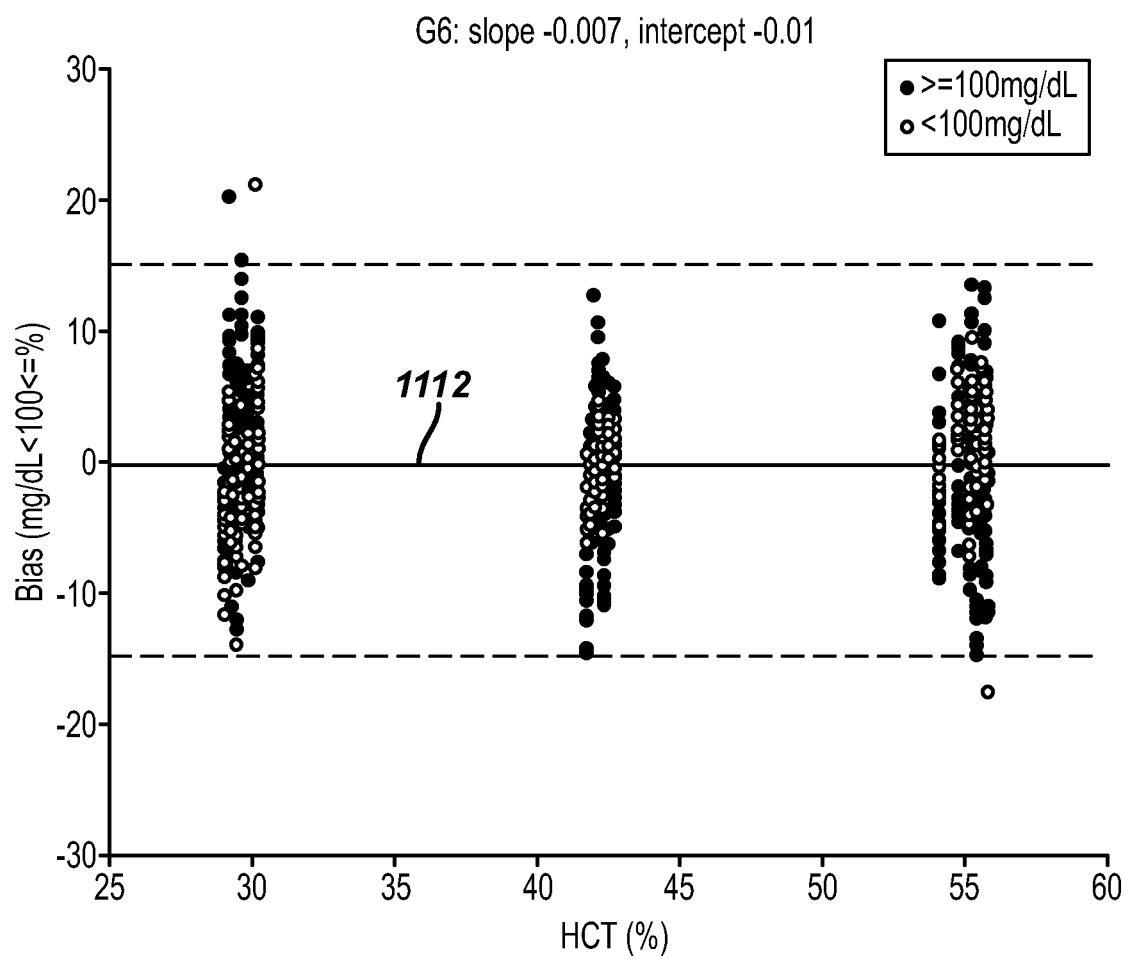

Thus, as another benefit of the teaching provided herein, an increased accuracy of an analyte test measurement is heretofore is achieved as compared to the known technique which provides for a higher bias or error of ±20% for hematocrits of 30%, 42% and 55%, shown here in FIG. 8A in the known test strips. Specifically, a method is provided in which a batch of test strips is provided, typically in a batch of about 845 samples (and in some cases up to 1 million samples (or test strips) per batch), introducing a referential sample containing a referential concentration of an analyte to each test strip of the batch to initiate a test sequence. The method involves reacting the analyte to cause a physical transformation of the analyte with the reagent between the two electrodes, determining a physical characteristic of the referential sample, selecting specific multiple sampling time points that are generally unaffected by the physical characteristic and determining an analyte concentration based on the multiple specific sampling time points such that at least 95% of the analyte concentration values of the batch of test strips are within ±15% of the referential analyte concentration for the range of hematocrit from about 30% to about 55% hematocrit (e.g. about 42% hematocrit), shown here in FIGS. 8B, 8C, 8D, 8E, 8F, and 8G.

In each of FIGS. 8A-8G, experiments were performed with a batch of strips (in this case about 845 strip samples) to quantify the improvement in the glucose measurements from the methods described herein. The quantification of the improvement can be shown by the "bias" at different levels of hematocrit. The bias, which is an estimate of the relative error in the glucose measurement, was calculated for each glucose concentration determined with the methods described herein. The bias for each glucose concentration was determined with equations of the form:

$$\text{Bias}_{abs} \approx G_{calculated} - G_{reference} \text{ for}$$

$$G_{reference} \text{ less than 100 mg/dL glucose and}$$

$$\text{Bias}_\% = \frac{G_{calculated} - G_{reference}}{G_{reference}} \text{ for}$$

$$G_{reference} \text{ greater than or equal to 100 mg/dL glucose}$$

where $\text{Bias}_{abs}$ is absolute bias,
- $\text{Bias}_\%$ is percent bias,
- $G_{calculated}$ is the glucose concentration determined by the method herein and
- $G_{reference}$ is the reference glucose concentration.

In FIG. 8A, when the results are plotted for error or bias in the known test strips, the glucose concentrations at low hematocrits (30%) show a substantial bias of greater than 20% for glucose concentration at 100 mg/dL or greater concentrations. At the other range of hematocrit (55%), the bias again is substantially high for glucose concentrations of 100 mg/dL or greater.

In sharp contrast, when the techniques of the present invention are applied, it can be seen in FIGS. 8B, 8C, 8D, 8E, 8F, and 8G that glucose concentrations at extremes of hematocrits (30% or 55%) are now within the bias of +15% and −15% regardless of whether the glucose concentration is 100 mg/dL or higher.

Plotting the centroids of the glucose data against hematocrits, it can be seen that the centroids of the data define a line 1100 extending between the centroids for glucose concentrations at 30%, 42% and 55% hematocrit. Line 1100 shows a negative slope thereby indicating the variations in bias of the results at low hematocrit (30%) to high hematocrit (55%). Surprisingly, for the embodiments provided herein, it can be seen in these FIGS. 8B, 8C, 8D, 8E, 8F and 8G that the centroids of the glucose concentration data are generally flat at zero bias regardless of the hematocrit parameters of 30%, 42% or 55%. Specifically, with respect to FIG. 8B, which uses Equation 5 as part of inventor's first new technique, line 1102 connecting the centroids of glucose data for low, medium and high hematocrits is virtually horizontal or flat. With respect to FIG. 8C, which uses Equation 6 as part of the inventor's second new technique, line 1104 connecting the centroids of the data at the three hematocrit parameters is not quite as flat as line 1102. Nevertheless, the slope of line 1104 is almost insignificant when compared to line 1100 of the known technique in FIG. 8A. With respect to FIG. 8D, which uses Equation 7 as part of the inventor's third technique to determine the glucose concentrations, line 1106 connecting the centroids of the data is again not quite as flat as line 1102 of FIG. 8B. Nevertheless, the slope of line 1106 (FIG. 8D) is almost insignificant when compared to line 1100 of the known technique (FIG. 8A). With respect to FIG. 8E, which uses Equation 8 as part of the inventor's fourth new technique to determine the glucose concentrations, line 1108 connecting the centroids of the data is virtually flat, indicating that variations in bias between extremes of hematocrit are virtually insignificant. With respect to FIGS. 8F and 8G, which use respective Equations 9 and 10 as part of the inventor's respective fifth and sixth new techniques, the line (1110 or 1112) connecting the centroids of the glucose concentration data (for each of the FIGS. 8F and 8G) is also virtually flat for each of these figures.

Applicant notes that the equations presented above which result in generation of glucose results $G_1$-$G_6$ (in respective FIGS. 8B-8G) were generated using test strip 100 (as shown generally in FIGS. 3A(1), 3A(5) and 3A(6)). If a test strip is used with differing sizes of the various electrodes (including the working electrodes), the division parameter (e.g. $x_{10}$ in equation 10) must be adjusted by measuring the current outputs specific to the respective sizes of the strips and conducting regression analysis of the current outputs for adjustment of the division parameters.

Applicant further notes that while all six equations are equivalent in terms of returning an accurate glucose concentration result, they have they strong and weak points. A combination of these equations may be used to cover optimal performance across different ranges. For example, Equation 10 may be used for low glucose concentration and Equation 5 for high glucose concentration. Alternatively, some or all of the equations may be utilized together in various permutations to allow for a derivation of a glucose concentration that account for large variations in glucose values depending on the operating parameters.

Although the techniques described herein have been directed to determination of glucose, the techniques can also applied to other analytes (with appropriate modifications by those skilled in the art) that are affected by physical characteristic(s) of the fluid sample in which the analyte(s) is disposed in the fluid sample. For example, the physical characteristic (e.g., hematocrit, viscosity, temperature or density) of a blood sample could be accounted for in determination of ketone or cholesterol in the blood sample. Other biosensor configurations can also be utilized. For example, the biosensors shown and described in the following US patents can be utilized with the various embodiments described herein: U.S. Pat. Nos. 6,179,979; 6,193,873; 6,284,125; 6,413,410; 6,475,372; 6,716,577; 6,749,887; 6,863,801; 6,890,421; 7,045,046; 7,291,256; 7,498,132, all of which are incorporated by reference in their entireties herein.

As is known, the detection of the physical characteristic does not have to be done by alternating signals but can be done with other techniques. For example, a suitable sensor can be utilized (e.g., US Patent Application Publication No. 20100005865 or EP1804048 B1) to determine the viscosity or other physical characteristics. Alternatively, the viscosity can be determined and used to derive for hematocrits based on the known relationship between hematocrits and viscosity as described in "Blood Rheology and Hemodynamics" by Oguz K. Baskurt, M. D., Ph.D., 1 and Herbert J. Meiselman, Sc.D., *Seminars in Thrombosis and Hemostasis*, volume 29, number 5, 2003.

As described earlier, the microcontroller or an equivalent microprocessor (and associated components that allow the microcontroller to function for its intended purpose in the intended environment such as, for example, the processor 300 in FIG. 2B) can be utilized with computer codes or software instructions to carry out the methods and techniques described herein. Applicant notes that the exemplary microcontroller 300 (along with suitable components for functional operation of the processor 300) in FIG. 2B is embedded with firmware or loaded with computer software representative of the logic diagrams in FIG. 6A or 6B and the microcontroller 300, along with associated connector 220 and interface 306 and equivalents thereof, are the means for: (a) determining a specified sampling time based on a sensed or estimated physical characteristic of a sample deposited on a plurality of electrodes of the test strip, the specified sampling time being at least one time point or interval referenced from a start of a test sequence upon deposition of a sample on the test strip; (b) applying a second signal to the plurality of electrodes to measure a first transient output signal from the plurality of electrodes due to application of the second signal to the plurality of electrodes; (c) extracting a second transient output signal from the first output signal; (d) determining a magnitude of the second transient output signal over a plurality of discrete time intervals; and (e) calculating the analyte concentration from the magnitudes of the second transient output signal at selected intervals of the plurality of discrete time intervals.

The means for calculating may include a microprocessor programmed to calculate the analyte concentration with any one of Equations 5-10, along with their respective parameters, as described earlier.

A short discussion of the embodiments of the meter for the present disclosure is warranted here. In particular, in general, hand-held test meters for use with an analytical test strip in the determination of an analyte (such as glucose) in a bodily fluid sample (i.e., a whole blood sample) according to embodiments of the present disclosure include a housing, a microcontroller block disposed in the housing, and a phase-shift-based hematocrit measurement block (also referred to as a phase-shift-based hematocrit circuit). In such hand-held test meters, the phase-shift-based hematocrit measurement block includes a signal generation sub-block, a low pass filter sub-block, an analytical test strip sample cell interface sub-block, a transimpedance amplifier sub-block, and a phase detector sub-block. In addition, the phase-shift-based hematocrit measurement block and microcontroller block are configured to measure the phase shift of a bodily fluid sample in a sample cell of an analytical test strip inserted in the hand-held test meter and the microcontroller block is also configured to compute the hematocrit of the bodily fluid sample based on the measured phase shift.

Hand-held test meters according to embodiments of the present disclosure are beneficial in that they provide improved accuracy of analyte determination (such as glucose determination) in whole blood samples by measuring the hematocrit of the whole blood sample and then employing the measured hematocrit during analyte determination.

One example of a hand-held test meter that can be readily modified as a hand-held test meter according to the present disclosure is the commercially available OneTouch® Ultra® 2 glucose meter from LifeScan Inc. (Milpitas, Calif.). Additional examples of hand-held test meters that can also be modified are found in U.S. Patent Application Publications No's. 2007/0084734 (published on Apr. 19, 2007) and 2007/0087397 (published on Apr. 19, 2007) and in International Publication Number WO2010/049669 (published on May 6, 2010), each of which is hereby incorporated herein in full by reference.

Figure 9:
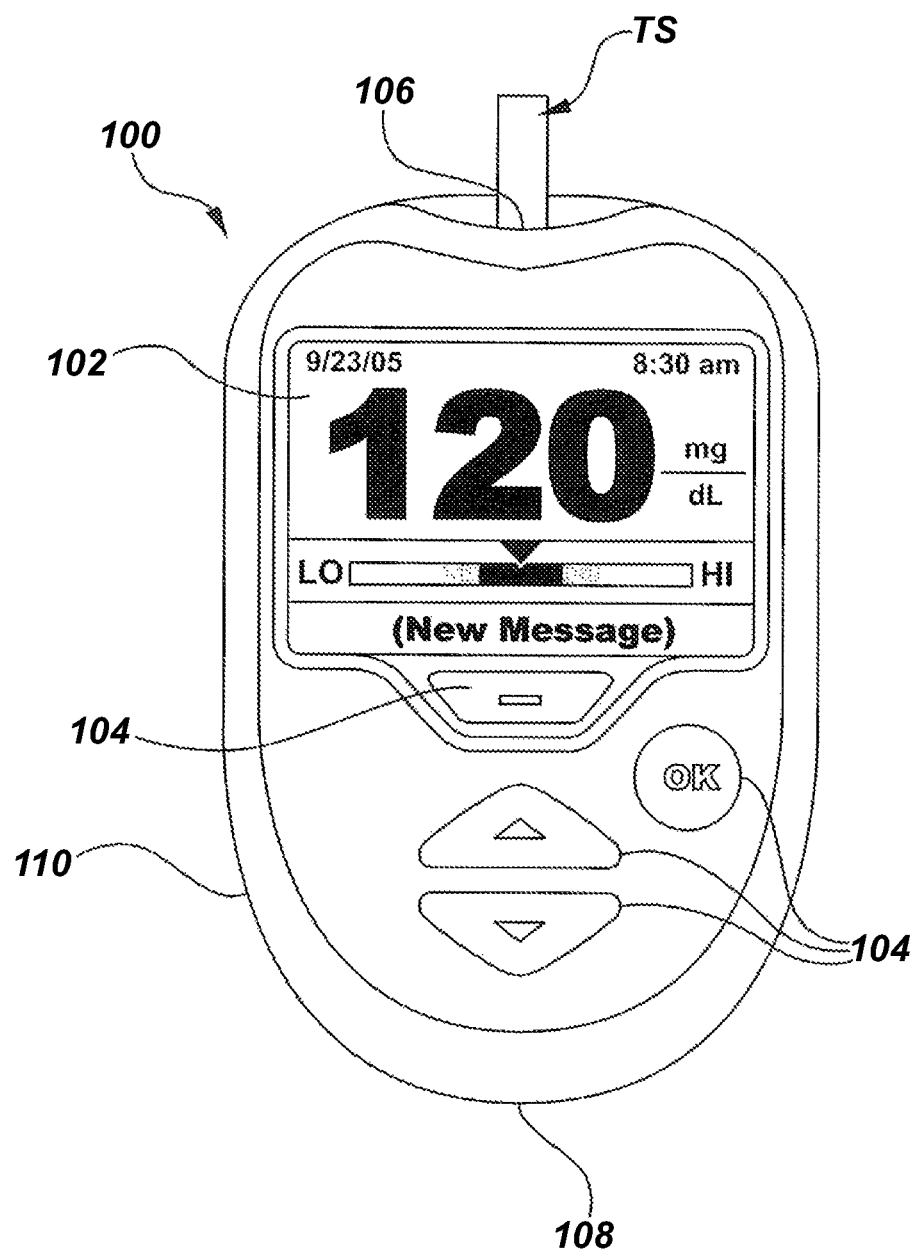
FIG. 9 is a simplified depiction of a hand-held test meter according to an embodiment of the present disclosure.
Figure 10:
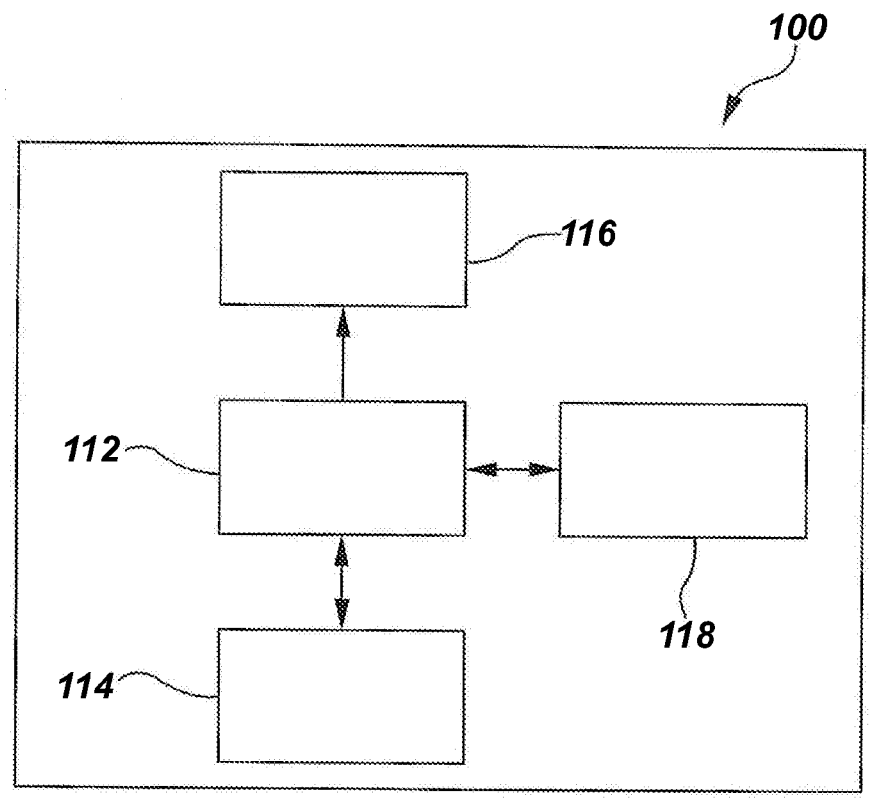
FIG. 10 is a simplified block diagram of various blocks of the hand-held test meter of FIG. 9.
Figure 11:
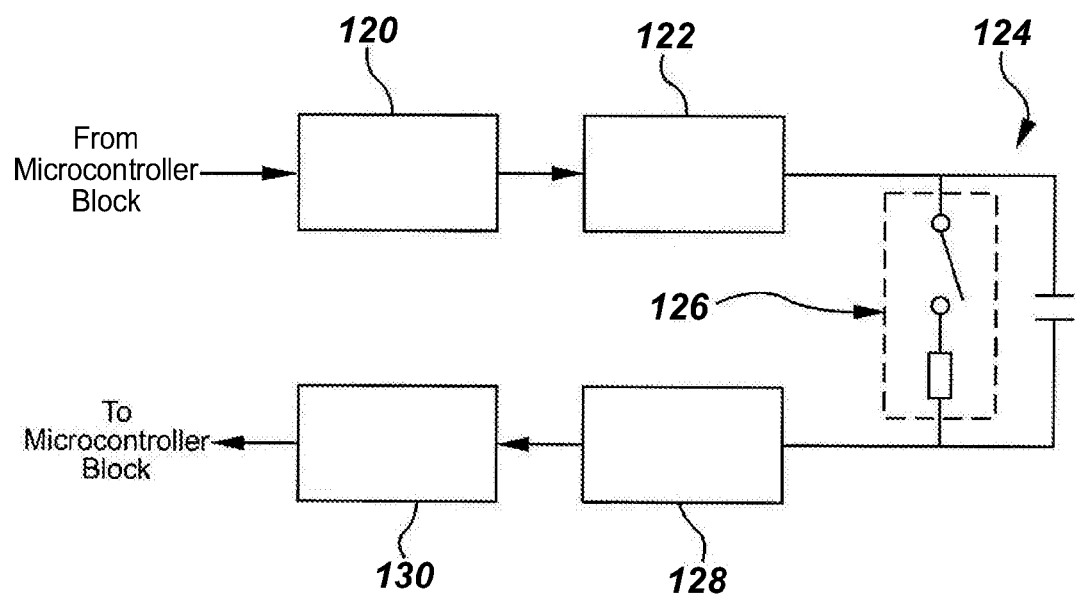
FIG. 11 is a simplified block diagram of a phase-shift-based hematocrit measurement block as can be employed in embodiments according to the present disclosure.
Figure 12:
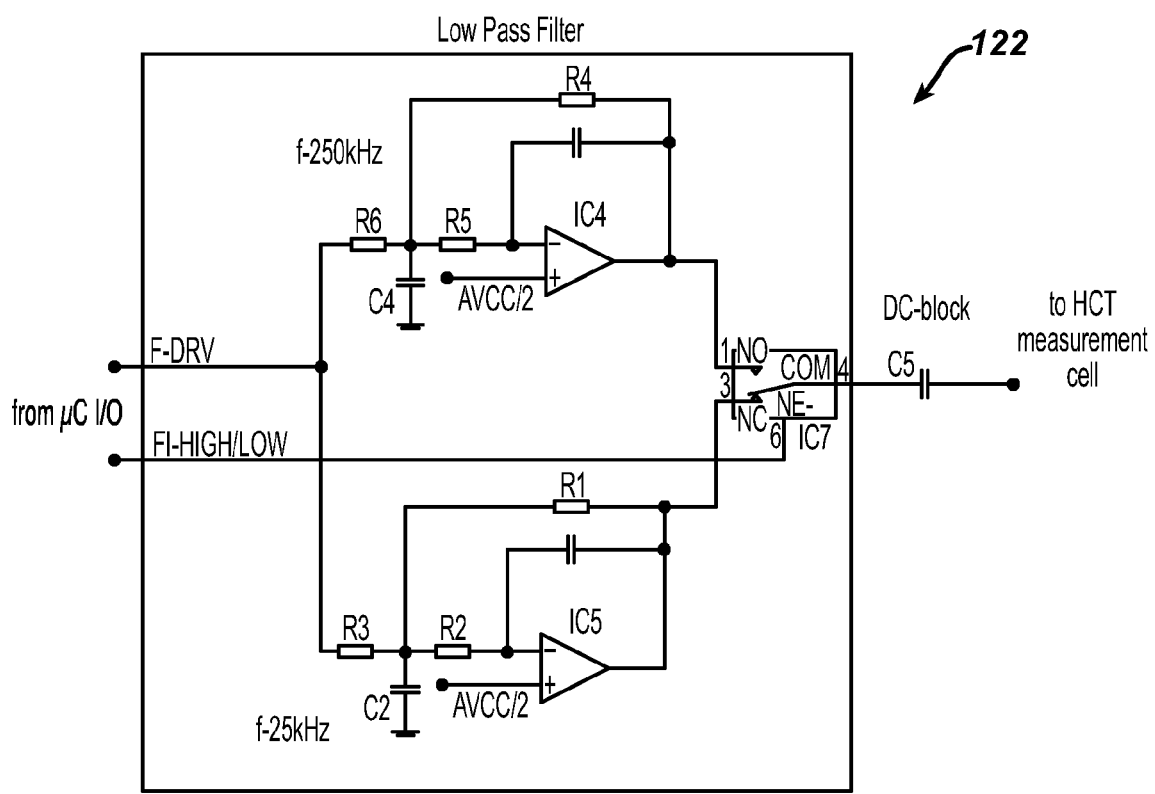
FIG. 12 is a simplified annotated schematic diagram of a dual low pass filter sub-block as can be employed in embodiments of the present disclosure.
Figure 13:
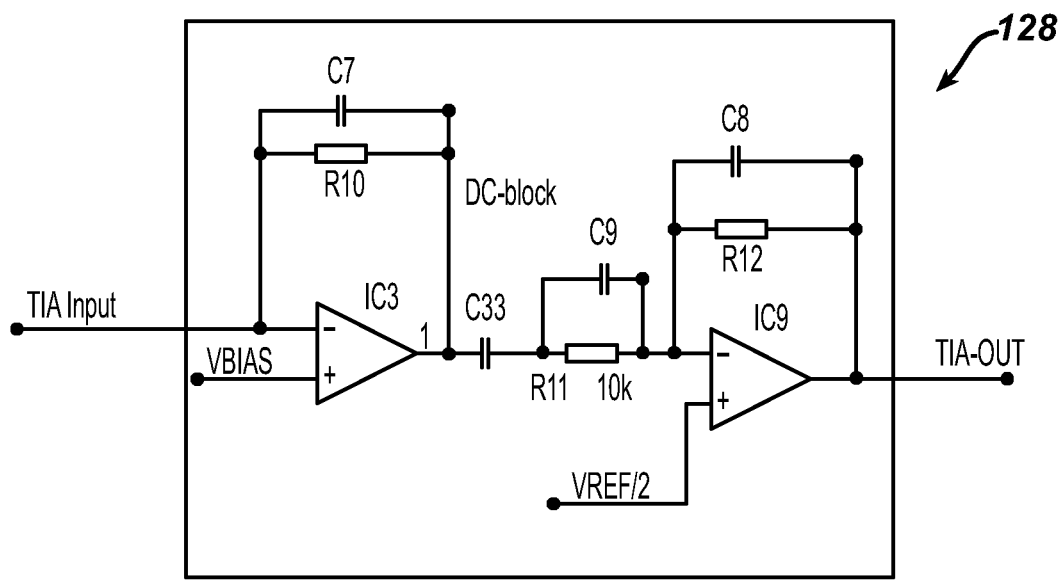
FIG. 13 is a simplified annotated schematic diagram of a transimpedance amplifier (TIA) sub-block as can be employed in embodiments of the present disclosure.
Figure 14:
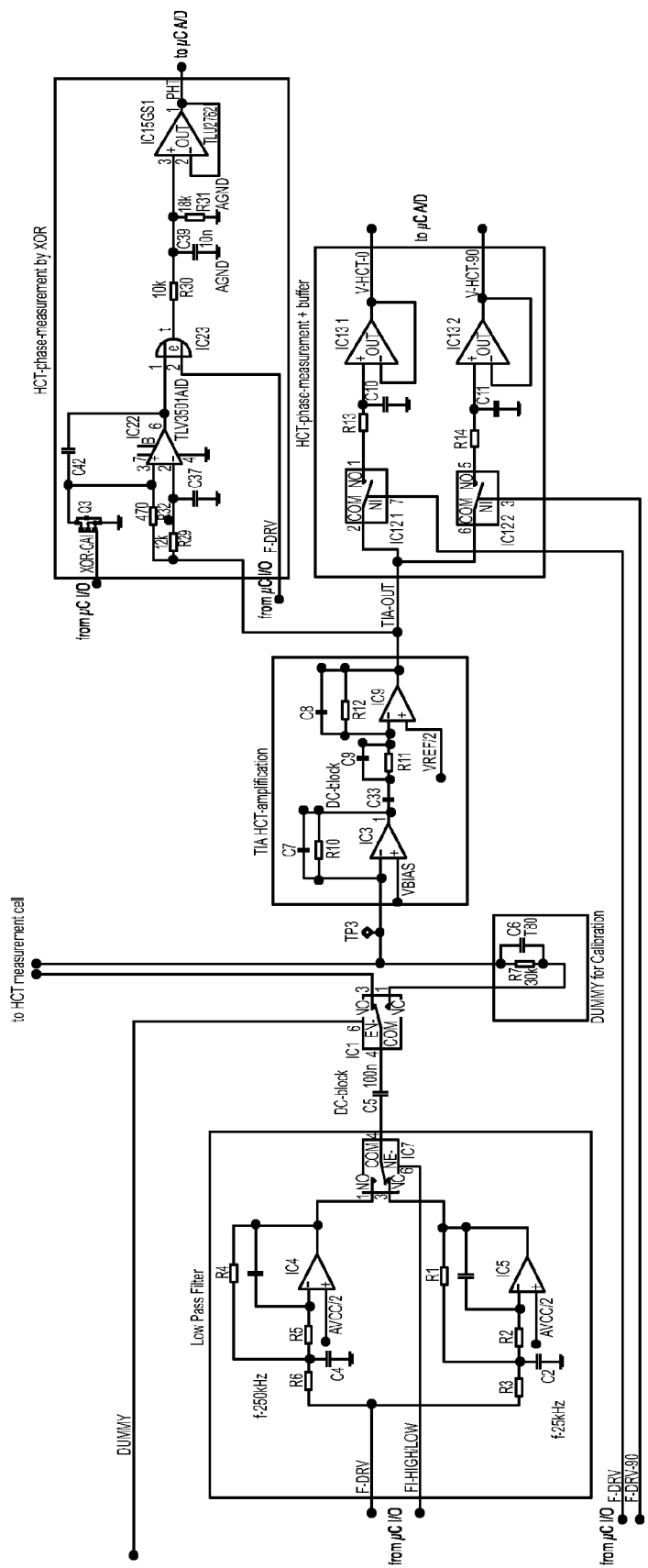
FIG. 14 is a simplified annotated schematic block diagram depicting a dual low pass filter sub-block, a calibration load sub-block, an analytical test strip sample cell interface sub-block, a transimpedance amplifier sub-block, an XOR phase shift measurement sub-block and a Quadratur DEMUX phase-shift measurement sub-block as can be employed in a phase-shift-based hematocrit measurement block of embodiments of the present disclosure.

FIG. 9 is a simplified depiction of a hand-held test meter 100 according to an embodiment of the present disclosure. FIG. 10 is a simplified block diagram of various blocks of hand-held test meter 100. FIG. 11 is a simplified combined block diagram of a phase-shift-based hematocrit measurement block of hand-held test meter 100. FIG. 12 is a simplified annotated schematic diagram of a dual low pass filter sub-block of hand-held test meter 100. FIG. 13 is a simplified annotated schematic diagram of a transimpedance amplifier sub-block of hand-held test meter 100. FIG. 14 is a simplified annotated schematic block diagram of portions of a phase-shift-based hematocrit measurement block of hand-held test meter 100.

Referring to FIGS. 9 through 14, hand-held test meter 100 includes a display 102, a plurality of user interface buttons 104, a strip port connector 106, a USB interface 108, and a housing 110 (see FIG. 9). Referring to FIG. 10 in particular, hand-held test meter 100 also includes a microcontroller block 112, a phase-shift-based hematocrit measurement block 114, a display control block 116, a memory block 118 and other electronic components (not shown) for applying a test voltage to analytical test strip (labeled TS in FIG. 9), and also for measuring an electrochemical response (e.g., plurality of test current values) and determining an analyte based on the electrochemical response. To simplify the current descriptions, the figures do not depict all such electronic circuitry.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with an analytical test strip TS, such as an electrochemical-based analytical test strip configured for the determination of glucose in a whole blood sample. Therefore, the analytical test strip is configured for operative insertion into strip port connector 106 and to operatively interface with phase-shift-based hematocrit measurement block 114 via, for example, suitable electrical contacts.

USB Interface 108 can be any suitable interface known to one skilled in the art. USB Interface 108 is essentially a passive component that is configured to power and provide a data line to hand-held test meter 100.

Once an analytical test strip is interfaced with hand-held test meter 100, or prior thereto, a bodily fluid sample (e.g., a whole blood sample) is introduced into a sample chamber of the analytical test strip. The analytical test strip can include enzymatic reagents that selectively and quantitatively transform an analyte into another predetermined chemical form. For example, the analytical test strip can include an enzymatic reagent with ferricyanide and glucose oxidase so that glucose can be physically transformed into an oxidized form.

Memory block 118 of hand-held test meter 100 includes a suitable algorithm and can be configured, along with microcontroller block 112 to determine an analyte based on the electrochemical response of analytical test strip and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing 110 and can include any suitable microcontroller and/or microprocesser known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (A/D) processing capabilities suitable for measuring voltages generated by phase shift based hematocrit measurement blocks employed in embodiments of the present disclosure.

Referring in particular to FIG. 11, phase-shift-based hematocrit measurement block 114 includes a signal generation sub-block 120, a low pass filter sub-block 122, an analytical test strip sample cell interface sub-block 124, an optional calibration load block 126 (within the dashed lines of FIG. 11), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of an analytical test strip inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

It has been determined that a relationship exists between the reactance of a whole blood sample and the hematocrit of that sample. Electrical modeling of a bodily fluid sample (i.e., a whole blood sample) as parallel capacitive and resistive components indicates that when an alternating current (AC) signal is forced through the bodily fluid sample, the phase shift of the AC signal will be dependent on both the frequency of the AC voltage and the hematocrit of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz. Therefore, the hematocrit of a bodily fluid sample can be measured by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Referring to FIGS. 11 through 14 in particular, signal generation sub-block 120 can be any suitable signal generation block and is configured to generate a square wave (0V to Vref) of a desired frequency. Such a signal generation sub-block can, if desired, be integrated into microcontroller block 112.

The signal generated by signal generation sub-block 120 is communicated to dual low pass filter sub-block 122, which is configured to convert the square wave signal to a sine wave signal of a predetermined frequency. The dual LPF of FIG. 12 is configured to provide both a signal of a first frequency (such as a frequency in the range of 10 kHz to 25 kHz) and a signal of a second frequency (such as a frequency in the range of 250 kHz to 500 kHz) to the analytical test strip sample cell interface sub-block and an analytical test strips' sample chamber (also referred to as the HCT measurement cell). Selection of the first and second frequency is accomplished using switch IC7 of FIG. 12. The dual LPF of FIG. 12 includes employs two suitable operational amplifiers (IC4 and IC5) such as the operational amplifier available from Texas Instruments, Dallas, Tex., USA as high-speed, voltage feedback, CMOS operational amplifier part number OPA354.

Referring to FIG. 12, F-DRV represents a square wave input of either a low or high frequency (e.g., 25 kHz or 250 kHz) and is connected to both IC4 and IC5. Signal Fi-HIGH/LOW (from the microcontroller) selects the output of dual low pass filter sub-block 122 via switch IC7. C5 in FIG. 12 is configured to block the operating voltage of dual low pass filter sub-block 122 from the HCT measurement cell.

Although a specific dual LPF is depicted in FIG. 12, dual low pass filter sub-block 122 can be any suitable low pass filter sub-block known to one skilled in the art including, for example, any suitable multiple feedback low pass filter, or a Sallen and Key low pass filter.

The sine wave produced by low pass filter sub-block 122 is communicated to analytical test strip sample cell interface sub-block 124 where it is driven across the sample cell of the analytical test strip (also referred to as an HCT measurement cell). Analytical test strip sample cell interface block 124 can be any suitable sample cell interface block including, for example, an interface block configured to operatively interface with the sample cell of the analytical test strip via first electrode and second electrodes of the analytical test strip disposed in the sample cell. In such a configuration, the signal can be driven into the sample cell (from the low pass filter sub-block) via the first electrode and picked-up from the sample cell (by the transimpedance amplifier sub-block) via the second electrode as depicted in FIG. 14.

The current produced by driving the signal across the sample cell is picked-up by transimpedance amplifier sub-block 128 and converted into a voltage signal for communication to phase detector sub-block 130.

Transimpedance sub-block 128 can be any suitable transimpedance sub-block known to one skilled in the art. FIG. 13 is a simplified annotated schematic block diagram of one such transimpedance amplifier sub-block (based on two OPA354 operational amplifiers, IC3 and IC9). The first stage of TIA sub-block 128 operates at, for example, 400 mV, which limits the AC amplitude to +/−400 mV. The second stage of TIA sub-block 128 operates at Vref/2, a configuration which enables the generation of an output of the full span of the microcontroller A/D inputs. C9 of TIA sub-block 128 serves as a blocking component that only allows an AC sine wave signal to pass.

Phase detector sub-block 130 can be any suitable phase detector sub-block that produces either a digital frequency that can be read back by microcontroller block 112 using a capture function, or an analog voltage that can be read back by microcontroller block 112 using an analog to digital converter. FIG. 14 depicts a schematic that includes two such phase detector sub-blocks, namely an XOR phase detector (in the upper half of FIG. 14 and including IC22 and IC23) and a Quadrature DEMUX phase detector (in the lower half of FIG. 14 and including IC12 and IC13).

FIG. 14 also depicts a calibration load sub-block 126 that includes a switch (IC16) and a dummy load R7 and C6. Calibration load sub-block 126 is configured for the dynamic measurement of a phase offset for the known phase shift of zero degrees produced by resistor R7, thus providing a phase offset for use in calibration. C6 is configured to force a predetermined slight phase shift, e.g. to compensate for phase delays caused by parasitic capacities in the signal traces to the sample cell, or for phase delays in the electrical circuits (LPF and TIA).

The Quadrature DEMUX phase detector circuit of FIG. 14 includes two portions, one portion for a resistive part of the incoming AC signal and one portion for the reactive portion of the incoming AC signal. Use of such two portions enables the simultaneous measurement of both the resistive and reactive portion of the AC signal and a measurement range that covers 0 degrees to 360 degrees. The Quadrature DEMUX circuit of FIG. 14 generates two separate output voltages. One of these output voltages represents the "in phase measurement" and is proportional to the "resistive" part of the AC signal, the other output voltage represents the "Quadrature Measurement" and is proportional to the "reactive part of the signal. The phase shift is calculated as:

$$\phi = \tan^{-1}(V_{QUAD\text{-}PHASE}/V_{IN\text{-}PHASE})$$

Such a Quadrature DEMUX phase detector circuit can also be employed to measure the impedance of a bodily fluid sample in the sample cell. It is hypothesized, without being bound, that the impedance could be employed along with the phase-shift, or independently thereof, to determine the hematocrit of the bodily sample. The amplitude of a signal forced through the sample cell can be calculated using the two voltage outputs of the Quadrature DEMUX circuit as follows:

$$\text{Amplitude} = SQR((V_{QUAD\text{-}PHASE})^2 + (V_{IN\text{-}PHASE})^2)$$

This amplitude can then be compared to an amplitude measured for the known resistor of calibration load block 126 to determine the impedance.

The XOR phase detector portion has a measurement range of 0° to 180°, or alternatively a measurement range of −90° to +90°, depending whether the "Square wave input from μC" is in phase to the sine wave or is set to a 90° phase shift. The XOR phase detector produces an output frequency that is always double the input frequency, however the duty cycle varies. If both inputs are perfectly in phase, the output is LOW, if both inputs are 180° shifted the output is always HIGH. By integrating the output signal (e.g. via a simple RC element) a voltage can be generated that is directly proportional to the phase shift between both inputs.

Once apprised of the present disclosure, one skilled in the art will recognize that phase detector sub-blocks employed in embodiments of the present disclosure can take any suitable form and include, for example, forms that employ rising edge capture techniques, dual edge capture techniques, XOR techniques and synchronous demodulation techniques.

Since low pass filter sub-block 122, transimpedance amplifier sub-block 128 and phase detector sub-block 130 can introduce a residual phase shift into phase-shift-based hematocrit measurement block 114, calibration load block 126 can be optionally included in the phase-shift-based hematocrit measurement block. Calibration load block 126 is configured to be essentially resistive in nature (for example a 33 k-ohm load) and, therefore, induces no phase shift between excitation voltage and generated current. Calibration load block 126 is configured to be switched in across the circuit to give a "zero" calibration reading. Once calibrated, the hand-held test meter can measure the phase shift of a bodily fluid sample, subtract the "zero" reading to compute a corrected phase shift and subsequently compute the bodily sample hematocrit based on the corrected phase shift.

Figure 15:
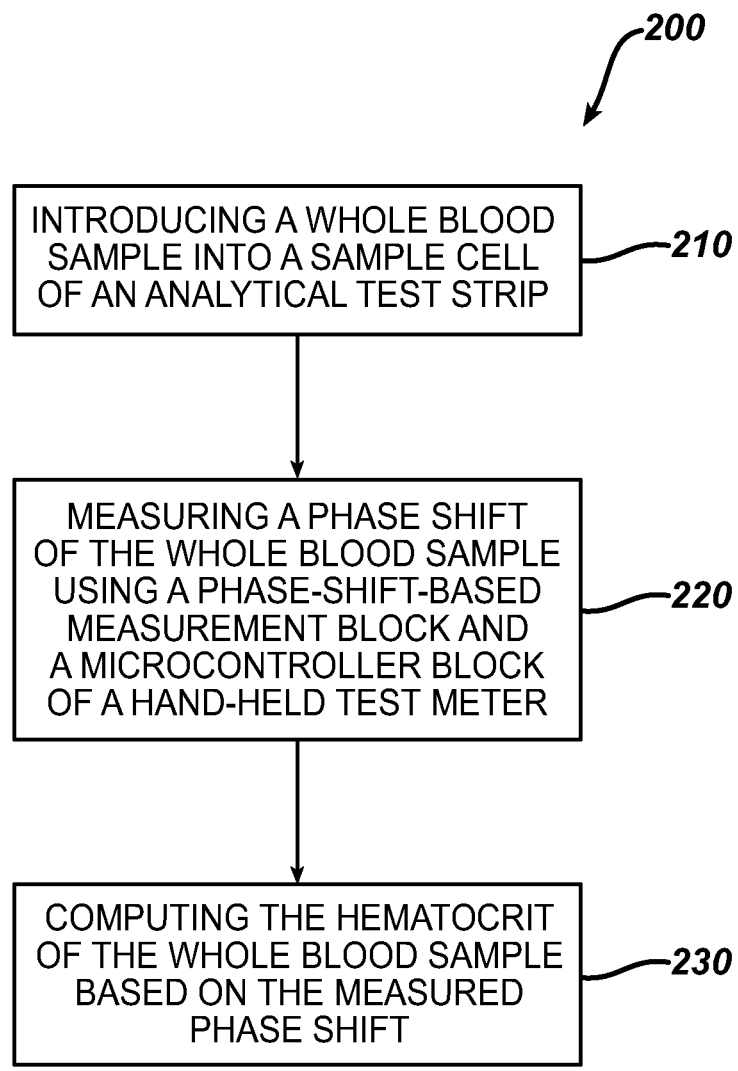
FIG. 15 is a flow diagram depicting stages in a method for employing a hand-held test meter according to an embodiment of the present disclosure.

FIG. 15 is a flow diagram depicting stages in a method 200 for employing a hand-held test meter and analytical test strip (e.g., an electrochemical-based analytical test strip). Method 200, at step 210, includes introducing a whole blood sample into a sample cell of the analytical test strip.

At step 220, a phase shift of the whole blood sample in the sample cell is measured using a phase-shift-based measurement block and a microcontroller block of a hand-held test meter. Method 200 further includes computing the hematocrit of whole blood sample based on the measured phase shift using the microcontroller block (see step 230 of FIG. 15). Additional details can also be obtained from U.S. patent application Ser. No. 13/250,525, now U.S. Pat. No. 8,623,660 and PCT/GB2012/052421, all of which are incorporated by reference as if set forth herein this application.

Moreover, while the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the invention found in the claims, it is the intent that this patent will cover those variations as well.

The invention claimed is:

1. A method of determining an analyte concentration from a physiological sample with a biosensor having at least two electrodes and a reagent disposed on at least one electrode of the electrodes, the method comprising:
depositing a physiological sample on any one of the at least two electrodes to start an analyte test sequence;
applying a first signal to the sample to derive a physical characteristic of the sample;
driving a second signal to the sample for a first sampling time duration that overlaps with the test sequence to obtain a first transient signal output from the sample, the first transient signal correlated to both time and magnitude during the first sampling time duration;
extracting a specific sampling time during the test sequence in the first sampling time duration based on the physical characteristic of the sample, extracting the specific sampling time comprising calculating a defined specific sampling time in the first sampling time duration based on the physical characteristic of the sample;
obtaining from the transient signal a second transient signal over a second sampling time duration, the second sampling time duration defined based on the specific sampling time;
deriving respective magnitudes of the second transient signal at selected time intervals in the second sampling time duration; and
determining an analyte concentration based on respective magnitudes of the second transient signal at the selected time intervals.

2. The method of claim 1, further comprising:
defining the second sampling time duration based on the specific sampling time such that the second sampling time duration overlaps the first sampling time duration; and
dividing the second transient signal into discrete time intervals with respect to the second sampling time duration,
in which the second transient signal is referenced with respect to the second sampling time duration.

3. A method of determining an analyte concentration from a physiological sample with a biosensor having at least two electrodes and a reagent disposed on at least one electrode of the electrodes, the method comprising:
depositing a physiological sample on any one of the at least two electrodes to start an analyte test sequence;
applying a first signal to the sample to derive a physical characteristic of the sample;
extracting a specific sampling time in a first sampling time duration, extracting the specific sampling time comprising calculating a defined specific sampling time in the first sampling time duration based on the physical characteristic of the sample;
driving a second signal into the sample for the first sampling time duration;
measuring or sampling a first transient signal output from the sample for the duration of the first sampling time duration;
defining a specific range of time that includes the specific sampling time in the first sampling time duration,
obtaining plural magnitudes of the first transient signal (i) at respective discrete intervals within the specific range of time or (ii) at about the specific sampling time; and
determining the analyte concentration based on the magnitudes of the first transient signal from the obtaining step.

4. The method of claim 3, further comprising:
defining a specific range of time that includes the specific sampling time in the first sampling time duration, and obtaining plural magnitudes of the first transient signal at respective discrete intervals within the specific range of time.

5. The method of claim 3, further comprising:
obtaining plural magnitudes of the first transient signal output at time intervals other than at about the specific sampling time.

6. The method of claim 1, in which the second sampling time duration includes magnitudes of second transient signal measured before the specific sampling time, and
the specific range of time includes magnitudes of first transient signal measured before the specific sampling time.

7. The method of claim 1, in which the calculating step for the defined specific sampling time comprises utilizing an equation of the form:

$$x_1 = a \times H^2 + bH + c$$

where
"SpecificSamplingTime" is designated as a time point from the start of the test sequence at which to sample the output signal of the biosensor,
H represents physical characteristic of the sample,
$x_1$ is about 4.3e5;
$x_2$ is about (−)3.9; and
$x_3$ is about 4.8.

8. The method of claim 2, in which the step of defining the second sampling time duration comprises obtaining an absolute value of a difference between the defined specific sampling time and a predetermined time point to define a start time (T1) and an end time (T2) approximately equal to the specific sampling time point, and the first sampling time duration comprises about 10 seconds or less from the step of depositing the sample.

9. The method of claim 1, in which the step of obtaining further comprises defining a second sampling time duration that overlaps the first sampling time duration and includes a portion of the first transient signal and its magnitudes with respect to the time of the second sampling time duration, wherein the portion is designated as a second transient signal.

10. The method of claim 8, in which the step of obtaining the second transient signal comprises extracting from the first transient signal a portion of the first transient signal that is designated as a second transient signal that is within the second sampling time duration.

11. The method of claim 10, in which the deriving of respective magnitudes of the second transient signal at discrete selected time intervals comprises calculating a magnitude of the second transient signal during each selected time interval.

12. The method of claim 10, in which the dividing comprises dividing the second transient signal into at least 22 intervals in sequence starting from interval one at about the start time to interval twenty-two at about the end time.

13. The method of claim 11, in which the determination of analyte concentration is obtained by utilizing an equation of the form:

$$G = \frac{\left(\left|\frac{I_3}{I_4}\right|\right)^{x_1} \times \left(\frac{|I_2| + x_4|I_5| - x_5|I_1|}{|I_2| + x_4|I_5|} |I_5|\right) - x_2}{x_3}$$

where:
G is representative of analyte concentration;
$I_1 \approx$ magnitude of second transient signal at interval 17;
$I_2 \approx$ magnitude of second transient signal at interval 13;
$I_3 \approx$ magnitude of second transient signal at interval 5;
$I_4 \approx$ magnitude of second transient signal at interval 3;
$I_5 \approx$ magnitude of second transient signal at interval 22;
$x_1 \approx 0.75$;
$x_2 \approx 337.27$;
$x_3 \approx (-)16.81$;
$x_4 \approx 1.41$; and
$x_5 \approx 2.67$.

14. The method of claim 11, in which the determination of analyte concentration is obtained by utilizing an equation of the form:

$$G = \frac{x_1(|I_1|)\left(x_2 - \frac{x_3}{|I_2|}\right) - x_4}{x_5}$$

where:
G is representative of analyte concentration;
$I_1 \approx$ magnitude of second transient signal at interval 11;
$I_2 \approx$ magnitude of second transient signal at interval 7;
$x_1 \approx 0.59$;
$x_2 \approx 2.51$;
$x_3 \approx (-)12.74$;
$x_4 \approx (-)188.31$; and
$x_5 \approx 9.2$.

15. The method of claim 11, in which the determination of analyte concentration is obtained by utilizing an equation of the form:

$$G = \frac{x_1 \ln\left(x_2 - \frac{|I_1|}{|I_2|}\right)^{x_3} |I_3|^{x_4} - x_5}{x_6}$$

where:
G is representative of analyte concentration;
$I_1 \approx$ magnitude of second transient signal at interval 20;
$I_2 \approx$ magnitude of second transient signal at interval 22;
$I_3 \approx$ magnitude of second transient signal at interval 19;
$x_1 \approx 20.15$;
$x_2 \approx 1.0446$;
$x_3 \approx 0.95$;
$x_4 \approx 1.39$;
$x_5 \approx (-)0.71$; and
$x_6 \approx 0.11$.

16. The method of claim 11, in which the determination of analyte concentration is obtained by utilizing an eauation of the form:

$$G = \frac{x_3 \left|\frac{I_1}{I_2}\right|^{\left(x_1 - x_2 \frac{|I_3|}{|I_4|}\right)} \times |I_5| - x_5}{x_4}$$

where:
G is representative of analyte concentration;
$I_1 \approx$ magnitude of second transient signal at interval 5;
$I_2 \approx$ magnitude of second transient signal at interval 1;
$I_3 \approx$ magnitude of second transient signal at interval 2;
$I_4 \approx$ magnitude of second transient signal at interval 10;
$I_5 \approx$ magnitude of second transient signal at interval 22;
$x_1 \approx 0.70$;
$x_2 \approx 0.49$;
$x_3 \approx 28.59$;
$x_4 \approx 0.7$; and
$x_5 \approx 15.51$.

17. The method of claim 11, in which the determination of analyte concentration is obtained by utilizing an equation of the form:

$$G = \frac{\left(\left|\frac{I_1}{I_2}\right|^{x_1} \times \frac{x_2|I_3|^2 + x_3|I_3| + x_4}{x_5|I_4| + x_6}\right) - x_7}{x_8}$$

where:
G is representative of analyte concentration;
$I_1 \approx$ magnitude of second transient signal at interval 19;
$I_2 \approx$ magnitude of second transient signal at interval 16;
$I_3 \approx$ magnitude of second transient signal at interval 11;
$I_4 \approx$ magnitude of second transient signal at interval 5;
$x_1 \approx (-)1.68$;
$x_2 \approx 0.95$;
$x_3 \approx (-)4.97$;
$x_4 \approx 6.29$;
$x_5 \approx 3.08$;
$x_6 \approx (-)5.84$;
$x_7 \approx (-)0.47$; and
$x_8 \approx 0.01$.

18. The method of claim 11, in which the determination of analyte concentration is obtained by utilizing an equation of the form:

$$G = \frac{\left(\left|\frac{I_1}{I_2}\right|^{x_1} \times \frac{x_2|I_3|^3 + x_3|I_3|^2 + x_4|I_3| + x_5}{x_6|I_4|^2 + x_7|I_4| + x_8}\right) - x_9}{x_{10}}$$

where:
G is representative of analyte concentration;
$I_1 \approx$ magnitude of second transient signal at interval 16;
$I_2 \approx$ magnitude of second transient signal at interval 5;
$I_3 \approx$ magnitude of second transient signal at interval 12;
$I_4 \approx$ magnitude of second transient signal at interval 14;
$x_1 \approx 1.18$;
$x_2 \approx 0.97$;
$x_3 \approx (-)11.32$;
$x_4 \approx 38.76$;
$x_5 \approx (-)39.32$;
$x_6 \approx 0.0928$;
$x_7 \approx (-)0.85$;
$x_8 \approx 1.75$;
$x_9 \approx (-)9.38$; and
$x_{10} \approx 0.25$.

19. The method of claim 11, in which the magnitude of the second transient signal at each of the plurality of discrete intervals comprises an average magnitude of measured magnitudes at each discrete interval.

20. The method of claim 4, further comprising the step of dividing the first transient signal into discrete intervals with respect to the specific range of time.

21. The method of claim 1, further comprising dividing the first transient signal into discrete intervals with respect to the specific range of time.

22. The method of claim 20, in which the dividing comprises dividing the first transient signal into at least 22 intervals in sequence starting from interval one at about the start time to interval twenty-two at about the end time.

23. The method of claim 22, in which the determination of analyte concentration is obtained by utilizing an equation of the form:

$$G = \frac{\left(\left|\frac{I_3}{I_4}\right|\right)^{x_1} \times \left(\frac{|I_2| + x_4|I_5| - x_5|I_1|}{|I_2| + x_4|I_5|}|I_5|\right) - x_2}{x_3}$$

where:
G is representative of analyte concentration;
$I_1 \approx$ magnitude of first transient signal at interval 17;
$I_2 \approx$ magnitude of first transient signal at interval 13;
$I_3 \approx$ magnitude of first transient signal at interval 5;
$I_4 \approx$ magnitude of first transient signal at interval 3;
$I_5 \approx$ magnitude of first transient signal at interval 22;
$x_1 \approx 0.75$;
$x_2 \approx 337.27$;
$x_3 \approx (-)16.81$;
$x_4 \approx 1.41$; and
$x_5 \approx 2.67$.

24. The method of claim 22, in which the determination of analyte concentration is obtained by utilizing an equation of the form:

$$G = \frac{x_1(|I_1|)\left(x_2 - \frac{x_3}{|I_2|}\right) - x_4}{x_5}$$

where:
G is representative of analyte concentration;
$I_1 \approx$ magnitude of first transient signal at interval 11;
$I_2 \approx$ magnitude of first transient signal at interval 7;
$x_1 \approx 0.59$;
$x_2 \approx 2.51$;
$x_3 \approx (-)12.74$;
$x_4 \approx (-)188.31$; and
$x_5 \approx 9.2$.

25. The method of claim 22, in which the determination of analyte concentration is obtained by utilizing an equation of the form:

$$G = \frac{x_1 \ln\left(x_2 \frac{|I_1|}{|I_2|}\right)^{x_3} |I_3|^{x_4} - x_5}{x_6}$$

where:
G is representative of analyte concentration;
$I_1 \approx$ magnitude of first transient signal at interval 20;
$I_2 \approx$ magnitude of first transient signal at interval 22;
$I_3 \approx$ magnitude of first transient signal at interval 19;
$x_1 \approx 20.15$;
$x_2 \approx 1.0446$;
$x_3 \approx 0.95$;
$x_4 \approx 1.39$;
$x_5 \approx (-)0.71$; and
$x_6 \approx 0.11$.

26. The method of claim 22, in which the determination of analyte concentration is obtained by utilizing an equation of the form:

$$G = \frac{x_3 \left|\frac{I_1}{I_2}\right|^{\left(x_1 - x_2 \frac{|I_3|}{|I_4|}\right)} \times |I_5| - x_5}{x_4}$$

where:
G is representative of analyte concentration;
$I_1 \approx$ magnitude of first transient signal at interval 5;
$I_2 \approx$ magnitude of first transient signal at interval 1;
$I_3 \approx$ magnitude of first transient signal at interval 2;
$I_4 \approx$ magnitude of first transient signal at interval 10;
$I_5 \approx$ magnitude of first transient signal at interval 22;
$x_1 \approx 0.70$;
$x_2 \approx 0.49$;
$x_3 \approx 28.59$;
$x_4 \approx 0.7$; and
$x_5 \approx 15.51$.

27. The method of claim 22, in which the determination of analyte concentration is obtained by utilizing an equation of the form:

$$G = \frac{\left(\left|\frac{I_1}{I_2}\right|^{x_1} \times \frac{x_2|I_3|^2 + x_3|I_3| + x_4}{x_5|I_4| + x_6}\right) - x_7}{x_8}$$

where:
G is representative of analyte concentration;
$I_1 \approx$ magnitude of first transient signal at interval 19;
$I_2 \approx$ magnitude of first transient signal at interval 16;
$I_3 \approx$ magnitude of first transient signal at interval 11;
$I_4 \approx$ magnitude of first transient signal at interval 5;
$x_1 \approx (-)1.68$;
$x_2 \approx 0.95$;
$x_3 \approx (-)4.97$;
$x_4 \approx 6.29$;
$x_5 \approx 3.08$;
$x_6 \approx (-)5.84$;
$x_7 \approx (-)0.47$; and
$x_8 \approx 0.01$.

28. The method of claim 22, in which the determination of analyte concentration is obtained by utilizing an equation of the form:

$$G = \frac{\left(\left|\frac{I_1}{I_2}\right|^{x_1} \times \frac{x_2|I_3|^3 + x_3|I_3|^2 + x_4|I_3| + x_5}{x_6|I_4|^2 + x_7|I_4| + x_8}\right) - x_9}{x_{10}}$$

where:
G is representative of analyte concentration;
$I_1 \approx$ magnitude of first transient signal at interval 16;
$I_2 \approx$ magnitude of first transient signal at interval 5;
$I_3 \approx$ magnitude of first transient signal at interval 12;
$I_4 \approx$ magnitude of first transient signal at interval 14;
$x_1 \approx 1.18$;
$x_2 \approx 0.97$;
$x_3 \approx (-)11.32$;
$x_4 \approx 38.76$;
$x_5 \approx (-)39.32$;
$x_6 \approx 0.0928$;
$x_7 \approx (-)0.85$;
$x_8 \approx 1.75$;
$x_9 \approx (-)9.38$; and
$x_8 \approx 0.25$.

29. The method of claim 28, in which the magnitude of the first transient signal at each of the plurality of discrete intervals comprises an average magnitude of measured magnitudes at each discrete interval.

30. The method of claim 28, in which the applying of the first signal and the driving of the second signal is in sequential order.

31. The method of claim 28, in which the applying of the first signal overlaps with the driving of the second signal.

32. The method of claim 28, in which the applying of the first signal comprises directing an alternating signal to the sample so that a physical characteristic of the sample is determined from an output of the alternating signal.

33. The method of claim 28, in which the applying of the first signal comprises directing an optical signal to the sample so that a physical characteristic of the sample is determined from an output of the optical signal.

34. The method of claim 28, in which the physical characteristic comprises at least one of viscosity, hematocrit, temperature or density of the sample.

35. The method of claim 28, in which the physical characteristic comprises hematocrit and the analyte comprises glucose.

36. The method of claim 32, in which the directing comprises driving first and second alternating signals at different respective frequencies in which a first frequency comprises a lower frequency than the second frequency.

37. The method of claim 36, in which the first frequency is at least one order of magnitude lower than the second frequency.

38. The method of claim 37, in which the first frequency comprises any frequency in the range of about 10 kHz to about 250 kHz.

39. The method of claim 1, in which the obtaining comprises extracting from the first transient signal a second transient signal referenced with respect to the second sampling time duration.

40. The method of claim 1, in which the obtaining comprises removing signals from the first transient signals that are outside of the second sampling time duration to leave the second transient signal within the second sampling time duration.

41. The method of claim 39, in which the deriving comprises storing magnitudes of the second transient signal for each discrete interval in the second sampling time duration.

* * * * *